(12) United States Patent
Bahr et al.

(10) Patent No.: US 11,625,829 B2
(45) Date of Patent: Apr. 11, 2023

(54) SPECTRAL UNMIXING OF FLUORESCENCE IMAGING USING RADIOFREQUENCY-MULTIPLEXED EXCITATION DATA

(71) Applicant: Becton, Dickinson and Company, Franklin Lakes, NJ (US)

(72) Inventors: Matthew Bahr, San Jose, CA (US); Keegan Owsley, Campbell, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/714,875

(22) Filed: Apr. 6, 2022

(65) Prior Publication Data
US 2022/0230317 A1 Jul. 21, 2022

Related U.S. Application Data

(63) Continuation of application No. 16/817,135, filed on Mar. 12, 2020, now Pat. No. 11,328,422.

(60) Provisional application No. 62/822,789, filed on Mar. 22, 2019.

(51) Int. Cl.
| | |
|---|---|
| *G06T 7/00* | (2017.01) |
| *G01N 15/14* | (2006.01) |
| *G01N 21/64* | (2006.01) |
| *C12Q 1/02* | (2006.01) |

(52) U.S. Cl.
CPC .............. *G06T 7/0014* (2013.01); *C12Q 1/02* (2013.01); *G01N 15/14* (2013.01); *G01N 21/6428* (2013.01); *G01N 2015/149* (2013.01); *G01N 2021/6439* (2013.01);
(Continued)

(58) Field of Classification Search
CPC ....... G01N 15/1475; G01N 2015/1006; G01N 2015/1472; G01N 2015/149; G02B 6/06; G06T 2207/10056; G06T 2207/10064; G06T 2207/10068; G06T 2207/20032; G06T 2207/20036; G06T 2207/20224; G06T 2207/30024; G06T 5/002;
(Continued)

(56) References Cited

U.S. PATENT DOCUMENTS

| | | | |
|---|---|---|---|
| 2007/0049996 A1* | 3/2007 | Black | A61B 18/203 607/89 |
| 2008/0051665 A1 | 2/2008 | Xu et al. | |
| 2012/0129213 A1 | 5/2012 | Hoyt | |

(Continued)

FOREIGN PATENT DOCUMENTS

| | | |
|---|---|---|
| EP | 1573641 A | 6/2013 |
| WO | WO199715229 A1 | 5/1997 |

(Continued)

*Primary Examiner* — Alex Kok S Liew
(74) *Attorney, Agent, or Firm* — Bret E. Field; Bozicevic, Field & Francis LLP

(57) ABSTRACT

Disclosed herein include embodiments of a system, a device, and a method for sorting a plurality cells of a sample. A plurality of raw images comprising pixels of complex values in a frequency space can be generated from a plurality of channels of fluorescence intensity data of fluorescence emissions of fluorophores, the fluorescence emissions being elicited by fluorescence imaging using radiofrequency-multiplexed excitation in a temporal space. Spectral unmixing can be performed on the raw images prior to a sorting decision being made.

20 Claims, 45 Drawing Sheets

(52) U.S. Cl.
CPC .............. *G06T 2207/10064* (2013.01); *G06T 2207/20056* (2013.01); *G06T 2207/30024* (2013.01)

(58) Field of Classification Search
CPC .... G06T 5/20; G06T 5/50; G06T 7/80; G06V 20/69; G06V 20/693; G06V 20/695
See application file for complete search history.

(56) References Cited

U.S. PATENT DOCUMENTS

| | | | |
|---|---|---|---|
| 2012/0226119 A1* | 9/2012 | Dobosz .............. | A61K 49/0058 600/317 |
| 2017/0268981 A1 | 9/2017 | Diebold et al. | |
| 2017/0328826 A1 | 11/2017 | Diebold et al. | |
| 2018/0196246 A1* | 7/2018 | Bares ................... | G01J 3/0208 |
| 2018/0328848 A1 | 11/2018 | Murphy et al. | |

FOREIGN PATENT DOCUMENTS

| | | |
|---|---|---|
| WO | WO2015066552 A1 | 5/2015 |
| WO | WO2018052798 A1 | 3/2018 |
| WO | WO2020047468 A1 | 3/2020 |
| WO | WO2020081292 A1 | 4/2020 |
| WO | WO2020139848 A1 | 7/2020 |

* cited by examiner

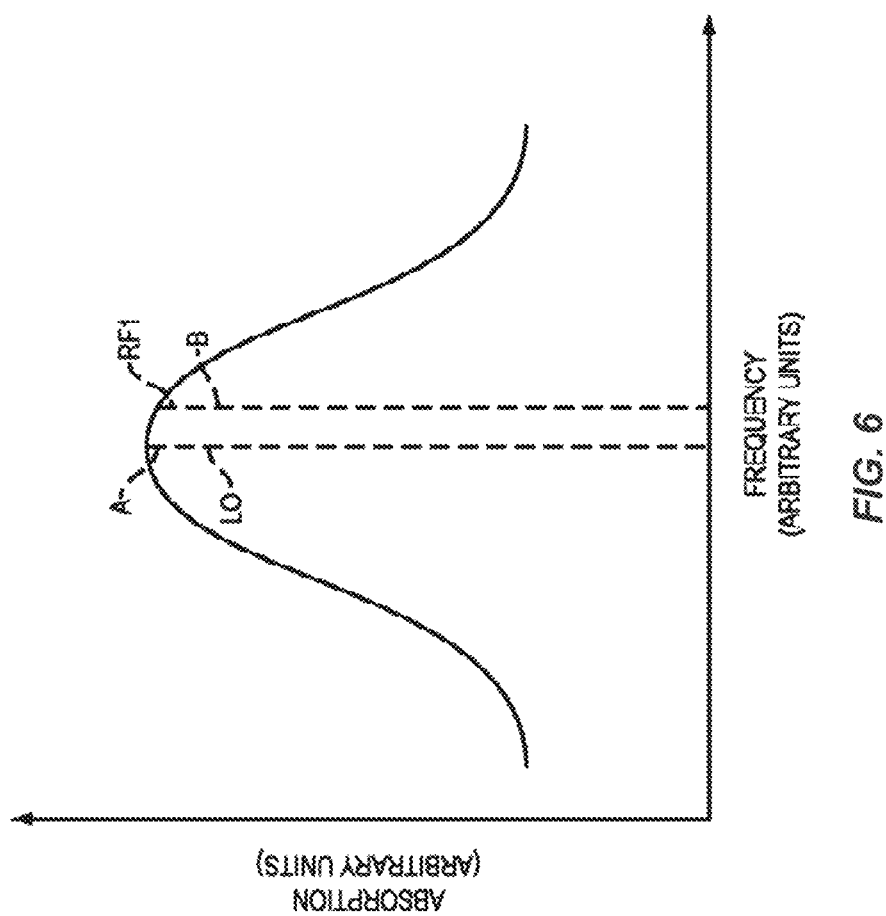

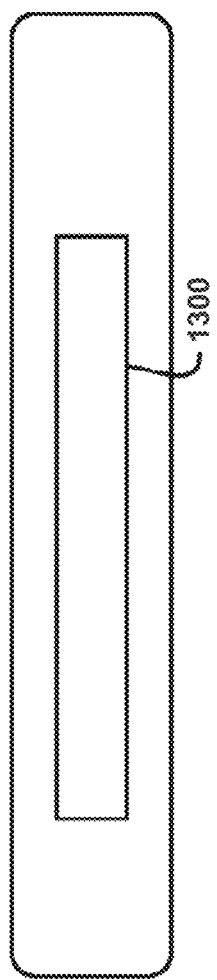

FIG. 26A  No Compensation
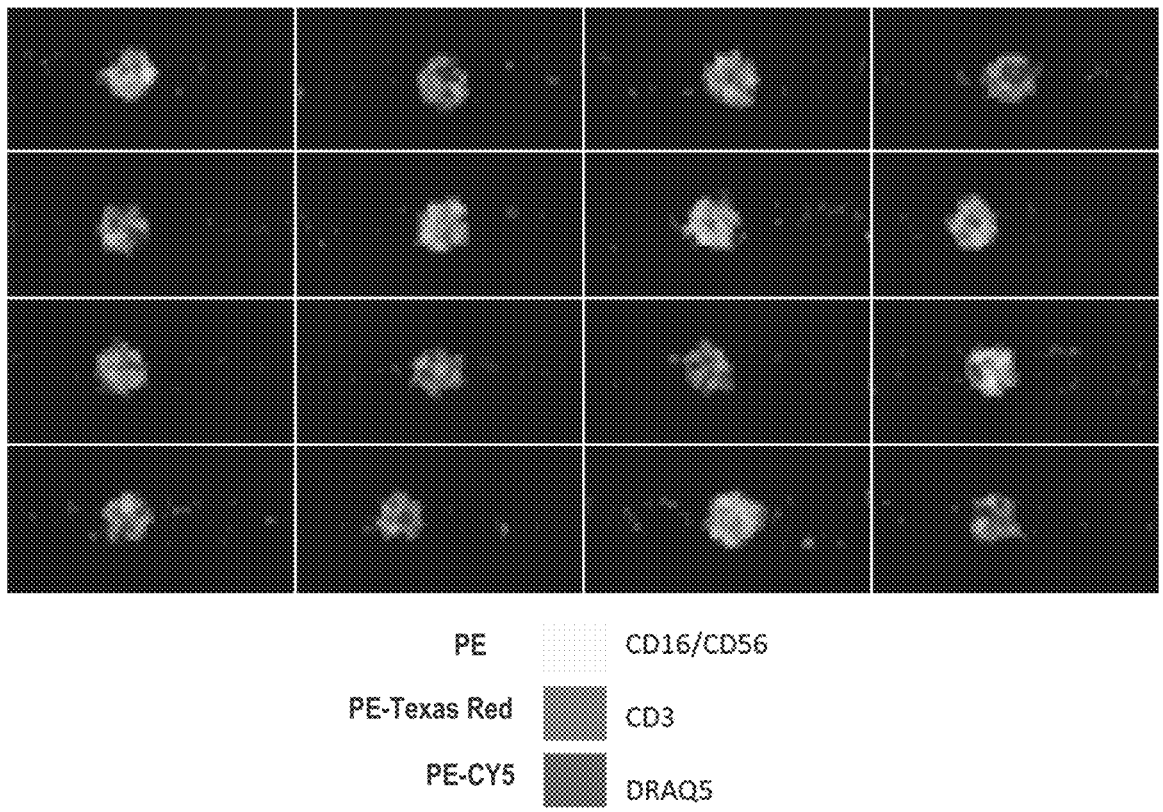
PE CD16/CD56
PE-Texas Red CD3
PE-CY5 DRAQ5
FIG. 26B  With Compensation
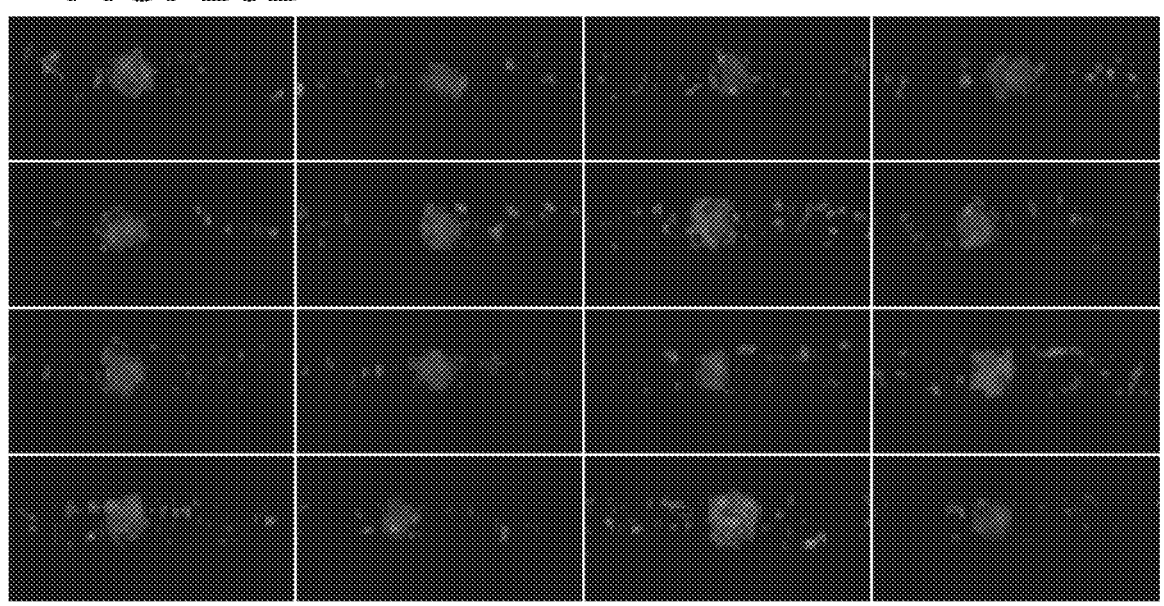

FIG. 28B1
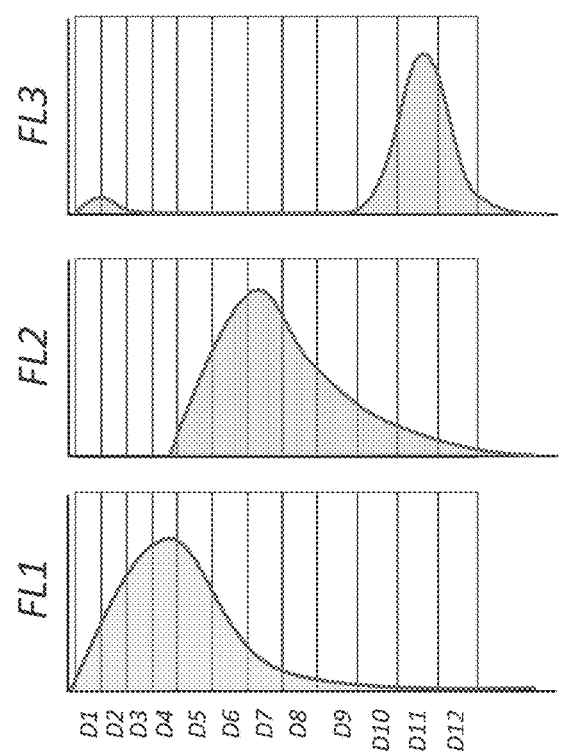

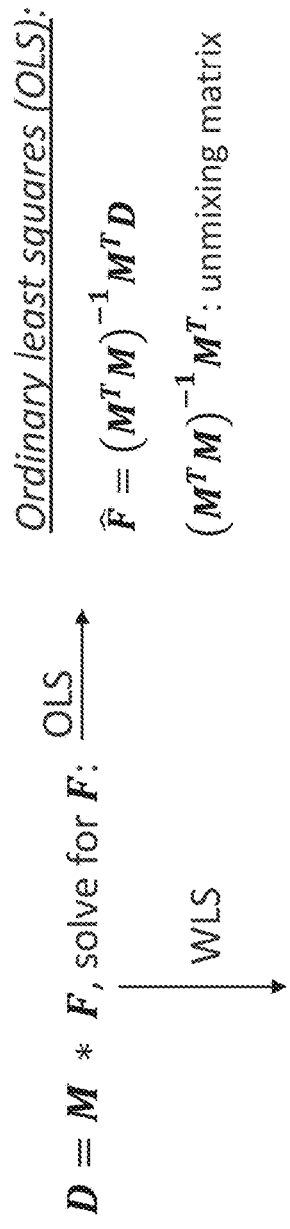

FIG. 28B2

$D$ : raw values or phase-corrected values
$F$ : true fluorophore abundances
$\hat{F}$ : estimated fluorophore abundances
$M$ : unmixing matrix $D = M * F$, solve for $F$:

*Ordinary least squares (OLS):*

$$\hat{F} = (M^T M)^{-1} M^T D$$

$(M^T M)^{-1} M^T$ : unmixing matrix

*Weighted least squares (WLS):*

$$\hat{F} = (M^T W M)^{-1} M^T W D$$

$(M^T W M)^{-1} M^T W$ : unmixing matrix $$W = \begin{bmatrix} W_{11} & 0 & \cdots & 0 \\ 0 & W_{22} & \cdots & 0 \\ \vdots & \vdots & \ddots & \vdots \\ 0 & 0 & \cdots & W_{dd} \end{bmatrix}$$

$$W_{ii} = \frac{1}{\sigma_i^2} \approx \frac{1}{D_i + \lambda_i}$$

$\sigma_i^2$ : variance for channel $i$
$D_i$ : uncorrected values for channel $i$
$\lambda_i$ : constant noise for channel $i$

SPECTRAL UNMIXING OF FLUORESCENCE IMAGING USING RADIOFREQUENCY-MULTIPLEXED EXCITATION DATA

CROSS-REFERENCE TO RELATED APPLICATION AND FIELD

Pursuant to 35 U.S.C. § 119(e), this application claims priority to the filing date of U.S. Provisional Patent Application Ser. No. 62/822,789, filed Mar. 22, 2019; the disclosure of which application is incorporated herein by reference. The present invention relates generally to devices and methods for determining characteristics of particles flowing through a flow cytometer, e.g., via fluorescence analysis of samples, and more particularly to devices and methods for sorting particles, e.g., sorting cells in a flow cytometer based, for example, on their characteristics.

INTRODUCTION

Background

The isolation of subpopulations or even single cells from heterogeneous populations has a variety of applications in modern biology and biomedicine. Some conventional techniques for separating cell subpopulations include fluorescence activated cell sorting (FACS), magnetic activated cell sorting (MACS), laser capture microdissection, and DEP array sorting. These techniques, while employed routinely in cell sorting applications, present a number of shortcomings. For example, FACS, which is widely used across all areas of cell biology, lack sub-cellular resolution and hence makes sorting decisions based only on an average of a cell's parameters. Moreover, conventional sorting methods based on imaging cells are not generally capable of being used in high throughput cell separation applications due to their high latency in making sorting decisions. Accordingly, there is a need for improved methods and systems for sorting cells, for example, in a flow cytometry system.

SUMMARY

Disclosed herein include embodiments of a system, a device, and a method for sorting a plurality cells of a sample. The method comprises: under control of a hardware processor (or a processor generally, such as a virtual processor): illuminating a cell of a sample comprising a plurality of cells with a laser beam having a plurality of different optical frequencies to elicit fluorescence emissions of a plurality of fluorophores associated with the cell. The method can include: detecting the fluorescence emissions at different wavelengths to obtain a plurality of channels of fluorescence intensity data corresponding to the plurality of fluorophores in a temporal space. The method can include: generating a plurality of raw images comprising a plurality of pixels of complex values in a frequency space from the plurality of channels of fluorescence intensity data. The method can include: generating a plurality of phase-adjusted images comprising a plurality of pixels of complex values in the frequency space from the plurality of raw images using one or more channel phase adjustments for each of the plurality of channels of the fluorescence intensity data. The method can include: generating a plurality of unmixed images comprising a plurality of pixels of complex values in the frequency space from the plurality of phase-adjusted images using an unmixing matrix on the complex values of corresponding pixels of the plurality of phase-adjusted images. The method can include: generating a plurality of phase-corrected images comprising a plurality of pixels of complex values, or real values, in the frequency space from the plurality of unmixed images based on a property of each of the plurality of fluorophores. The method can include: determining a sorting decision for the cell based on the plurality of phase-corrected images.

Disclosed herein include embodiments of a method for sorting a plurality cells of a sample. The method comprises: under control of a processor (e.g., a hardware processor, and a virtual processor): illuminating a cell of a sample comprising a plurality of cells with a laser beam having a plurality of different optical frequencies to elicit fluorescence emissions of a plurality of fluorophores associated with the cell. The method can include: detecting the fluorescence emissions at different wavelengths to obtain a plurality of channels of fluorescence intensity data corresponding to the plurality of fluorophores in a temporal space. The method can include: generating a plurality of raw images comprising complex values in a frequency space from the plurality of channels of fluorescence intensity data. The method can include: generating a plurality of unmixed images comprising complex values, or real values, in the frequency space from the plurality of raw images using an unmixing matrix on corresponding complex values of the plurality of raw images. The method can include: determining a sorting decision for the cell based on the plurality of unmixed images.

Disclosed herein include embodiments of a method for sorting a plurality cells of a sample. The method can comprise: under control of a hardware processor: receiving a plurality of channels of fluorescence intensity data, corresponding to a plurality of fluorophores in a temporal space, of fluorescence emissions at different wavelengths from the plurality of fluorophores associated with a cell of a sample comprising a plurality of cells. The fluorescence emissions can be elicited after illuminating the cell with a laser beam having a plurality of different optical frequencies. The method can include: generating a plurality of raw images comprising complex values in a frequency space from the plurality of channels of fluorescence intensity data. The method can include: generating a plurality of unmixed images comprising complex values, or real values, in the frequency space from the plurality of raw images using an unmixing matrix on corresponding complex values of the plurality of raw images. The method can include: determining a sorting decision for the cell based on the plurality of unmixed images. The method can include: illuminating the cell with the laser beam to elicit the fluorescence emissions of the plurality of channels of fluorescence intensity data in the temporal space.

In some embodiments, the plurality of raw images comprises a plurality of pixels of the complex values of the plurality of raw images. In some embodiments, the method can comprise: generating a plurality of phase-adjusted images comprising complex values in the frequency space from the plurality of raw images using one or more channel phase adjustments for each of the plurality of channels of the fluorescence intensity data, wherein generating the plurality of unmixed images comprises: generating the plurality of unmixed images from the plurality of phase-adjusted images using the unmixing matrix on the corresponding complex values of the plurality of phase-adjusted images. The plurality of phase-adjusted images can comprise a plurality of pixels of the complex values of the plurality of phase-adjusted images. In some embodiments, the method can include: generating a plurality of phase-corrected images comprising complex values in the frequency space from the plurality of unmixed images based on a property of each of the plurality of fluorophores, wherein determining the sorting decision comprises: determining the sorting decision for the cell based on the plurality of phase-corrected images. The plurality of phase-corrected images can comprise a plurality of pixels of the complex values of the plurality of phase-corrected images.

In some embodiments, generating the plurality of raw images comprises: generating the plurality of raw images in the frequency space from the plurality of channels of fluorescence intensity data using a temporal-to-frequency space transformation. The temporal-to-frequency space transformation can comprise a Fourier transform. The Fourier transform can comprise a discrete Fourier transform. The discrete Fourier transform can comprise a fast Fourier transform. The Fourier transform can comprise a sliding window Fourier transform. A sliding window of the sliding window Fourier transform can have a size of $m_1$. Generating the plurality of raw images can comprise generating the plurality of raw images using a temporal-to-frequency transformation matrix representing the temporal-to-frequency space transformation.

In some embodiments, the one or more channel phases comprise a brightfield phase, a calibration phase, and a phase offset for each of the plurality of channels. One or more channel phase adjustments can correct or account for the channel phases, such as the brightfield phase, the calibration phase, and the phase offset. Generating the plurality of phase-adjusted images can comprise, for each channel of the plurality of channels: multiplying the complex values of a raw image of the plurality of raw images corresponding to the channel to generate a phase-adjusted image of the plurality of phase-adjusted images corresponding to the channel. The one or more channel phase adjustments can comprise, or comprise only, complex values. The one or more channel phase adjustments can comprise one or real values. Generating the plurality of phase-adjusted images can comprise generating the plurality of phase-adjusted images using one or more channel phase adjustment matrices representing the one or more channel phase adjustments. The method can comprise: determining or receiving the one or more channel phase adjustments.

In some embodiments, generating the plurality of unmixed images comprises: generating a vector comprising complex values of corresponding pixels of the plurality of phase-adjusted images; multiplying the vector with the unmixing matrix to generate an unmixed vector comprising unmixed complex values; and generating the plurality of unmixed images comprising the corresponding pixels with the unmixed complex values. The vector can have a size of $1 \times n_1$, the unmixing matrix can have a size of $n_1 \times n_2$, and/or the unmixed vector can have a size of $1 \times n_2$. In some embodiments, generating the plurality of unmixed images comprises: generating the plurality of unmixed images from the plurality of phase-adjusted images using an unmixing matrix of a plurality of unmixing matrices, for corresponding pixels of the plurality of phase-adjusted images, on the complex values of the corresponding pixels. The plurality of unmixing matrices can comprise $m_2$ unmixing matrices. The unmixing matrix can comprise or comprises only of real values or complex values. The method can comprise: determining or receiving the unmixing matrix.

In some embodiments, generating the plurality of phase-corrected images comprises: generating a phase-corrected image of the plurality of phase-corrected images from a unmixed image of the plurality of unmixed images corresponding to a fluorophore of the plurality of channels using a plurality of fluorophore phase corrections for the fluorophore of the plurality of fluorophores. The plurality of fluorophore phase corrections for the fluorophore can be related to a property of the fluorophore. The property of the fluorophore can comprise a lifetime of the fluorophore. The plurality of fluorophore phase corrections for the fluorophore can comprise complex values. The method can comprise: determining or receiving the plurality of lifetime corrections. Generating the plurality of phase-corrected images can comprise generating the plurality of phase-corrected images using a fluorophore phase correction matrix for the fluorophore representing the plurality of fluorophore phase corrections.

In some embodiments, the method comprises: generating a plurality of visual representations of the plurality of phase-corrected images based on the real components of the complex values of the plurality of phase-corrected images. The method can comprise generating a plurality of visual representations of the plurality of phase-corrected images based on the amplitudes of the complex values of the plurality of phase-corrected images. Determining the sorting decision can comprise determining the sorting decision for the cell based on the plurality of visual representations of the plurality of phase-corrected images. The method can include generating a combined visual representation form the plurality of visual representations.

In some embodiments, two or more of generating the plurality of raw images, generating the plurality of phase-adjusted images, generating the plurality of unmixed images, and generating the plurality of phase-corrected images is performed using a combined matrix. Generating the plurality of raw images and generating the plurality of phase-adjusted images can comprise: generating the plurality of phase-adjusted images from the plurality of channels of fluorescence intensity data using a combined matrix. Generating the plurality of unmixed images and generating the plurality of phase-corrected images can comprise: generating the plurality of phase-corrected images from the plurality of phase-adjusted images using a combined matrix comprising the unmixing matrix. Generating the plurality of raw images, generating the plurality of phase-adjusted images, generating the plurality of unmixed images, and generating the plurality of phase-corrected images can comprise generating the plurality of phase-corrected images from the plurality of channels of fluorescence intensity using a combined matrix comprising the unmixing matrix.

In some embodiments, the method comprises: generating a plurality of channels of corrected fluorescence intensity data from the plurality of phase-corrected images. Generating the plurality of channels of corrected fluorescence intensity data can comprise generating the plurality of channels of corrected fluorescence intensity data form the plurality of phase-corrected images using a frequency- to temporal-space transformation. The method can comprise: determining an estimate of a characteristic of the cell based on the plurality of channels of corrected fluorescence intensity data, wherein determining the sorting decision comprises determining the sorting decision of the cell based on the estimate of the characteristic of the cell. The characteristic of the cell can comprise a size of the cell, a ratio of sizes of the cell in two different dimensions, co-localization of fluorescence emissions by two or more of the plurality of fluorophores associated with the cell, a ratio of sizes of the cytoplasm and the nucleus of the cell, a degree of punctateness of fluorescence emission of the cell, a measure of the spatial distribution of the fluorescence emission, a measure of location or orientation of the cell, a measure of the eccentricity of the cell, a measure of the similarity of the cell to a reference cell, a measure of the degree to which the cell lies in a focal point of the laser beam, or a combination thereof.

In some embodiments, the laser beam comprises a reference laser beam and a plurality of radiofrequency-shifted laser beams. The number of the plurality of radiofrequency-shifted laser beams can be $m_2$. The reference laser beam can spatially overlap the plurality of radiofrequency-shifted laser beams. None of the plurality of radiofrequency-shifted laser beams spatially overlaps with one another. The reference laser beam and one or more of the plurality of radiofrequency-shifted laser beams can be capable of eliciting the fluorescence emission of a fluorophore of the plurality of fluorophores. Illuminating the cell can comprise illuminating a plurality of spatial locations of the cell with the plurality of radiofrequency-shifted laser beams concurrently. None of the plurality of spatial locations of the cell overlaps with one another.

In some embodiments, the number of the plurality of raw images, the number of the plurality of phase-adjusted images, the number of the plurality of unmixed images, and the number of the plurality of phase-corrected images are identical. The number of the plurality of raw images, the number of the plurality of phase-adjusted images, the number of the plurality of unmixed images, and/or the number of the plurality of phase-corrected images can be $n_1$. The plurality of raw images can be associated with a first temporal dimension and a first frequency dimension, the plurality of phase-adjusted images can be associated with a second temporal dimension and a second frequency dimension, the plurality of unmixed images can be associated with a third temporal dimension and a third frequency dimension, and/or the plurality of phase-corrected images can be associated with a fourth temporal dimension and a fourth frequency dimension. Two or more of the first temporal dimension, the second temporal dimension, the third temporal dimension, and the fourth temporal dimension can have an identical size and/or an identical number of pixels along the dimension. The first temporal dimension, the second temporal dimension, the third temporal dimension, and the fourth temporal dimension can have the identical size and/or the identical number of pixels. The first frequency dimension, the second frequency dimension, the third frequency dimension, and/or the fourth frequency dimension have a size of $m_2$ and/or $m_2$ pixels. In some embodiments, $m_2$ equals to $\frac{1}{2} * m_1$. In some embodiments, $m_2$ is smaller than $\frac{1}{2} * m_1$. Two or more of the first frequency dimension, the second frequency dimension, the third frequency dimension, and the fourth frequency dimension can have an identical size and/or an identical number of pixels. The first frequency dimension, the second frequency dimension, the third frequency dimension, and the fourth frequency dimension can have the identical size and/or the identical number of pixels. The size of and/or the number of pixels along the first frequency dimension, the size of and/or the number of pixels along the second frequency dimension, the size of and/or the number of pixels along the third frequency dimension, and/or the size of and/or the number of pixels of the fourth frequency dimension can be identical to the number of the plurality of radiofrequency-shifted laser beams. The pixels along the first frequency dimension, the pixels along the second frequency dimension, the pixels along the third frequency dimension, and/or the pixels along the fourth frequency dimension can correspond to the plurality of radiofrequency-shifted laser beams. The pixels along the first frequency dimension, the pixels along the second frequency dimension, the pixels along the third frequency dimension, and/or the pixels along the fourth frequency dimension can correspond to the plurality of spatial locations of the cell.

In some embodiments, the fluorescence emissions of two of the plurality of fluorophores overlap spectrally. The fluorescence emissions of three of the plurality of fluorophores overlap spectrally. The fluorescence emissions of five of the plurality of fluorophores overlap spectrally. The fluorescence emissions of a first fluorophore and a second fluorophore of the plurality of fluorophores overlap spectrally, and the fluorescence emissions of the second fluorophore and a third fluorophore of the plurality of fluorophores overlap spectrally. The fluorescence emissions of the first fluorophore and the third fluorophore overlap spectrally.

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells. The cell sorter system can comprise: a plurality of photodetectors configured to detect the fluorescence emissions of the plurality of fluorophores (e.g., each photodetector is configured to detect the fluorescence emission of a fluorophore of the plurality of fluorophores). The cell sorter system can comprise: non-transitory memory configured to store executable instructions; and a processor in communication with the non-transitory memory, the hardware processor programmed by the executable instructions to: cause the laser beam to illuminate the cell to elicit fluorescence emissions of a plurality of fluorophores associated with the cell. The processor can be programmed by the executable instructions to: cause the plurality photodetectors to detect the fluorescence emissions at the different wavelengths to obtain a plurality of channels of fluorescence intensity data corresponding to the plurality of fluorophores in a temporal space. The processor can be programmed by the executable instructions to: generate a plurality of raw images comprising a plurality of pixels of complex values in a frequency space from the plurality of channels of fluorescence intensity data. The processor can be programmed by the executable instructions to: generate a plurality of phase-adjusted images comprising a plurality of pixels of complex values in the frequency space from the plurality of raw images using one or more channel phase adjustments for each of the plurality of channels of the fluorescence intensity data. The processor can be programmed by the executable instructions to: generate a plurality of unmixed images comprising a plurality of pixels of complex values in the frequency space from the plurality of phase-adjusted images using an unmixing matrix on the complex values of corresponding pixels of the plurality of phase-adjusted images. The processor can be programmed by the executable instructions to: generate a plurality of phase-corrected images comprising a plurality of pixels of complex values, or real values, in the frequency space from the plurality of unmixed images based on a property of each of the plurality of fluorophores. The processor can be programmed by the executable instructions to: determine a sorting decision for the cell based on the plurality of phase-corrected images.

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells; a plurality of photodetectors configured to detect the fluorescence emissions of the plurality of fluorophores (e.g., each photodetector is configured to detect the fluorescence emission of a fluorophore of the plurality of fluorophores); non-transitory memory configured to store executable instructions; and a processor in communication with the non-transitory memory, the hardware processor programmed by the executable instructions to: cause the laser beam to illuminate the cell to elicit fluorescence emissions of a plurality of fluorophores associated with the cell. The processor can be programmed by the executable instructions to: cause the plurality photodetectors to detect the fluorescence emissions at the different wavelengths to obtain a plurality of channels of fluorescence intensity data corresponding to the plurality of fluorophores in a temporal space. The processor can be programmed by the executable instructions to: generate a plurality of raw images comprising complex values in a frequency space from the plurality of channels of fluorescence intensity data. The processor can be programmed by the executable instructions to: generate a plurality of unmixed images comprising complex values, or real values, in the frequency space from the plurality of raw images using an unmixing matrix on corresponding complex values of the plurality of raw images. The processor can be programmed by the executable instructions to: determine a sorting decision for the cell based on the plurality of unmixed images.

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells; a plurality of photodetectors configured to detect the fluorescence emissions of the plurality of fluorophores (e.g., each photodetector is configured to detect the fluorescence emission of a fluorophore of the plurality of fluorophores); non-transitory memory configured to store executable instructions; and a processor in communication with the non-transitory memory, the hardware processor programmed by the executable instructions to: receive a plurality of channels of fluorescence intensity data, corresponding to the plurality of fluorophores in a temporal space, of the fluorescence emissions at the different wavelengths from the plurality of fluorophores associated with the cell, wherein the fluorescence emissions are detected by the plurality of photodetectors, and wherein the fluorescence emissions are elicited after the cell is illuminated by the laser light source. The processor can be programmed by the executable instructions to: generate a plurality of raw images comprising complex values in a frequency space from the plurality of channels of fluorescence intensity data. The processor can be programmed by the executable instructions to: generate a plurality of unmixed images comprising complex values, or real values, in the frequency space from the plurality of raw images using an unmixing matrix on corresponding complex values of the plurality of raw images. The processor can be programmed by the executable instructions to: determine a sorting decision for the cell based on the plurality of unmixed images.

In some embodiments, to receive the plurality of channels of fluorescence intensity data, the processor is programmed by the executable instructions to: cause the laser beam to illuminate the cell to elicit fluorescence emissions of a plurality of fluorophores associated with the cell; and cause the plurality photodetectors to detect the fluorescence emissions at the different wavelengths to obtain the plurality of channels of fluorescent intensity data corresponding to the plurality of fluorophores in the temporal space. The plurality of raw images can comprise a plurality of pixels of the complex values of the plurality of raw images. The processor can be programmed by the executable instructions to: generate a plurality of phase-adjusted images comprising complex values in the frequency space from the plurality of raw images using one or more channel phase adjustments for each of the plurality of channels of the fluorescent intensity data. To generate the plurality of unmixed images, the processor can be programmed by the executable instructions to: generate the plurality of unmixed images from the plurality of phase-adjusted images using the unmixing matrix on the corresponding complex values of the plurality of phase-adjusted images. The plurality of phase-adjusted images can comprise a plurality of pixels of the complex values of the plurality of phase-adjusted images. The processor can be programmed by the executable instructions to: generate a plurality of phase-corrected images comprising complex values in the frequency space from the plurality of unmixed images based on a property of each of the plurality of fluorophores. To determine the sorting decision, the processor can be programmed by the executable instructions to: determine the sorting decision for the cell based on the plurality of phase-corrected images. The plurality of phase-corrected images can comprise a plurality of pixels of the complex values of the plurality of phase-corrected images.

In some embodiments, the hardware processor comprises a field-programmable gate array (FPGA). In some embodiments, to generate the plurality of raw images, the processor is programmed by the executable instructions to: generate the plurality of raw images in the frequency space from the plurality of channels of fluorescence intensity data using a temporal-to-frequency space transformation. The temporal-to-frequency space transformation can comprise a Fourier transform. The Fourier transform can comprise a discrete Fourier transform. The discrete Fourier transform can comprise a fast Fourier transform. The Fourier transform can comprise a sliding window Fourier transform. A sliding window of the sliding window Fourier transform can have a size of $m_1$.

In some embodiments, the one or more channel phase adjustments correct or account for channel phases (e.g., channel-specific phases) comprising a brightfield phase, a calibration phase, and a phase offset for each of the plurality of channels. To generate the plurality of phase-adjusted images, the processor can be programmed by the executable instructions to, for each channel of the plurality of channels: multiply the complex values of a raw image of the plurality of raw images corresponding to the channel to generate a phase-adjusted image of the plurality of phase-adjusted images corresponding to the channel. The one or more channel phase adjustments can comprise, or comprise only, complex values. The one or more channel phase adjustments can comprise real values. The processor can be programmed by the executable instructions to: receive and/or determine the one or more channel phase adjustments.

In some embodiments, to generate the plurality of unmixed images, the processor is programmed by the executable instructions to: generate a vector comprising complex values of corresponding pixels of the plurality of phase-adjusted images; multiply the vector with the unmixing matrix to generate an unmixed vector comprising unmixed complex values; and generate the plurality of unmixed images comprising the corresponding pixels with the unmixed complex values. The vector can have a size of $1 \times n_1$, the unmixing matrix can have a size of $n_1 \times n_2$, and/or the unmixed vector can have a size of $1 \times n_2$. To generate the plurality of unmixed images, the processor can be programmed by the executable instructions to: generate the plurality of unmixed images from the plurality of phase-adjusted images using an unmixing matrix of a plurality of unmixing matrices, for corresponding pixels of the plurality of phase-adjusted images, on the complex values of the corresponding pixels. The plurality of unmixing matrices can comprise $m_2$ unmixing matrices. The unmixing matrix can comprise, or comprise only of, real values and/or complex values. The processor can be programmed by the executable instructions to: receive and/or determine the unmixing matrix.

In some embodiments, to generate the plurality of phase-corrected images, the processor is programmed by the executable instructions to: generate a phase-corrected image of the plurality of phase-corrected images from a unmixed image of the plurality of unmixed images corresponding to a fluorophore of the plurality of channels using a plurality of fluorophore phase corrections for the fluorophore of the plurality of fluorophores. The plurality of fluorophore phase corrections for the fluorophore can be related to a property of the fluorophore. The property of the fluorophore can comprise a lifetime of the fluorophore. The plurality of fluorophore phase corrections for the fluorophore can comprise complex values. The processor can be programmed by the executable instructions to: receive and/or determine the plurality of fluorophore phase corrections for the fluorophore.

In some embodiments, the processor is programmed by the executable instructions to: generate a plurality of visual representations of the plurality of phase-corrected images based on the real components of the complex values of the plurality of phase-corrected images. The processor can be programmed by the executable instructions to: generate a plurality of visual representations of the plurality of phase-corrected images based on the amplitudes of the complex values of the plurality of phase-corrected images. To determine the sorting decision, the processor can be programmed by the executable instructions to: determine the sorting decision for the cell based on the plurality of visual representations of the plurality of phase-corrected images. The processor can be programmed by the executable instructions to: generate a combined visual representation form the plurality of visual representations.

In some embodiments, the processor is programmed by the executable instructions to: generate a plurality of channels of corrected fluorescence intensity data from the plurality of phase-corrected images. To generate the plurality of channels of corrected fluorescence intensity data, the processor can be programmed by the executable instructions to: generate the plurality of channels of corrected fluorescence intensity data form the plurality of phase-corrected images using a frequency- to temporal-space transformation. The processor can be programmed by the executable instructions to: determine an estimate of a characteristic of the cell based on the plurality of channels of corrected fluorescence intensity data, wherein determining the sorting decision comprises determining the sorting decision of the cell based on the estimate of the characteristic of the cell. The characteristic of the cell can comprise a size of the cell, a ratio of sizes of the cell in two different dimensions, co-localization of fluorescence emissions by two or more of the plurality of fluorophores associated with the cell, a ratio of sizes of the cytoplasm and the nucleus of the cell, a degree of punctateness of fluorescence emission of the cell, a measure of the spatial distribution of the fluorescence emission, a measure of location or orientation of the cell, a measure of the eccentricity of the cell, a measure of the similarity of the cell to a reference cell, a measure of the degree to which the cell lies in a focal point of the laser beam, or a combination thereof.

In some embodiments, the laser beam comprises a reference laser beam and a plurality of radiofrequency-shifted laser beams. The number of the plurality of radiofrequency-shifted laser beams can be $m_2$. The reference laser beam can spatially overlap the plurality of radiofrequency-shifted laser beams. None of the plurality of radiofrequency-shifted laser beams spatially overlaps with one another. The reference laser beam and one or more of the plurality of radiofrequency-shifted laser beams can be capable of eliciting the fluorescence emission of a fluorophore of the plurality of fluorophores. Illuminating the cell can comprise illuminating a plurality of spatial locations of the cell with the plurality of radiofrequency-shifted laser beams concurrently. None of the plurality of spatial locations of the cell overlaps with one another.

In some embodiments, the number of the plurality of raw images, the number of the plurality of phase-adjusted images, the number of the plurality of unmixed images, and the number of the plurality of phase-corrected images are identical. The number of the plurality of raw images, the number of the plurality of phase-adjusted images, the number of the plurality of unmixed images, and/or the number of the plurality of phase-corrected images can be $n_1$. The plurality of raw images can be associated with a first temporal dimension and a first frequency dimension. The plurality of phase-adjusted images can be associated with a second temporal dimension and a second frequency dimension. The plurality of unmixed images can be associated with a third temporal dimension and a third frequency dimension. The plurality of phase-corrected images can be associated with a fourth temporal dimension and a fourth frequency dimension. Two or more of the first temporal dimension, the second temporal dimension, the third temporal dimension, and the fourth temporal dimension can have an identical size and/or an identical number of pixels along the dimension. The first temporal dimension, the second temporal dimension, the third temporal dimension, and the fourth temporal dimension can have the identical size and/or the identical number of pixels. The first frequency dimension, the second frequency dimension, the third frequency dimension, and/or the fourth frequency dimension can have a size of $m_2$ and/or $m_2$ pixels. In some embodiments, $m_2$ equals to $\frac{1}{2} * m_1$. In some embodiments, $m_2$ is smaller than $\frac{1}{2} * m_1$. One or more of the first frequency dimension, the second frequency dimension, the third frequency dimension, and the fourth frequency dimension can have an identical size and/or an identical number of pixels. The first frequency dimension, the second frequency dimension, the third frequency dimension, and the fourth frequency dimension can have the identical size and/or the identical number of pixels. The size of and/or the number of pixels along the first frequency dimension, the size of and/or the number of pixels along the second frequency dimension, the size of and/or the number of pixels along the third frequency dimension, and/or the size of and/or the number of pixels of the fourth frequency dimension can be identical to the number of the plurality of radiofrequency-shifted laser beams. The pixels along the first frequency dimension, the pixels along the second frequency dimension, the pixels along the third frequency dimension, and/or the pixels along the fourth frequency dimension can correspond to the plurality of radiofrequency-shifted laser beams. The pixels along the first frequency dimension, the pixels along the second frequency dimension, the pixels along the third frequency dimension, and/or the pixels along the fourth frequency dimension can correspond to the plurality of spatial locations of the cell.

In some embodiments, the fluorescence emissions of two of the plurality of fluorophores overlap spectrally. The fluorescence emissions of three of the plurality of fluorophores overlap spectrally. The fluorescence emissions of five of the plurality of fluorophores overlap spectrally. The fluorescence emissions of a first fluorophore and a second fluorophore of the plurality of fluorophores overlap spectrally, and the fluorescence emissions of the second fluorophore and a third fluorophore of the plurality of fluorophores overlap spectrally. The fluorescence emissions of the first fluorophore and the third fluorophore overlap spectrally.

Further understanding of various aspects of the invention can be obtained by reference to the following detailed description in conjunction with the associated drawings, which are described briefly below.

BRIEF DESCRIPTION OF THE DRAWINGS

FIG. 6 schematically depicts an absorption curve corresponding to the hypothetical fluorophore of FIG. 5.

FIG. 13A schematically depicts illumination of a sample by a top-hat profiled beam at a single excitation frequency.

FIG. 15 schematically depicts hypothetical fluorescence time-frequency waveforms corresponding to two channels and their product used in the method shown in the flow chart of FIG. 16

FIG. 26A-26B are composite images showing non-limiting exemplary results of spectral unmixing.

FIGS. 28B1-28B2 is a schematic illustration of performing spectral unmixing with a non-square unmixing matrix and determining a non-square unmixing matrix.

DETAILED DESCRIPTION

Figure 1:
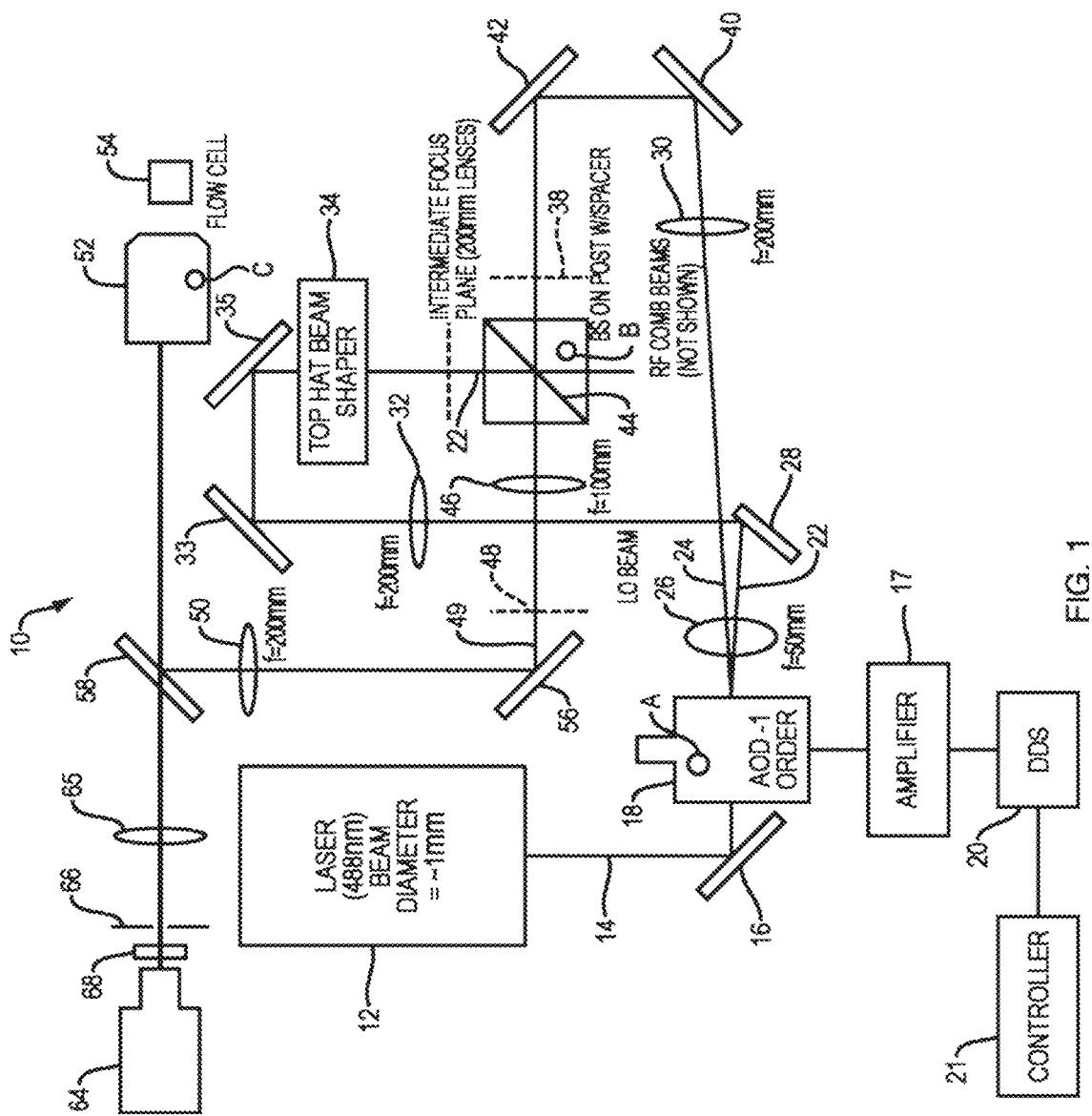
FIG. 1 schematically depicts a system in accordance with an embodiment of the invention.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

The present teachings relate generally to methods and systems for determining one or more characteristics of particles, such as cells, in a flow cytometer, and using those characteristics in some embodiments for sorting the particles. In embodiments discussed below, the methods employ computer processors for their implementation. Various terms used below to describe the present teachings have their ordinary meaning in the art, unless stated otherwise. For example, the term "fluorophore" is used herein consistent with its customary meaning in the art to refer to a fluorescent chemical compound that can emit radiation in response to illumination by excitation radiation.

The terms "cytometry" and "flow cytometry" are also used consistent with their customary meanings in the art. In particular, the term "cytometry" can refer to a technique for identifying and/or sorting or otherwise analyzing cells. The term "flow cytometry" can refer to a cytometric technique in which cells present in a fluid flow can be identified, and/or sorted, or otherwise analyzed, e.g., by labeling them with fluorescent markers and detecting the fluorescent markers via radiative excitation. The terms "about" and "substantially" as used herein to denote a maximum variation of 10%, or 5%, with respect to a property including numerical values.

The teachings of the present invention for determining characteristics of particles, such as cells, and sorting the particles can be implemented in a variety of different ways. The fluorescence and/or scattering data employed for making sorting decisions can be obtained by using a variety of systems. In some embodiments, the particle is illuminated by an optical beam having a plurality of radiofrequency-shifted beamlets and the fluorescence from the particle is collected and analyzed according to the present teachings to make a sorting decision. Some examples of such systems for eliciting fluorescence data from particles in which the present teachings can be incorporated are described below followed by detailed description of methods and systems for sorting particles according to the present teachings.

By way of example, FIG. 1 schematically depicts a system 10 for performing cytometry in which the present teachings for sorting particles can be incorporated. The system 10 can be operated in three operational modes. As discussed in more detail below, in one operational mode, a sample under study can be illuminated concurrently with a plurality of excitation frequencies, each of which can be obtained, e.g., by shifting the central frequency of a laser beam. More specifically, a plurality of sample locations can be concurrently illuminated by a laser beam that is generated by mixing a reference laser beam (herein also referred to as a local oscillator beam) with a plurality of radiofrequency-shifted laser beams such that each sample location is illuminated by the reference beam and one of the radiofrequency-shifted beams to excite a fluorophore of interest at that location, if present. In some embodiments, the reference beam can itself be generated via radiofrequency shifting of a laser beam. Thus, each spatial location of the sample can be "tagged" with a different beat frequency corresponding to a difference between the frequency of the reference beam and that of one of the radiofrequency-shifted beams. In other words, the fluorescence radiation emitted by the fluorophore will spatially encode the beat frequencies. The fluorescence emission can be detected and its frequency components can be analyzed to construct a fluorescence image of the sample. Detecting the fluorescence radiation emitted by the fluorophore after excitation by the reference beam and the radiofrequency-shifted beams can be referred to as fluorescence imaging using radiofrequency-multiplexed excitation (FIRE).

In another operational mode, a sample can be illuminated successively over a time interval by a laser beam at a plurality of excitation frequencies. In some such embodiments, the excitation frequencies can be obtained by applying a time-varying drive signal to an acousto-optic deflector (AOD), which receives a laser beam. In many embodiments, the laser beam has a frequency in the hundreds of terahertz (THz) range, e.g., in a range of about 300 THz to about 1000 THz. The drive signal applied to the AOD is typically in the radiofrequency range, e.g., in a range of about 10 MHz to about 250 MHz. The passage of the laser beam through the AOD generates a plurality of diffracted beams, each corresponding to a different diffraction order. While the zeroth diffracted beam exhibits no frequency shift relative to the frequency of the input laser beam, the higher-order diffracted beams exhibit a frequency shift relative to the frequency of the input laser beam corresponding to the frequency of the drive signal or a multiple thereof. In some embodiments, the first order diffracted beam having a frequency corresponding to the frequency of the input laser beam shifted by the drive signal is employed as the excitation beam for exciting a fluorophore of interest, if present in a sample under analysis. As the drive signal varies over time, the frequency and angular shift of the first-order diffracted beam also varies, thereby allowing the illumination of the sample at different excitation frequencies at different locations. The fluorescence emission, if any, from each illuminated location can be collected and analyzed to construct a fluorescence image of the sample.

In yet another operational mode, the system 10 can be operated to illuminate a plurality of locations of a sample concurrently by a single excitation frequency, which can be generated, e.g., by shifting the central frequency of a laser beam by a radiofrequency. For example, a horizontal extent of the sample can be illuminated by a laser beam at a single excitation frequency. The detected fluorescence radiation can be used to analyze the fluorescence content of the sample, e.g., a cell/particle.

Thus, one advantage of system 10, among others discussed below, is that it provides significant flexibility in obtaining fluorescence emission data in different modes without a need to utilize different instruments or to make any mechanical modifications to the system when switching between different operational modes.

In certain embodiments, systems include one or more light sources. In some instances, the light source is a narrow band light source, including but not limited to a narrow wavelength LED, laser or a broadband light source coupled to one or more optical bandpass filters, diffraction gratings, monochromators or any combination thereof which in combination produces a narrow band of illuminating light. In certain instances, the light source is a single wavelength laser, such as a single wavelength diode laser (e.g., a 488 nm laser). In some embodiments, the subject systems include a single light source (e.g., a laser). In other embodiments, the subject systems include two or more different light sources, such as 3 or more different light sources, such as 4 or more different light sources and including 5 or more different light sources. For example, systems may include a first light source (e.g., a laser) outputting a first wavelength and a second light source outputting a second wavelength. In other embodiments, systems include a first light source outputting a first wavelength, a second light source outputting a second wavelength and a third light source outputting a third wavelength.

Each light source may have a wavelength which ranges from 300 nm to 1000 nm, such as from 350 nm to 950 nm, such as from 400 nm to 900 nm and including from 450 nm to 850 nm. In certain embodiments, the light source has a wavelength that corresponds to an absorption maximum of one or more fluorophores (as described below). For example, the light source may output light having a wavelength that is in the range of one or more of 280-310 nm, 305-325 nm, 320-350 nm, 340-375 nm, 370-425 nm, 400-450 nm, 440-500 nm, 475-550 nm, 525-625 nm, 625-675 nm and 650-750 nm. In certain embodiments, each light source outputs light having a wavelength that is selected from 348 nm, 355 nm, 405 nm, 407 nm, 445 nm, 488 nm, 640 nm and 652 nm.

The system 10 includes a laser radiation source 12 generating a laser beam 14. By way of example, the laser beam can have a frequency in a range of about 1000 THz to about 300 THz, corresponding to a vacuum wavelength in a range of about 300 nm to about 1000 nm. The beam diameter of the laser beam (e.g., the beam waist when a Gaussian laser beam is employed) can be, for example, in a range of about 0.1 mm to about 10 mm. Without any loss of generality, in this embodiment the laser 12 emits radiation at a wavelength of 488 nm with a beam diameter of about 1 mm.

The frequency of the laser beam can be selected based on a particular application(s) for which the system is intended. Specifically, as discussed in more detail below, the laser frequency can be suitable for exciting an electronic transition of a fluorophore of interest, e.g., via absorption of the radiation, so as to cause the fluorophore to emit fluorescence radiation at a lower frequency. A variety of laser sources can be employed. Some examples of such laser sources include, without limitation, Sapphire 488-SF, marketed by Coherent, Inc. of Santa Clara, Calif. U.S.A., Genesis MX-488-1000-STM (Coherent, Inc.), OBIS 405-LX (Coherent, Inc.), Stadus 405-250 marketed by Vortran Laser Technology, Inc. of Sacramento, Calif. USA, and LQC-660-110 of Newport Corporation of Irvine, Calif. U.S.A. Without any loss of generality, in the present embodiment the laser beam is assumed to have a Gaussian intensity profile in a plane perpendicular to its propagation direction.

A mirror 16 receives the laser radiation beam 14 and directs the laser beam via reflection to an acousto-optic deflector (AOD) 18. In this embodiment, the AOD 18 is mounted on an adjustable post holder mount (A) that allows rotation of the AOD about an axis perpendicular to the propagation direction of the beam 14. A direct digital synthesizer (DDS) 20 operating under control of a controller 21 can apply one or more drive signals to the AOD 18. By way of example, in some embodiments, these drive signals can span a frequency range of about 50 MHz to about 250 MHz. For example, the drive signals applied to the AOD may range from about 55 MHz to about 255 MHz, such as from about 60 MHz to about 200 MHz, such as from about 65 MHz to about 175 MHz, such as from about 70 MHz to about 150 MHz and including from about 75 MHz to about 125 MHz. In some embodiments, the drive signals may be separated from one another by a frequency in a range of about 0.1 MHz to about 4 MHz. For example, the drive signals may be separated from one another by a frequency of from about 0.2 MHz to about 3.9 MHz, such as from about 0.3 MHz to about 3.8 MHz, such as from about 0.4 MHz to about 3.7 MHz, such as from about 0.5 MHz to about 3.6 MHz and including from about 1 MHz to about 3.5 MHz. In this embodiment, an electronic power amplifier 17 amplifies the radiofrequency signals generated by the DDS 20 for application to the AOD 18.

In the operational mode in which a sample is illuminated concurrently with a plurality of excitation frequencies, the RF comb generator 20 applies a plurality of RF drive signals concurrently to the AOD 18. By way of example, the number of simultaneously applied RF drive signals can be in a range of about 20 to about 200. The interaction of the laser beam and the drive signals results in generation of a plurality of angularly separated laser beams each having a frequency shift corresponding to one of the drive signals relative to the frequency of the laser beam generated by the laser 12. Without being limited to any particular theory, in an AOD, a piezoelectric transducer can generate radiofrequency phonons in a crystal, e.g., a quartz crystal, and the scattering of the optical photons of the laser beam by such radiofrequency phonons can result in the generation of the frequency-shifted laser beams. One of these frequency-shifted beams 22 is herein referred to as a "local oscillator" (LO) beam and the remainder of the frequency shifted beams 24 are herein referred to as "RF comb beams." The angular separation of the frequency shifted beams can be, for example, in a range of about 1 milliradians to about 100 milliradians. For example, the angular separation of the frequency shifted beams may range from 2 milliradians to about 95 milliradians, such as from 3 milliradians to about 90 milliradians, such as from 4 milliradians to about 85 milliradians, such as from 5 milliradians to about 80 milliradians and including from 10 milliradians to about 75 milliradians.

The LO and the RF comb beams pass through a lens 26, which is in this embodiment a positive lens with a focal length of about 50 mm. After passage through the lens 26, the LO laser beam is intercepted by a mirror 28, which redirects the LO beam in a different direction (in this embodiment in a direction substantially orthogonal to the original propagation direction of the LO beam). The mirror 28 is positioned relative to the RF comb beams such that these beams miss the mirror 28 and propagate to a lens 30 (which in this embodiment has a focal length of 200 mm). In this manner, the LO beam and the RF comb beams are directed along different propagation directions. The use of the pickoff mirror 28 in a manner disclosed above allows utilizing a single AOD to generate both the LO beam and the RF comb beams and combining them in a manner discussed below to generate an excitation beam for illuminating a sample. The use of a single AOD, rather than multiple AODs (e.g., two AODs, one for generating the LO beam and the other for generating the RF comb beams), simplifies the design of the system and further allows efficient use of the system in multiple distinct operational modes, as discussed in more detail below.

In some embodiments, the beam profile of the LO beam is modified before recombining with the RF comb beams. For example, the beam profile of the LO beam may be adjusted (increased or decreased) in spatial dimension, beam shape, intensity, spatial distribution of beam, or any combination thereof. In certain embodiments, the spatial dimensions of the beam profile of the LO beam are modified. For example, the beam profile may be adjusted to elongate the beam profile in one or more dimensions, such as along an axis that is orthogonal to the longitudinal axis of a flow stream. In one example according to these embodiments, the spatial dimension (e.g., in one or more dimensions) of the beam profile may be increased by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more. In another example according to these embodiments, the spatial dimension (e.g., in one or more dimensions) of the beam profile may be decreased by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more.

In other embodiments, the beam shape of the LO beam is modified. For example, the beam shape may be modified to elongate the beam profile in one or more dimensions. In certain instances, the beam shape of the LO beam is elongated in a plane perpendicular to the propagation direction of the LO beam. In certain embodiments, the shape of the LO beam profile is changed from a circular beam profile to an oval beam profile that is elongated in an axis orthogonal to the longitudinal axis of the flow stream. In other embodiments, the shape of the LO beam profile is changed from a circular beam profile to a rectangular beam profile that has a long dimension in an axis orthogonal to the longitudinal axis of the flow stream. In still other embodiments, the intensity of the LO beam is modified. For example, the intensity of the LO beam may be increased, such as by 1% or more, such as by 2% or more, such as by 3% or more, such as by 5% or more, such as by 10% or more, such as by 25% or more, such as by 50% or more, such as by 75% or more, such as by 90% or more, such as by 1.5-times or more, such as by 2-times or more, such as by 3-times or more and including by 5-times or more. In certain embodiments, the intensity of the LO beam is modified to match the intensity of the RF comb beam. For example, the LO beam may have an intensity that differs from the intensity of the RF comb beams by 10% or less, such as by 9% or less, such as by 8% or less, such as by 7% or less, such as by 6% or less, such as by 5% or less, such as by 4% or less, such as by 3% or less, such as by 2% or less, such as by 1% or less, such as by 0.01% or less and including where the intensity of the LO beam differs from the RF comb beams by 0.001% or less. In certain instances, the intensities of the LO beam and the RF comb beams are identical.

In yet other embodiments, the spatial distribution of the beam profile may also be modified. For example, the LO beam may be modified such that the intensity of the LO beam is no longer Gaussian in one or more dimensions. For example, the LO beam may be modified to have a Gaussian distribution along a first axis that is parallel to the longitudinal axis of the flow stream and non-Gaussian along a second axis that is orthogonal to the longitudinal axis of the flow stream.

Any beam shaping protocol may be employed to modify the beam profile of the LO beam, including but not limited to refractive and diffractive beam shaping protocols. In some embodiments, the LO beam is modified by a top-hat beam shaper.

In this embodiment, the LO beam propagates to another positive lens 32 (which in this embodiment has a focal length of about 200 mm). The combination of the lens 26 and the lens 32 magnifies and collimates the LO beam in order to appropriately fill the back aperture of a top-hat beam shaper 34. More specifically, the LO beam 22 passes through the lens 32 and is reflected by mirrors 33 and 35 to the top-hat beam shaper 34.

The top-hat beam shaper 34 shapes the phase front of the Gaussian LO beam to enable formation of a top-hat intensity profile. More specifically, the LO laser beam 22' exiting the top-hat beam shaper is reflected by a beam splitter 44 and is focused by lens 46 (which in this embodiment has a focal length of 100 mm) onto an intermediate image plane 48. The laser beam on the intermediate image plane 48 has a top-hat intensity profile along a horizontal direction in a plane perpendicular to the propagation direction of the beam. Similar to the AOD 18, in this embodiment, the beam splitter 44 is mounted on an adjustable post holder mount (B). In this embodiment, the top-hat beam shaper generates a top-hat beam profile in which the polarization of radiation is substantially uniform along the top-hat direction of the beam (along the horizontal direction in this embodiment).

A variety of top-hat beam shapers can be employed. By way of example, refractive optical elements having an aspherical surface or diffractive optical elements can be used to produce beams with appropriate spatial phase fronts, which, after focusing by a lens, will produce a top hat profile pattern at the focal plane of the lens. Multiple form factors exist for such top-hat beam shapers, and a variety of implementations of this approach are available to create the appropriate LO beam shape at the sample in various embodiments of the present teachings. For example, U.S. Pat. No. 6,295,168 entitled "Refractive optical system that converts a laser beam to a collimated flat-top beam" and U.S. Pat. No. 7,400,457 entitled "Rectangular flat-top beam shaper," both of which are herein incorporated by reference in their entirety, disclose beam shaping systems that can be employed as the flat-top beam shaper in a system according to some embodiments of the present teachings. An example of a commercially available top-hat beam shaper that can be employed include, for example, DTH-1D-0.46deg-4 mm marketed by Osela, Inc. of Lachine, Canada.

As discussed in more detail below, the use of a beam shaper to stretch the LO beam along the horizontal direction provides a number of advantages. For example, it can ensure that the combination of the LO beam and the RF comb beams illuminates a plurality of sample locations with a substantially similar illumination intensity, in order to match the intensities of the LO and RF comb beams across the entirety of the sample locations, thereby creating an intensity amplitude modulation of the fluorescence signal with high modulation depth. In absence of such intensity matching, the imaging system may have a small view and may not utilize all of the frequencies (pixels) driving the AOD. As the modulation depth of the fluorescence signal plays an important role in the ability of the system to reconstruct a fluorescence image of the sample, a uniformly-high modulation depth of the excitation beat frequencies at all pixels is particularly advantageous to the operation of the system. Further, the amplitudes of electronic signals applied to the AOD for generating the RF comb beams can be adjusted by controlling the output of the direct digital synthesizer (e.g., by employing the controller 21) in order to equalize the RF comb beams such that their intensities are equal to that of the LO beam across all spatial locations in which the RF comb beams and the LO beam overlap. This feature provides an advantage in that it ensures high modulation depth of the intensity amplitude modulation of the fluorescence radiation.

Referring again to FIG. 1, the RF comb beams 24 are imaged via the combination of the lenses 26 and 30 onto an intermediate image plane 38. More specifically, the RF comb beams 24 pass through the lens 26 and miss the mirror 28 to reach the lens 30, which directs the RF comb beams via mirrors 40 and 42 to the intermediate image plane 38.

Figure 2:
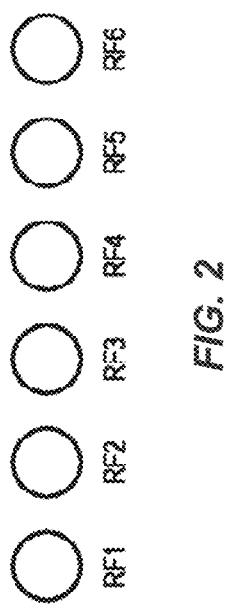
FIG. 2 schematically depicts cross-sectional beam profiles of a plurality of RF comb beams.

FIG. 2 schematically depicts the distribution of an exemplary number of RF comb beams in the intermediate image plane 38 (without loss of generality, the number of RF comb beams is selected to be 6 for illustration purposes (labeled as RF1, RF2, RF3, RF4, RF5, RF6), though other numbers can also be employed). As shown in FIG. 2, in the intermediate image plane 38, the RF comb beams 24 are spatially separated from one another along the horizontal direction. In other embodiments, two or more of the RF comb beams 24 may partially overlap. Thus, the combination of the lenses 26 and 30 transforms the angularly separated RF comb beams into a set of spatially separated beams that span over a horizontal extent.

Referring again to FIG. 1, as discussed above, the beam splitter 44 receives the laser beam 22' exiting the top-hat beam shaper 34 and reflects that beam to lens 46, which in turn focuses the beam on the intermediate image plane 48 in which the LO beam exhibits a top-hat beam profile. The beam splitter also receives the RF comb beams 24 from the intermediate image plane 38 and allows the passage of the RF comb beams there through. The lens 46 focuses the RF comb beams 24 onto the intermediate image plane 48 to be combined with the LO beam having a top-hat beam profile to generate a combined beam 49.

Figure 3:
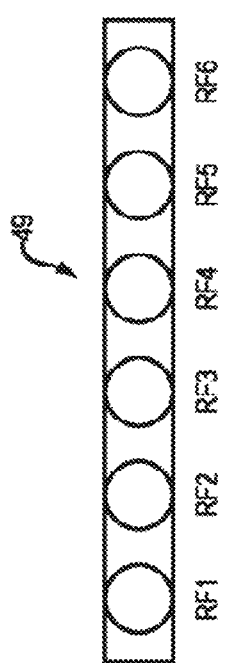
FIG. 3 schematically depicts superposition of the RF comb beams depicted in FIG. 2 and an LO beam having a top-hat beam profile.

By way of illustration, FIG. 3 schematically depicts one exemplary profile of the combined beam 49 in a plane perpendicular to its propagation axis. The intensity profile of the combined beam is generated as a superposition of the intensity profile of the top-hat LO beam (shown schematically by the square) and those of the RF comb beams 24 (each shown schematically by one of the circles). As discussed in more detail below, this superposition of the LO beam and the RF comb beams provides, along a horizontal extent, a plurality of beat frequencies each corresponding to one spatial location along that horizontal extent. Upon illuminating a horizontal extent of a sample, the fluorescence radiation emitted from a location of the sample encodes, via amplitude modulation, the beat frequency associated with radiation illuminating that location.

Referring again to FIG. 1, a positive lens 50 (200-mm lens in this embodiment) and an objective lens 52, mounted in this embodiment on an adjustable post holder mount C, form a telescope for relaying the image at the intermediate plane 48 onto a sample flowing through a flow cell 54. In this embodiment, a mirror 56 reflects the combined beam 49 to the lens 50, and a dichroic mirror 58 reflects the combined light beam after its passage through the lens 50 toward the objective lens 52.

Figure 4:
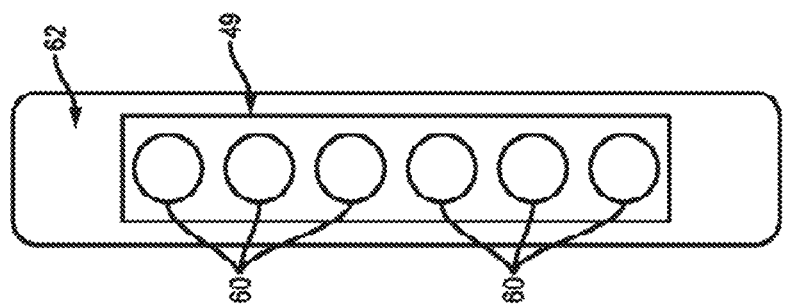
FIG. 4 schematically depicts the combined beam shown in FIG. 3 illuminating a sample under analysis.

As shown schematically in FIG. 4, the combined beam 49 concurrently illuminates a plurality of spatial locations 60 of a sample 62 flowing through the flow cell 54. Thus, each location 60 is illuminated by the overlap of one of the RF comb beams with a portion of the top-hat shaped LO laser beam. At these spatial locations, the radiation will excite a fluorophore of interest in the sample, if present. More specifically, in this embodiment, the LO beam and the RF comb beams excite concurrently the fluorophore, e.g., via causing electronic transition thereof to an excited electronic state, at a plurality of sample locations 60.

In some embodiments, the sample can include a flowing fluid, in which a plurality of cells are entrained. In some cases, the cells can be labeled with one or more fluorescent markers (fluorophores). Some examples of fluorescent markers include, without limitation, fluorescent proteins (e.g., GFP, YFP, RFP), antibodies labeled with fluorophores (e.g., fluorescein isothiocyanate) (FITC), phycoerythrin (PE), allophycocyanin (APC)), nucleic acid stains (e.g., 4', 6-diamidino-2-phenylindole (DAPI), SYTO16, propiedium iodide (PI)), cell membrane stains (e.g., FMI-43), and cell function dyes (e.g., Fluo-4, Indo-1). In other cases, endogenous fluorophores present in cells can be employed to elicit fluorescent radiation from the cells. As discussed in more detail below, such exogenous or endogenous fluorophores undergo electronic excitation in response to the illuminating radiation and emit fluorescent radiation (typically at a lower frequency than the excitation frequency), which is collected and analyzed.

Figure 5:
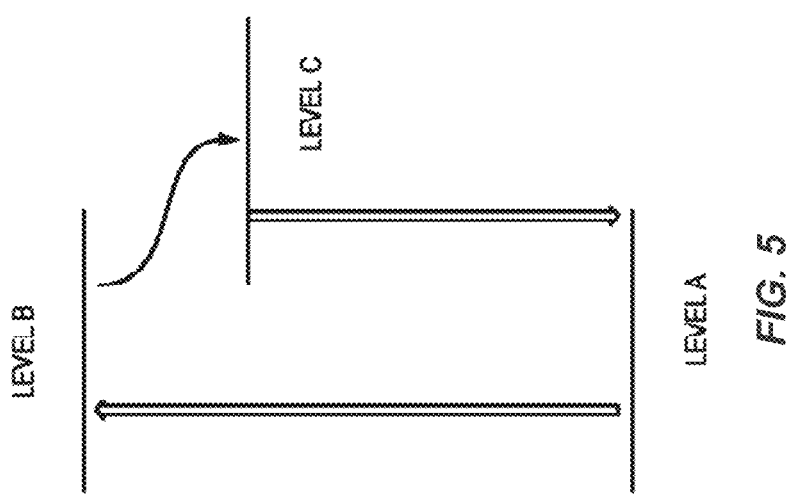
FIG. 5 schematically depicts exemplary energy levels of a hypothetical fluorophore.

By way of illustration and without being limited to any particular theory, FIG. 5 shows hypothetical energy levels corresponding to a ground electronic state A as well as two electronic excited electronic states B and C of a fluorophore. The fluorophore can be excited from its ground electronic state (A) to the excited electronic state (B) via absorption of radiation energy. The fluorophore can then relax into the lower excited state B, e.g., via a radiation-less transition mediated by vibrational modes of the fluorophore. The fluorophore can further relax from the lower electronic state C to the ground state, via an optical transition, thereby emitting fluorescence radiation at a frequency less than that of the excitation frequency. It should be understood that this hypothetical example is provided only for illustration purposes, and not to indicate the only mechanism by which fluorescence radiation can be emitted.

In many cases, the fluorophore can absorb electromagnetic radiation over a range of frequencies to be excited from the ground state to the excited electronic state. By way of illustration, FIG. 6 shows an absorption curve for the hypothetical fluorophore discussed in connection with FIG. 5. In one implementation of an embodiment according to the present teachings the LO frequency can be selected to coincide with the frequency corresponding to the peak absorption of a fluorophore of interest. The radiofrequency-shifted beams can have frequencies separated from the peak absorption by their respective beat frequencies. Typically, these frequency separations are small in comparison to the absorption bandwidth of the fluorophore so as to avoid any degradation of the excitation frequency. By way of example and only by way of illustration, the dashed lines A and B schematically depict the frequency of the LO beam and one of the RF comb beams (the figures is not drawn to scale for ease of description). The concurrent illumination of a spatial location of the sample by both the LO laser beam and one of the depicted RF comb beams results in fluorescence radiation exhibiting an amplitude modulation at a beat frequency corresponding to a difference between the LO and the RF comb beam frequencies.

Again by way of illustration and without being limited to any particular theory, the electric field applied to the fluorophore via its concurrent illumination by the LO beam and one of the RF comb beams can be mathematically defined as follows:

$$E_{com}=E_{RF}e^{j(\omega 0+\omega RF)}+E_{LO}e^{j(\omega 0+\omega LO)} \quad \text{Eq. (1)}$$

where $E_{com}$ denotes the electric field of the combined beam,
$E_{RF}$ denotes the amplitude of the electric field associated with one of the RF comb beams,
$E_{LO}$ denotes the amplitude of the electric field associated with the LO beam,
$\varphi_0$ denotes the frequency of the laser beam generated by the laser 12,
$\varphi_{RF}$ denotes the frequency shift associated with the RF comb beam, and
$\varphi_{LO}$ cow denotes the frequency shift associated with the LO beam.

The intensity of the fluorescence radiation emitted in response to the superposition of the electric fields of the LO and RF comb beams would exhibit a modulation at a beat frequency corresponding to ($\omega_{RF}-\omega_{LO}$). Hence, the fluorescence radiation emanating from each spatial location of the sample illuminated by superposition of the LO beam and one of the RF comb beams exhibits a modulation at a beat frequency corresponding to the difference between the radiofrequency shift associated with the LO beam and that associated with the RF comb beam illuminating that spatial location.

As the process of fluorescence emission requires a finite amount of time (typically 1-10 nanoseconds for common organic fluorophores), the emitted fluorescence will not exhibit a high modulation depth if the excitation beat frequency is too high. Thus, in many embodiments, the excitation beat frequencies are selected to be considerably less than $1/\tau_f$, where $\tau_f$ is the characteristic fluorescence lifetime of the fluorophore. In some instances, the excitation beat frequencies may be less than $1/\tau_f$ by 1% or more, such as by 2% or more, such as by 3% or more, such as by 5% or more, such as by 10% or more, such as by 25% or more, such as by 50% or more, such as by 75% or more, such as by 90% or more, such as by 1.5-times of more, such as by 2-times or more, such as by 3-times or more and including by 5-times or more. For example, the excitation beat frequencies may be less than $1/\tau_f$ by 0.01 MHz or more, such as by 0.05 MHz or more, such as by 0.1 MHz or more, such as by 0.5 MHz or more, such as by 1 MHz or more, such as by 5 MHz or more, such as by 10 MHz or more, such as by 25 MHz or more, such as by 50 MHz or more, such as by 100 MHz or more, such as by 250 MHz or more, such as by 500 MHz or more and including 750 MHz or more. In some embodiments, the photodetector is configured to detect light (e.g., luminescence such as fluorescence) from the irradiated sample. In some embodiments, the photodetector may include one or more detectors, such as 2 or more detectors, such as 3 or more detectors, such as 4 or more detectors, such as 5 or more detectors, such as 6 or more detectors, such as 7 or more detectors and including 8 or more detectors. Any light detecting protocol may be employed, including but not limited to active-pixel sensors (APSs), quadrant photodiodes, image sensors, change-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combination thereof, among other photodetectors. In some embodiments, photodetectors of interest are configured to detect light that ranges from 350 nm to 1200 nm, such as from 450 nm to 1150 nm, such as from 500 nm to 1100 nm, such as from 550 nm to 1050 nm, such as from 500 nm to 1000 nm and including from 400 nm to 800 nm. In certain embodiments, the photodetector is configured to detect light at the emission maximum of the luminescence, such as at 395 nm, 421 nm, 445 nm, 448 nm, 452 nm, 478 nm, 480 nm, 485 nm, 491 nm, 496 nm, 500 nm, 510 nm, 515 nm, 519 nm, 520 nm, 563 nm, 570 nm, 578 nm, 602 nm, 612 nm, 650 nm, 661 nm, 667 nm, 668 nm, 678 nm, 695 nm, 702 nm, 711 nm, 719 nm, 737 nm, 785 nm, 786 nm, or 805 nm.

In some embodiments, the fluorescence radiation emitted by the sample can be collected in a variety of different ways, e.g., along an optical path that is perpendicular to the propagation direction of the excitation beam. In other embodiments, the fluorescence radiation is detected in an epi-direction. Detecting the fluorescence radiation emitted by one or more fluorophores after excitation by the combined beam 49 can be referred to as fluorescence imaging using radiofrequency-multiplexed excitation (FIRE).

Referring again to FIG. 1, in this embodiment, the fluorescence radiation emitted by one or more fluorophores present in the illuminated sample passes through the objective lens 52 and is transmitted through the dichroic mirror 58 to reach a photodetector 64. More specifically, in this embodiment, a lens 65 focuses the fluorescent radiation transmitted through the dichroic mirror 58 onto a slit aperture 66. The fluorescent radiation that is transmitted through the slit passes through a fluorescence emission filter 68 to reach the photodetector 64. The slit aperture 66 (or an optical filter in other embodiments discussed below) disposed in front of the photodetector substantially allows the passage of the fluorescence radiation emitted from a particular plane of the sample while rejecting out-of-plane fluorescence emission. Further, the fluorescence emission filter 68, e.g., a passband filter, allows the passage of fluorescence radiation to the photodetector 64 while substantially blocking the passage of radiation at other frequencies.

The photodetector 64 has sufficient RF bandwidth to detect and transmit signals from the entire range of the beat frequencies. Some examples of suitable photodetectors include, without limitation, a photomultiplier tube, avalanche photodiode, PIN photodiode, and a hybrid photodetector, among others. By way of example, in some embodiments, a photomultiplier tube marketed by Hamamatsu Corporation can be employed (e.g., R3896, R10699, H11462). The photodetector generates a signal, e.g., an analog signal in this embodiment, in response to the detection of the received fluorescence radiation.

Figure 7A:
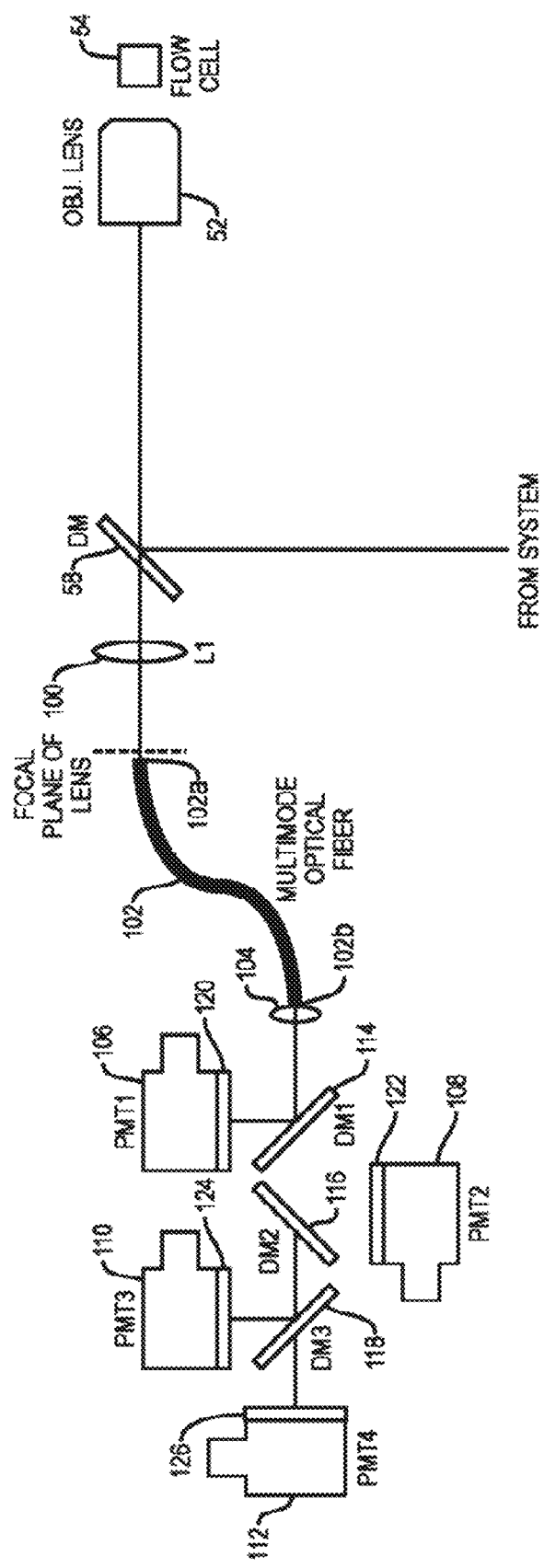
FIG. 7A schematically depicts a detection system according to an embodiment of the present teachings, which includes an optical fiber for transmission of fluorescence radiation.

By way of another example and with reference to FIG. 7A, the fluorescence radiation emitted by the sample in response to concurrent illumination by the LO beam and the spatially separated RF comb beams passes through the objective lens 52 and the dichroic mirror 58 to be coupled via a lens 100 onto a multimode optical fiber 102, which extends from a proximal end 102a to a distal end 102b. More specifically, the proximal end 102a of the optical fiber 102 is positioned in proximity of the focal plane of the lens 100 so as to receive the fluorescent radiation. An outcoupling lens 104, coupled to the distal end 102b of the optical fiber, collimates the radiation exiting the fiber.

In many cases, the excitation radiation illuminating the sample excites multiple fluorophores (e.g., organic fluorophores) that can have broad enough radiation absorption spectra such that the excitation frequencies fall within the absorption spectra of multiple fluorophores in the sample. Each fluorophore would then emit fluorescence radiation at a different frequency. Without loss of generality and for purposes of illustration, in this embodiment, the detection system includes four photomultiplier tubes 106, 108, 110 and 112, each of which receives a portion of the collimated radiation corresponding to the fluorescence radiation emitted by one of four fluorophores excited by the excitation radiation in the illuminated sample. More specifically, a dichroic mirror 114 reflects the fluorescence radiation emitted by one of the fluorophores at a first frequency to the photomultiplier tube 106 while allowing fluorescence radiation at other frequencies to pass through. Another dichroic mirror 116 reflects the fluorescence radiation emitted by a different fluorophore at a different second frequency to the photomultiplier tube 108 while allowing the rest of the radiation containing fluorescence radiation emitted by yet another fluorophore at a third frequency to reach a third dichroic mirror 118, which reflects that fluorescence radiation to the photomultiplier tube 110. The dichroic mirror 118 allows the rest of the radiation including the fluorescence radiation emitted by a fourth fluorophore at a fourth radiation frequency to pass through to reach the photomultiplier tube 112.

A plurality of bandpass filters 120, 122, 124, and 126, each centered at one of the four fluorescence frequencies, are placed in front of the photomultiplier tubes 106, 108, 110, and 112, respectively. The signal detected by each of the photomultiplier tubes is analyzed in a manner discussed below to generate a fluorescence image at the respective fluorescence frequency. In some embodiments, rather than using multiple photodetectors, a single photodetector, e.g., a single photomultiplier tube can be used to detect fluorescence radiation, e.g., fluorescence frequency corresponding to emission from a single fluorophore.

In some embodiments, as the sample flows through the flow cell different horizontal rows of the sample are illuminated and fluorescence radiation associated with each horizontal row is detected by one or more photodetectors, such as the photomultipliers 106, 108, 110 and 112.

Figure 7B:
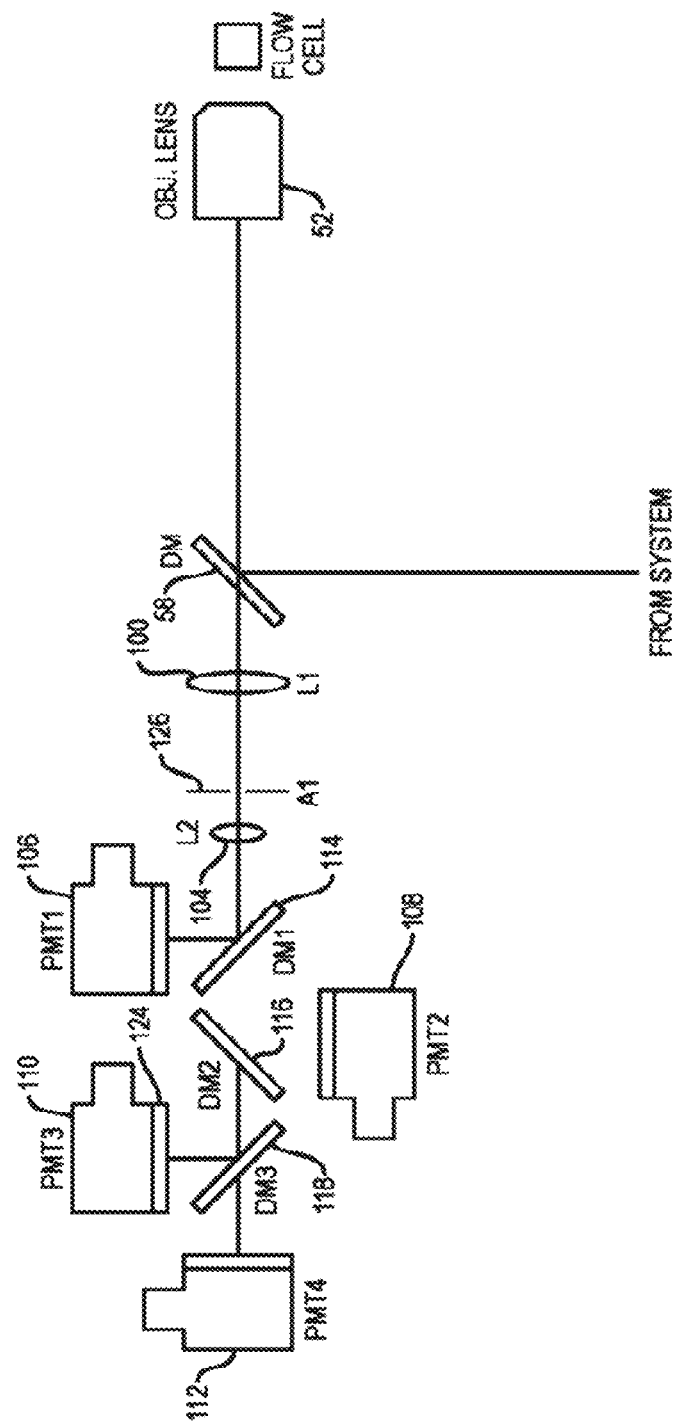
FIG. 7B schematically depicts another detection system according to an embodiment of the present teachings in which fluorescence radiation propagates through free space to reach a plurality of photodetectors.

FIG. 7B schematically depicts a detection system similar to that discussed above in connection with FIG. 7A except that this detection system, rather than using an optical fiber, the fluorescence radiation containing fluorescence emission from a plurality of fluorophores passing through the dichroic mirror 58 propagates in free space to reach the photomultiplier tubes 106, 108, and 112. More specifically, the lens 100 focuses the fluorescence radiation onto an aperture 126 disposed between the lenses 100 and 104, where the aperture can reject out-of-focus radiation. The lens 104 collimates the radiation passing through the aperture, where the collimated radiation is distributed among the photomultiplier tubes in a manner discussed above in connection with FIG. 7A.

Figure 7C:
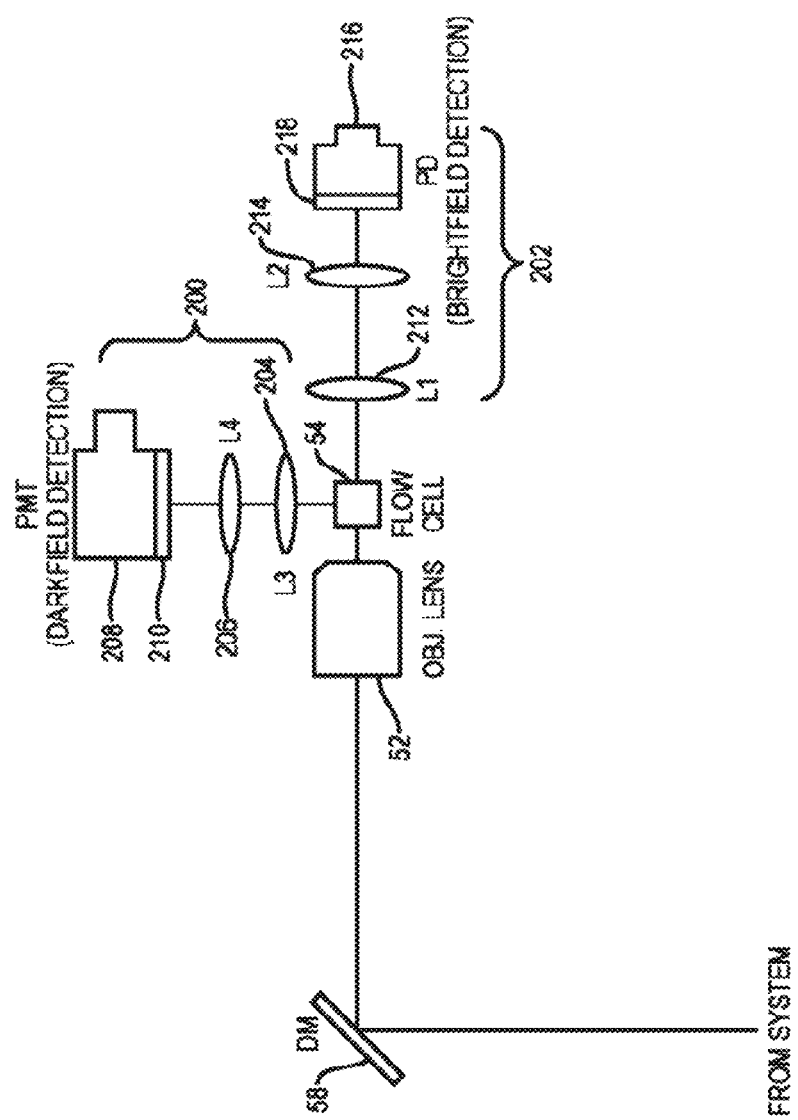
FIG. 7C schematically depicts a brightfield and a darkfield image generation arms for use in some embodiments of the present teachings.

In some embodiments, the system 10 can be configured to provide a darkfield image and a brightfield image of the sample (of the flow cell in absence of the sample) using the excitation radiation. By way of example, FIG. 7C schematically depicts an embodiment of the system 10 that includes two detection arms 200 and 202 for detecting, respectively, a darkfield image and a brightfield image of the sample.

More specifically, the detection arm 200 is positioned perpendicular to the propagation of the excitation radiation so as to receive a portion of the excitation radiation that is scattered by the sample flowing through the flow cell. The detection arm 200 includes two lenses 204 and 206 that collectively direct at least a portion of the excitation radiation scattered by the sample into a solid angle subtended by the lens 204 onto a photomultiplier tube 208. More specifically, the lens 204 collimates the received scattered radiation and the lens 206 focuses the collimated scattered radiation onto the photomultiplier tube 208. In this embodiment, an appropriate bandpass filter 210 is disposed in front of the photomultiplier tube 208 to allow the passage of radiation having the desired frequency to the photomultiplier tube 208 while blocking radiation at unwanted frequencies. The output of the photomultiplier tube 208 can be processed in a manner known in the art, e.g., by an analysis module such as that discussed below to generate a darkfield image.

The detection arm 202 in turn includes two lenses 212 and 214, where the lens 212 collimates the excitation radiation exiting the flow cell in a forward direction (substantially along the propagation direction of the excitation radiation entering the flow cell 54) and the lens 214 focuses the collimated radiation onto a photodetector 216. An appropriate filter 218, e.g., a bandpass filter, disposed in front of the photodetector allows transmission of the excitation frequencies to the photodetector 216 while substantially blocking other radiation frequencies. The output of the photodetector 216 can be processed in a manner known in the art to generate a brightfield image of the flow cell.

Thus, the detection arm 200 detects the excitation radiation that is scattered by the fluid flowing through the cell, and the detection arm 202 detects the excitation radiation that is transmitted through the flow cell. When no fluid is flowing through the flow cell, the signal detected by the photomultiplier tube 208 is low and the signal detected by the photodetector 216 is high as there is little scattering of the excitation radiation passing through the flow cell and hence a large percentage, and in some cases all, of the excitation radiation is transmitted through the flow cell. In contrast, the flow of a fluid sample through the flow cell can cause the signal generated by the photomultiplier tube 208 to increase due to scattering of a portion of the excitation radiation by the sample, and the signal generated by the photodetector 216 decreases as the level of the excitation radiation transmitted through the flow cell decreases.

Figure 7D:
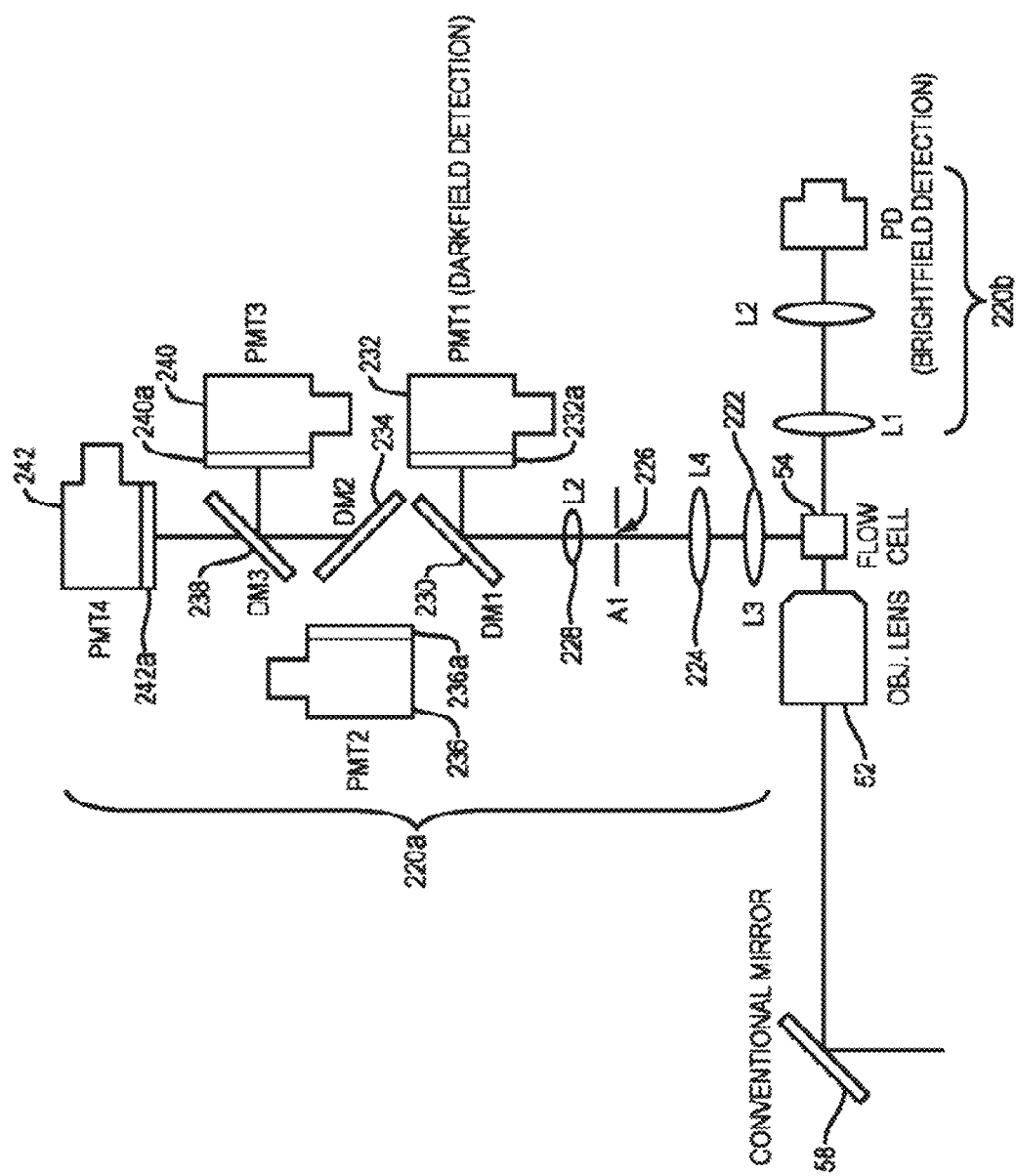
FIG. 7D schematically depicts a detection system for use in some embodiments of the present teachings, which includes a detection arm for generating a brightfield image and a detection arm which integrates the capabilities for the detection of excitation radiation scattered from a sample as well as fluorescence radiation emitted by the sample.

By way of further example and with reference to FIG. 7D, in one embodiment of a system according to the present teachings, a detection arm 220a positioned relative to the flow cell 54 in a direction substantially orthogonal to the propagation direction of the excitation radiation includes photodetectors for detecting both the fluorescence radiation emitted by a plurality of fluorophores in the sample as well as excitation radiation that is scattered by the sample. More specifically, the detection arm 220 includes lenses 222 and 224 that direct the fluorescence radiation as well as the scattered excitation radiation onto an aperture 226, which rejects unfocused radiation. A lens 228 collimates the radiation passing through the aperture. A dichroic mirror 230 reflects the portion of the radiation at the excitation frequencies onto a photomultiplier tube 232 for detection of a darkfield image while allowing fluorescence radiation to pass through. An appropriate filter 232a, e.g., a bandpass filter, disposed in front of the photomultiplier tube 232 allows the passage of radiation at excitation frequencies to the photomultiplier tube 232 while blocking unwanted radiation frequencies. Another dichroic mirror 234 reflects fluorescence radiation emitted by a fluorophore at a first frequency onto a photomultiplier tube 236 while allowing the passage of fluorescence radiation emitted by other fluorophores at other frequencies. Another dichroic mirror 238 reflects fluorescence radiation emitted by another fluorophore at a second frequency onto a photomultiplier tube 240 while allowing the passage of fluorescence radiation emitted by yet another fluorophore at a third frequency, where it is detected by the photomultiplier tube 242. Similar to the previous embodiments, a plurality of filters 236a, 240a, and 242a are disposed in front of the photomultiplier tubes 236, 240, and 242, respectively, to allow the transmission of radiation at desired frequencies while substantially blocking unwanted radiation frequencies.

With continued reference to FIG. 7D, this implementation of a system according to the present teachings further includes another detection arm 220b for generating a brightfield image, e.g., in a manner discussed in connection with FIG. 7C. More specifically, the detection arm 202 includes two lenses 212 and 214 that focus the light onto a photodetector 216 for generating a brightfield image of the excitation radiation. A filter 218, e.g., a bandpass filter, is placed in front of the photodetector 216 to allow the passage of the excitation radiation to the detector while rejecting unwanted radiation frequencies.

Figure 8:
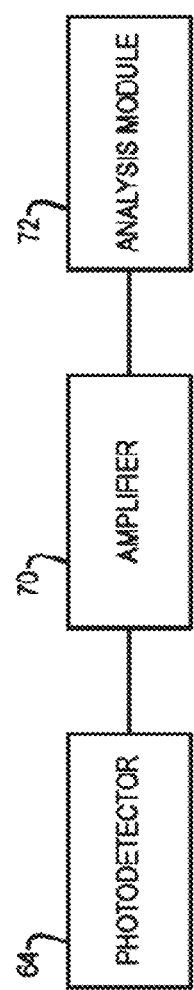
FIG. 8 schematically depicts that a fluorescence signal generated by a photodetector in an embodiment of a system according to the present invention can be amplified by an amplifier and the amplified signal can be analyzed by an analysis module to construct a fluorescence image of a sample under analysis.

Referring again to FIG. 1 as well as FIG. 8, in this embodiment, a transimpedance amplifier 70 can be coupled to the output of photodetector 64 (or each of the photodetectors discussed in connection with FIGS. 7A-7D) to amplify the signal generated by the photodetector. A data analysis unit 72 (herein also referred to as an analysis module or an analyzer) receives the amplified signal and analyzes the signal to generate a fluorescence image of the sample. The data analysis unit 72 can be implemented in hardware, firmware, and/or software. By way of example, a method for analyzing the detected fluorescence data can be stored in a read-only-memory (ROM) unit of the analysis module to be accessed under the control of a processor to analyze the received fluorescence signal.

As discussed in more detail below, the analysis method determines the frequency components of the time-varying photodetector's output and constructs a fluorescence image of the sample based on those frequency components. A variety of methods for determining the frequency content of the photodetector's output can be employed. Some examples of such suitable methods include, without limitation, Fourier transform, lock-in detection, filtering, I/Q demodulation, homodyne detection, and heterodyne detection.

Figure 9A:
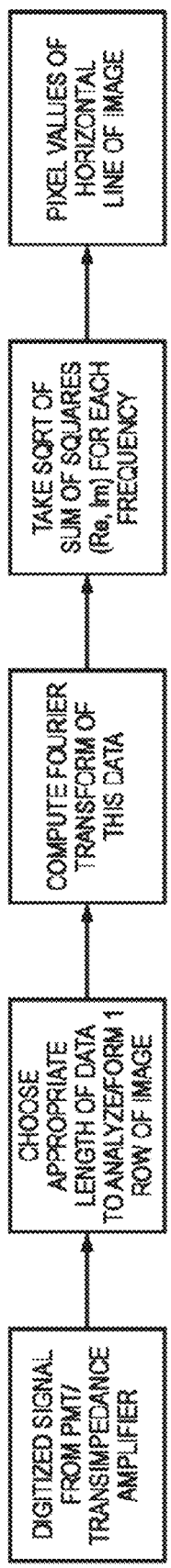
FIGS. 9A and 9B depict a method according to an embodiment of the present invention for analysis of fluorescence signal obtained by illuminating a sample with a combined beam composed of a plurality of RF comb beams and a top-hat profiled LO beam.
Figure 9B:
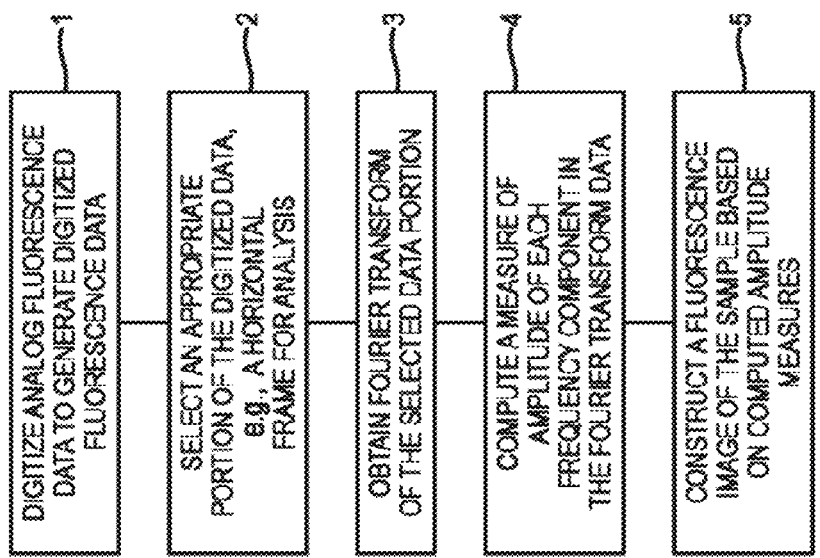

By way of example, FIGS. 9A and 9B show exemplary analysis that can be performed by the analysis module 72 to generate a fluorescence image of the sample. At block (1), the analog amplified signal is digitized to generate digitized fluorescence data. At block (2), an appropriate portion (length) of the digitized data is selected for analysis. For example, the fluorescence data corresponding to an illuminated row of the sample (herein also referred to as a frame) can be chosen for analysis. Alternatively, a portion of a data frame can be selected for analysis.

At block (3), a Fourier transform of the selected data is performed. By way of example, in some embodiments, a Fast Fourier Transform (FFT) of the data is performed to determine frequency components of the data. In some such embodiments, the bins of the FFT can correspond to the frequencies chosen for data acquisition. For example, for a 256 MHz sampling rate, 256 samples can yield frequency bins that are separated from one another by 1 MHz, e.g., from DC to 128 MHz. The FFT analysis provides frequencies corresponding to the beat frequencies at which the emitted fluorescence emission exhibits amplitude modulation.

With continued reference to FIGS. 9A and 9B, in this embodiment, at block (4), a measure of the amplitude of each frequency component present in the FFT data is computed by obtaining the square root of the sum of squares of the real and imaginary components of that frequency component. As each frequency component corresponds to one of the beat frequencies employed to elicit the fluorescence radiation from a particular location of the sample, the measure of the amplitude of the frequency component can provide a pixel value for a location associated with that frequency component along a horizontal row of the sample. In this manner, pixel values for an image of a horizontal row of the sample can be determined. The above blocks can be repeated for fluorescence data obtained for each horizontal row of the sample as the sample flows through the flow cell in a vertical direction. The pixels values can be used to construct a fluorescence image (block 5).

Figure 10:
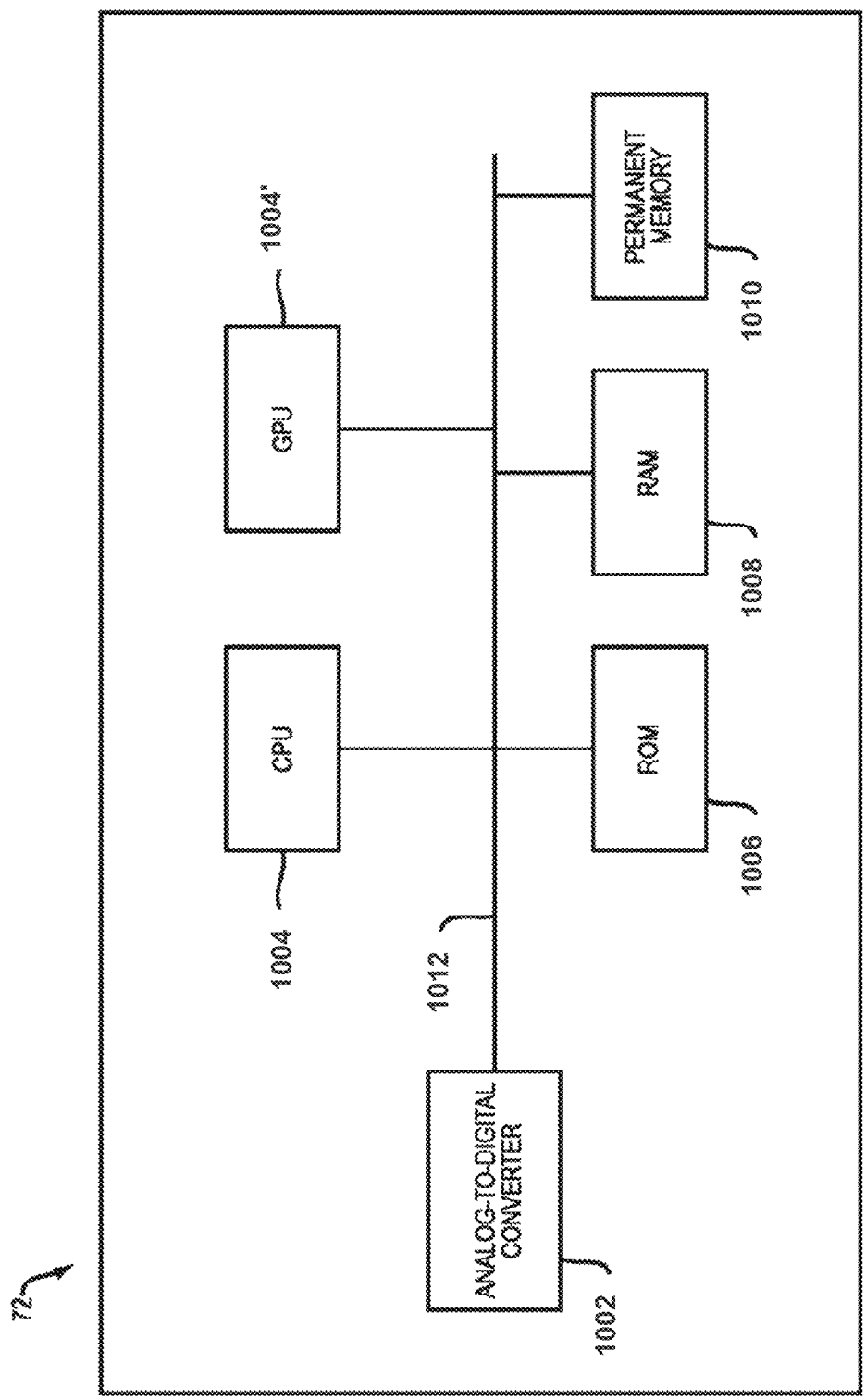
FIG. 10 schematically depicts selected components of an exemplary hardware implementation of an analysis module according to an embodiment of the present invention.

As noted above, the analysis module 72 can be implemented in hardware, firmware and/or software using techniques known in the art and in accordance with the present teachings. By way of example, FIG. 10 schematically depicts an exemplary implementation of analyzer 72, which includes an analog-to-digital converter 1002 for receiving the amplified fluorescence signal from the amplifier 70 and digitizing that signal to generate digitized fluorescence data. The analysis module further includes a central processing unit (CPU) 1004 for controlling the operation of the analysis module, including performing calculations and logic operations. The analysis module also includes ROM (read only memory) 1006, RAM (random access memory) 1008 and permanent memory 1010. A communications bus 1012 facilitates communication among various components of the analysis module, including communications between the CPU 1004 and other components. The memory modules can be used to store instructions for analyzing the fluorescence data and the analysis results. By way of example, in some embodiments, instructions for data analysis, e.g., instructions for performing the above blocks discussed in connection with FIGS. 9A and 9B, can be stored in the ROM 1006. The CPU can employ instructions stored in ROM 78 to operate on digitized fluorescence data stored in RAM 1008 to generate a fluorescence image of the sample (e.g., a one-dimensional or a two-dimensional image). The CPU can effect the storage of the fluorescence image in permanent memory 1010, e.g., in a database. As shown schematically in FIG. 10, the analysis module can optionally include a graphics processing unit (GPU) 1004' for performing calculations of pixel intensities and other quantities from the received data (e.g., fluorescence data).

Figure 11A:
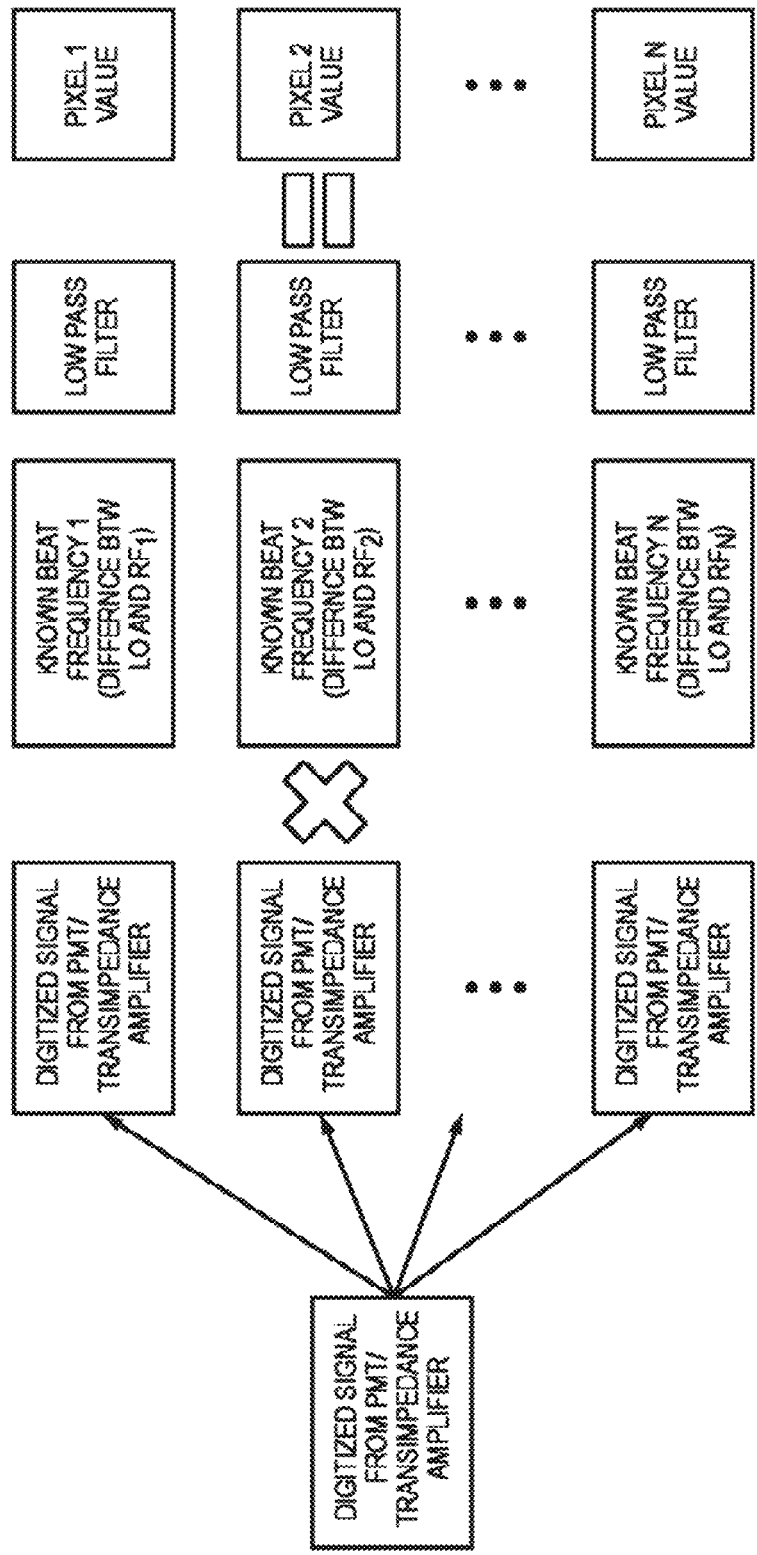
FIGS. 11A and 11B depict another method according to an embodiment of the invention for analysis of fluorescence signal obtained by illuminating a sample with a combined beam composed of a plurality of RF comb beams and a top-hat profiled LO beam.
Figure 11B:
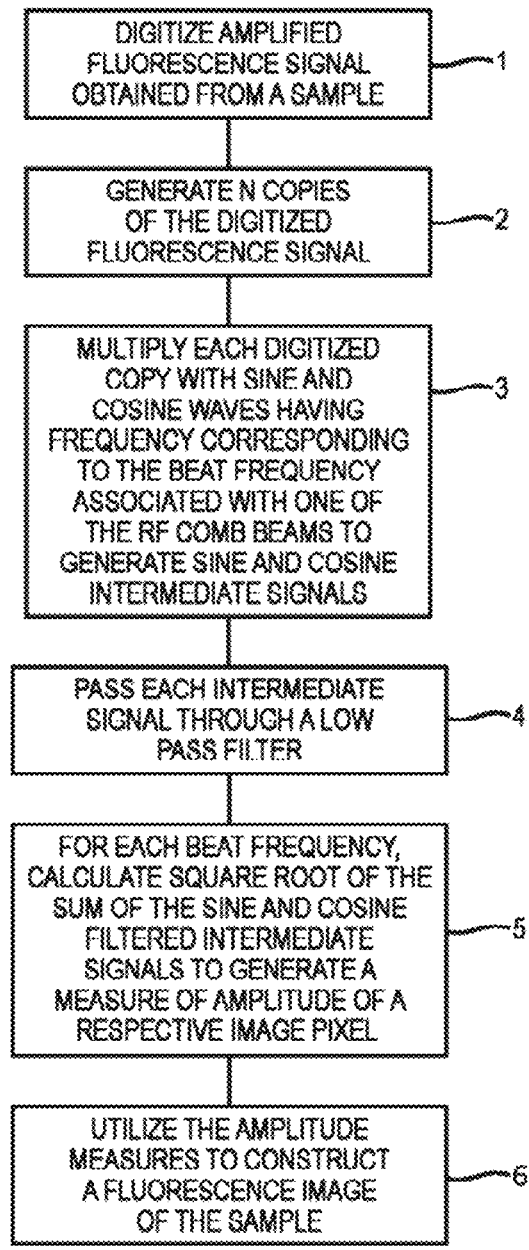

In some embodiments, the frequency demodulation of the output signal generated by the photodetector can be achieved using lock-in detection techniques. By way of example, with reference to FIGS. 11A and 11B, in one such embodiment, the amplified fluorescence signal is digitized (block 1) and several copies of the digitized fluorescence signal are generated (block 2), where the number (N) of the digitized copies corresponds to the number of frequencies associated with the RF comb beams. Each digitized copy of the signal is multiplied with sine and cosine waves having a frequency corresponding to a beat frequency equal to a difference between the frequencies of one of the RF comb beams and the LO beam to generate a plurality of intermediate signals (block 2). Each intermediate signal is passed through a low-pass filter (block 3), which has a bandwidth equal to one half of the frequency spacing between the RF comb frequencies.

For each beat frequency corresponding to one of the RF comb frequencies (in other words, for each frequency corresponding to a spatial location of the illuminated sample), square root of the sum of the squares of the two filtered intermediate signals corresponding to that frequency is obtained as a measure of the amplitude of an image pixel corresponding to the sample location illuminated by the LO beam and the RF comb beam having that frequency (block 4). In some embodiments, multiple fluorescence data signals corresponding to the same beat frequency (i.e., corresponding to the same sample location) can be processed in a manner discussed above and the pixel values can be averaged so as to obtain an average pixel value.

The above blocks can be repeated for fluorescence data obtained for each horizontal row of the sample as the sample flows through the flow cell in a vertical direction. The pixels values can be used to construct a fluorescence image (block 5).

The above lock-in detection method can be implemented in software, firmware and/or hardware. By way of example, in one embodiment the above lock-in detection method can be implemented using a field programmable gate array (FPGA), particularly if more than 6 frequencies are used. In some embodiments, a multi-frequency lock-in amplifier, such as HF2L-MF multi-frequency amplifier marketed by Zurich Instruments of Zurich, Switzerland can be employed.

Figure 12A:
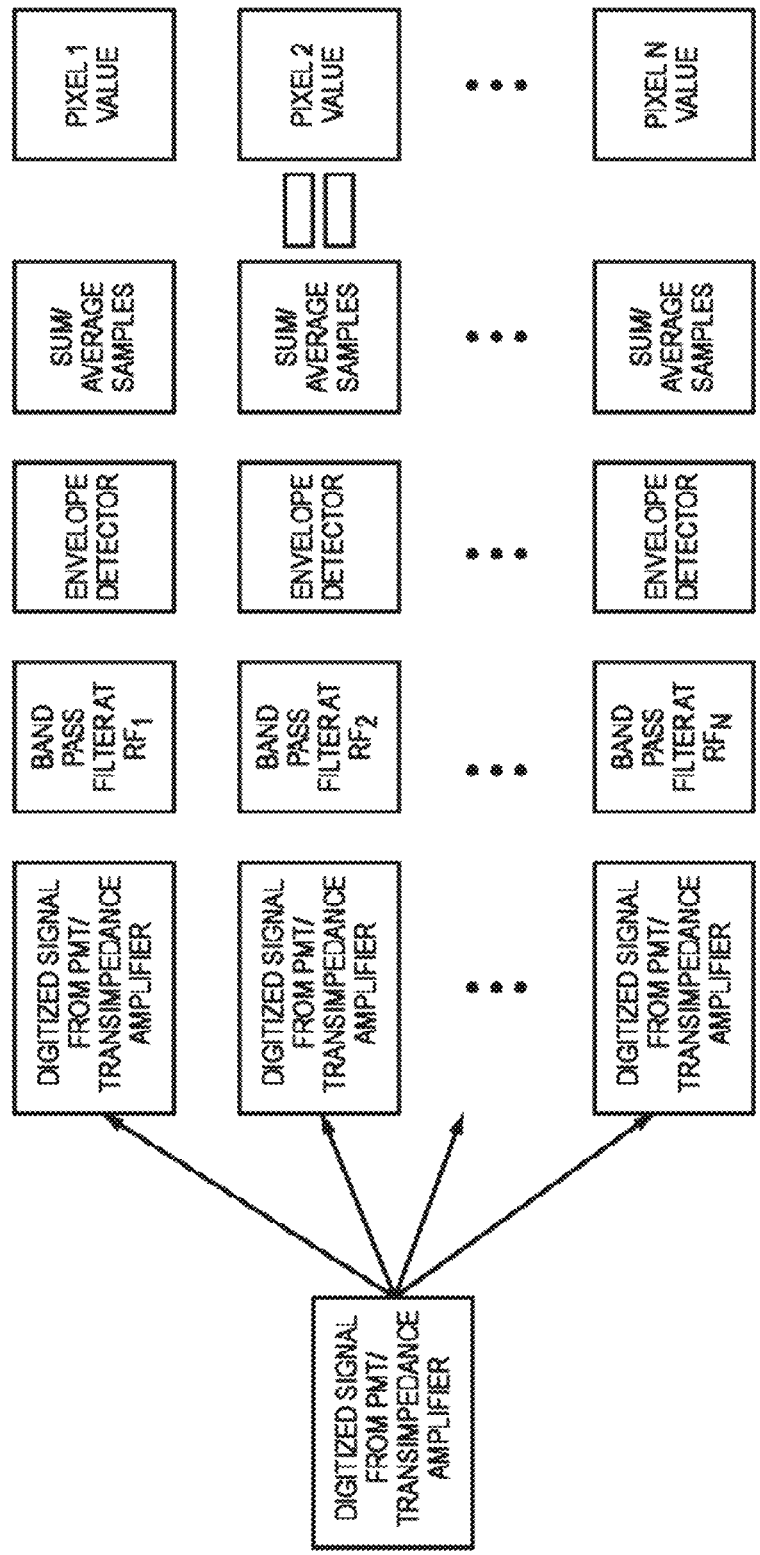
FIGS. 12A and 12B depict yet another method according to an embodiment of the invention for analysis of fluorescence signal obtained by illuminating a sample with a combined beam composed of a plurality of RF comb beams and a top-hat profiled LO beam.
Figure 12B:
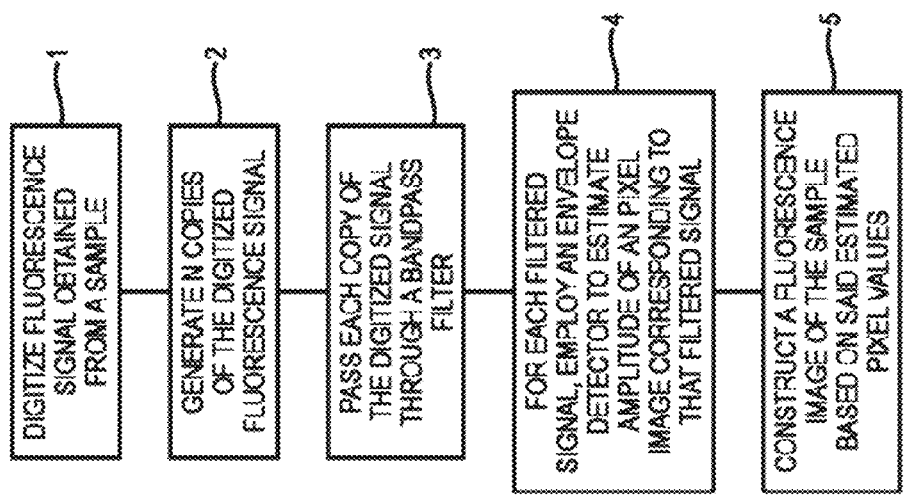

By way of further examples, in some embodiments the frequency demodulation of the detected fluorescence signal can be achieved by employing a bandpass filter-based image demodulation technique. By reference to FIGS. 12A and 12B, in one embodiment of such a frequency demodulation method, the fluorescence signal provided by the photodetector 64 and the amplifier 70 is digitized (block 1) and several copies of the digitized signal are generated (block 2), where the number (N) of the digitized copies corresponds to the number of frequencies associated with the RF comb beams. Each copy of the digitized fluorescence signal is filtered by passing that signal through a bandpass filter centered at a beat frequency associated with one of the RF comb beams (i.e., a beat frequency associated with a particular location of the sample) (block 3). More specifically, each bandpass filter is centered at one of N beat frequencies and has a bandwidth that is equal to half of the frequency spacing between adjacent beat frequencies.

An envelope detector at each beat frequency is employed to estimate, for each horizontal line, the amplitude of each pixel corresponding to that frequency (block 4). In some cases, a plurality of pixel values corresponding to a pixel, obtained by processing multiple fluorescent signals corresponding to a sample location associated with that pixel, is averaged to obtain an average pixel value. The above blocks can be repeated for fluorescence data obtained for each horizontal row of the sample as the sample flows through the flow cell in a vertical direction. The pixels values can be used to construct a one-dimensional or a two-dimensional fluorescence image of the sample (block 5).

The analysis module can also be configured to receive and process the brightfield and darkfield image data. For example, with reference to FIG. 7C and FIG. 8, the analysis module 72 can be further configured to receive the darkfield and brightfield image data from photodetectors 208 and 218 to generate darkfield and brightfield images. For example, with reference to FIG. 10, the instructions for generating the darkfield and brightfield images, e.g., in a manner known in the art, can be stored in permanent memory 82. The processor 76 can employ these instructions to process the received darkfield and brightfield image data to generate the images. The analysis module can be also configured to generate composite images by overlaying, e.g., a fluorescence image and one or both of the brightfield and darkfield images.

The fluorescence images as well as the brightfield and darkfield images generated by a system according to the present teachings, such as the above system 10, can be used for a variety of different ways. For example, the fluorescence image can be integrated to produce a value comparable to the data produced by a conventional flow cytometer. The fluorescence image can also be analyzed to determine the location of fluorescent probe giving rise to that image (e.g., it can be determined whether the probe is the nucleus, cytoplasm, localized to organelles, or on the outside of the cell membrane). Further, in some applications, multiple fluorescent images obtained by detecting different fluorescent bands, all of which taken from the same cell, can be used to determine the degree of co-localization of multiple fluorescent probes within a cell. Additionally, the analysis of cell morphology, cell signaling, internalization, cell-cell interaction, cell death, cell cycle, and spot counting (e.g., FISH), among others, are possible using multicolor fluorescence, brightfield, and darkfield images.

As noted above, the system 10 can be operated in at least three different modes. In one mode discussed above, an LO beam and a plurality of RF comb beams concurrently illuminate a portion of the sample (e.g., locations disposed along a horizontal extent), and the fluorescence radiation emitted from the illuminated locations is detected and analyzed in order to construct a fluorescence image of the sample. In another operational mode, rather than applying a plurality of RF drive signals concurrently to the AOD, a frequency ramp containing the drive signals is applied to the AOD such that the frequency of the laser beam is changed over time from a start frequency ($f_1$) to an end frequency ($f_2$). For each drive frequency in the frequency ramp, the frequency of the laser beam is shifted by that drive frequency and the sample is illuminated by the frequency-shifted laser beam to elicit fluorescence radiation from the sample. In other words, in this mode, the system is operated to obtain fluorescence radiation from the sample by illuminating the sample successively over a temporal interval with a plurality of frequencies, which are shifted from the central laser frequency. The frequency shift generated by the AOD is accompanied by an angular deflection such that using the same optical path, the beam is scanned across the sample at a high speed.

More specifically, in this operational mode, the RF frequency synthesizer 10 is employed to ramp a drive signal applied to the AOD 18 from a start frequency ($f_1$) to an end frequency ($f_2$). By way of example, the frequency range over which the drive signal is ramped can be from about 50 MHz to about 250 MHz. In some embodiments, the drive signal is ramped from about 100 MHz to about 150 MHz. In this embodiment, the drive frequency is changed over time continuously, e.g., to achieve a high speed. In other embodiments, the drive frequency can be changed in discrete steps from a start frequency ($f_1$) to an end frequency ($f_2$).

The drive frequencies are chosen such that the frequency-shifted beam would miss the mirror 28 and propagate along an optical path defined by lens 26, lens 30, mirrors 40/42, a beam splitter 44, lens 46, mirror 56, lens 50, mirror 58 and the objective lens 52 to illuminate a portion of the sample flowing through the sample holder. The ramp rate is preferably fast enough so as to ameliorate and preferably prevent, any blur in the vertical direction of a fluorescence image to be generated based on the emitted fluorescence radiation as the sample flows across the beam. This can be achieved, for example, by matching the ramp rate with the sample's flow speed. The laser spot size at the sample can be used to estimate appropriate rates. By way of example, for a laser spot size of 1 micrometer, the scan time across 1 line should be 10 microseconds or less for a sample flow speed of 0.1 meters per second to avoid image blur.

The fluorescence radiation emitted from the sample in response to illumination by the excitation radiation is collected and detected in a manner discussed above. Specifically, with reference to FIG. 8, the fluorescence radiation is detected by photodetector 64. The detected fluorescence is amplified by the amplifier 70 and the amplified signal is analyzed by the analysis module 72 to reconstruct a fluorescence image of the sample. The reconstruction of the image is performed by assigning a horizontal pixel location to a specific time within the scan period from the start frequency ($f_1$) to the end frequency ($f_2$). As opposed to analyzing the amplitude of a frequency component to obtain pixel values as in the above operational mode, the demodulation approach used in this operational mode only uses the time domain values of the detected fluorescence signal to assign values to the pixels of the image. The process can be repeated as the sample flows in a vertical direction so as to obtain a two-dimensional fluorescence image of the sample.

The fluorescence radiation, if any, emitted by the sample is collected by photodetector 64. Referring to FIG. 8, the detected fluorescence radiation is amplified by the amplifier 70. The analysis module 72 receives the amplified signal. In this operational mode, the analysis module analyzes the fluorescence signal to determine the fluorescence content of the sample, e.g., a cell/particle. Since there is only one beam exciting the sample in this operational mode, no beat frequencies are generated in response to exciting the sample. Hence, there is no image information in the frequency domain of the fluorescence signal. Rather, the detected fluorescence signal has image information encoded in the time domain. In this operational mode, an image can be digitally reconstructed using the time values of the detected fluorescence signal as the horizontal pixel coordinate, and the digitized voltage values of the fluorescence signal as the pixel values (brightness). Each scan of the drive frequencies applied to the AOD produces one horizontal line (row) of the image. The image reconstruction is achieved via consecutive scans as the sample flows through the illumination area (point).

In yet another operational mode, the system 10 can be operated to illuminate a plurality of locations of a sample concurrently by a single excitation frequency, which can be generated, e.g., by shifting the central frequency of a laser beam by a radiofrequency. More specifically, referring again to FIG. 1, in such an operational mode a single drive radio frequency can be applied to the AOD 18 to generate a laser beam having a frequency that is shifted relative to the laser beam entering the AOD 18. Further, the frequency-shifted laser beam exhibits an angular shift relative to the laser beam entering the AOD such that the radiofrequency laser beam is intercepted and reflected by the mirror 28 towards the top-hat beam shaper 34 via lens 32 and mirrors 33 and 35. The beam exiting the top-hat beam shaper is reflected by the beam splitter 44 and is focused by the lens 46 onto the intermediate image plane 48. In this plane, as shown schematically in FIG. 13A, the laser beam 1300 shows a stretched profile along the horizontal direction.

The horizontally-stretched laser beam is reflected by the mirror 56 to the positive lens 50. After passage through the lens 50, the laser beam is reflected by the mirror 58 to the objective lens 52. As discussed above, the positive lens 50 and the objective lens 52 form a telescope for relaying the top-hat profiled laser beam from the intermediate image plane 48 onto a sample flowing through the flow cell 54.

The horizontally-stretched laser beam illuminates a horizontal extent of the sample to excite a fluorophore of interest, if present in the sample, along that horizontal extent. Thus, in this operational mode, unlike the first operational mode in which a plurality of horizontal locations of the sample is illuminated at different excitation frequencies, a plurality of horizontal locations of the sample is illuminated at the same excitation frequency. This operational mode does not enable a user to obtain an image of cells or particles that flow by. However, in this operational mode, a higher optical power can typically be applied to the sample than in the other two operational modes, which can be useful for obtaining a higher signal-to-noise ratio data if images are not required. This operational mode is accessible by merely altering the electronic signal driving the acousto-optic deflector, without a need to make any mechanical changes to the system.

Thus, the system 10 can be operated in three distinct operational modes to elicit fluorescence radiation from a sample.

Figure 13B:
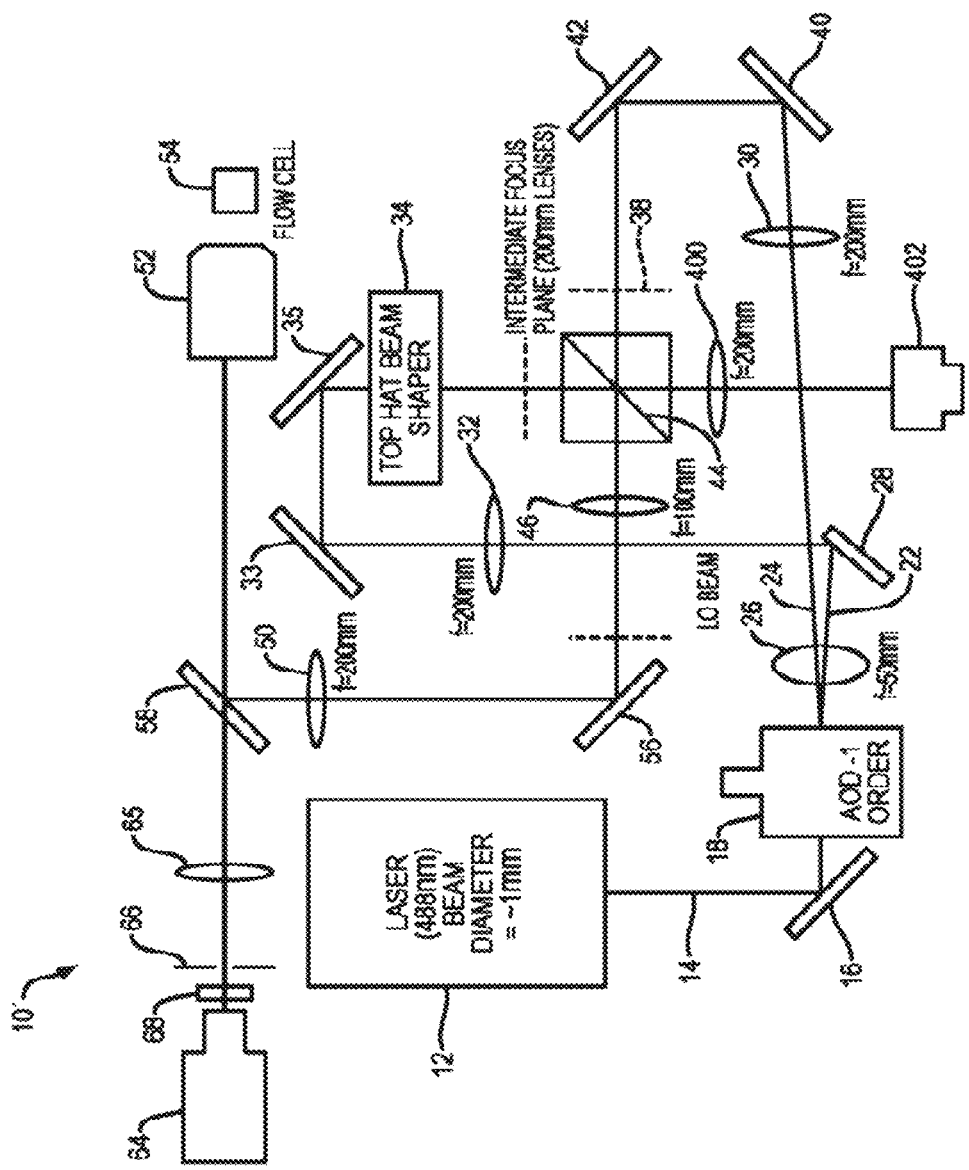
FIG. 13B is a schematic view of a system according an embodiment of the present teachings that allows for fluorescence lifetime measurements and fluorescence lifetime imaging.

In some embodiments, fluorescence lifetime measurements can be performed at each spatial position on the sample, e.g., by comparing the phase of the beats of each of the radiofrequency-shifted and local oscillator beams with the phase of a respective radiofrequency component in the detected fluorescence signal. By way of example, FIG. 13B shows a system 10', a modified version of the system 10 discussed above, that allows for such fluorescence lifetime measurements (certain components shown in FIG. 1 are not depicted in this figure for brevity). Specifically, a portion the RF comb beams incident on the beam splitter 44 is reflected by the beam splitter onto a convergent lens 400 (by way of illustration in this embodiment the lens 400 has a focal length of 200 mm, though other focal lengths can also be used). The lens 400 focuses that portion of the RF comb beams onto a photodiode 402, which detects the excitation beam. The output of the photodiode 402 can be received by the analysis module 72 (See, FIG. 8). The analysis module can provide frequency de-multiplexing of the excitation beam, e.g., using one of the de-modulation techniques discussed above and determine the phase of each radio frequency component in the excitation beam. This can provide, for each radiofrequency component in the detected fluorescence signal, a reference phase with which the phase of that radiofrequency component can be compared. For example, the real and imaginary components of an FFT of the excitation signal or the I and Q components of lock-in type demodulation can be employed. Alternatively, the output of the detector detecting the brightfield image of the sample/flow cell can be used to obtain reference phases with which the phases of the fluorescence beat frequencies can be compared.

More specifically, the analysis module 72 can provide frequency de-multiplexing of the detected fluorescence signal, e.g., in a manner discussed above. As will be appreciated by one skilled in the art, for each beat frequency in the fluorescence signal, the phase of the radiofrequency component can be compared with the respective reference phase of the excitation beam to obtain spatially-resolved fluorescence lifetime measurements and a fluorescence lifetime image.

In certain embodiments, the subject systems include flow cytometry systems employing the optical configurations described above for detecting light emitted by a sample in a flow stream. In certain embodiments, the subject systems are flow cytometry systems which include one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494; and 9,097,640, the disclosures of which are herein incorporated by reference in their entirety.

As discussed above, in some embodiments the subject systems are configured for imaging particles (e.g., cells) in a sample flowing as a flow stream, such as in the flow stream of a flow cytometer. The flow rate of particles in the flow stream may be 0.00001 m/s or more, such as 0.00005 m/s or more, such as 0.0001 m/s or more, such as 0.0005 m/s or more, such as 0.001 m/s or more, such as 0.005 m/s or more, such as 0.01 m/s or more, such as 0.05 m/s or more, such as 0.1 m/s or more, such as 0.5 m/s or more, such as 1 m/s or more, such as 2 m/s or more, such as 3 m/s or more, such as 4 m/s or more, such as 5 m/s or more, such as 6 m/s or more, such as 7 m/s or more, such as 8 m/s or more, such as 9 m/s or more, such 10 m/s or more, such as 15 m/s or more and including 25 m/s or more. For example, depending on the size of the flow stream (e.g., the flow nozzle orifice), the flow stream may have a flow rate in the subject systems of 0.001 µL/min or more, such as 0.005 µL/min or more, such as 0.01 µL/min or more, such as 0.05 µL/min or more, such as 0.1 µL/min or more, such as 0.5 µL/min or more, such as 1 µL/min or more, such as 5 µL/min or more, such as 10 µL/min or more, such as 25 µL/min or more, such as 50 µL/min or more, such as 100 µL/min or more, such as 250 µL/min or more and including 500 µL/min or more.

Figure 14A:
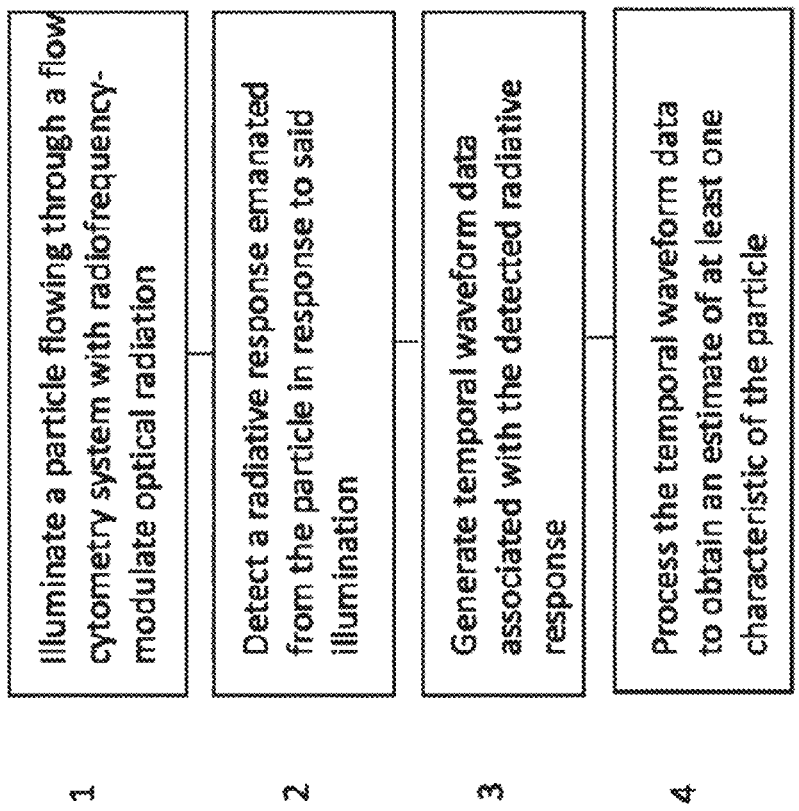
FIG. 14A is a flow chart depicting determining an estimate of at least one characteristic of a particle flowing through a flow cytometry system.

In some aspects, methods and systems are disclosed for providing an estimate of one or more characteristics of a particle, e.g., a cell. By way of example, FIG. 14A presents a flow chart depicting one exemplary method according to an embodiment of the present teachings for determining one or more characteristics of a particle. A particle is illuminated with a radiofrequency-modulated optical beam as the particle flows through a flow cytometry system so as to elicit at least one radiative response from the particle (block 1). By way of example, the radiofrequency-modulated optical beam can include at least two beamlets having optical frequencies shifted from one another by a radiofrequency. In some embodiments, the radiofrequency shift can be in a range of about 10 MHz to about 250 MHz. For example, the radiofrequency shift can be in a range of about 55 MHz to about 225 MHz, such as from about 60 MHz to about 200 MHz, such as from about 65 MHz to about 175 MHz, such as from 70 MHz to about 150 MHz and including from about 75 MHz to about 125 MHz. By way of example, in some embodiments, the radiofrequency-modulated optical beam can be generated by introducing a laser beam to an acousto-optic deflector (AOD) and applying one or more drive signals at one or more radiofrequencies to the AOD in order to generate a plurality of angularly-separated beamlets having optical frequencies that are shifted relative to one another by said radiofrequencies, e.g., in a manner discussed above.

In some embodiments, the radiative response elicited from the particle in response to the illumination of the particle by the radio-frequency modulated optical beam can be any of fluorescent and/or scattered radiation.

With continued reference to the flow chart of FIG. 14A, the radiative response emanating from the particle can be detected (block 2) and a temporal waveform data associated with the radiative response can be generated (block 3). A variety of radiation detection modalities and detectors, such as those discussed above, can be used to detect the elicited radiation response. In some embodiments, the generated waveform can be a fluorescence and/or scattering waveform data. The waveform data can be processed to obtain an estimate of at least one characteristic of the particle. In many embodiments, such processing of the waveform data to obtain an estimate of at least one characteristic of the particle can be performed without generating an image of the particle based on the waveform data. In some embodiments, the processing includes analyzing one or more beat frequencies modulating the temporal waveform data to obtain the estimate of at least one characteristic of the particle. In some embodiments, the processing is performed sufficiently fast such that a latency associated with obtaining an estimate of at least one characteristic of the particle is less than about 100 microseconds.

In some embodiments, the above method can be used to obtain an estimate of any of a dimensional size of the particle, a ratio of sizes of the particle along two different dimensions, co-localization of fluorescence radiation emitted by two or more markers associated with the particle, or a degree of punctateness of the radiative response (e.g., the degree of punctateness of fluorescent radiation emitted by the particle), among others.

The above method can be used to obtain estimates of one or more characteristics of a variety of different particles. By way of example, the particle can be any of a cell, a small organism (e.g., the nematode c. elegan), a bead, a microparticle, a nanoparticle, a viral particle, a bacterium, an exosome, or a pharmaceutical product.

Figure 14B:
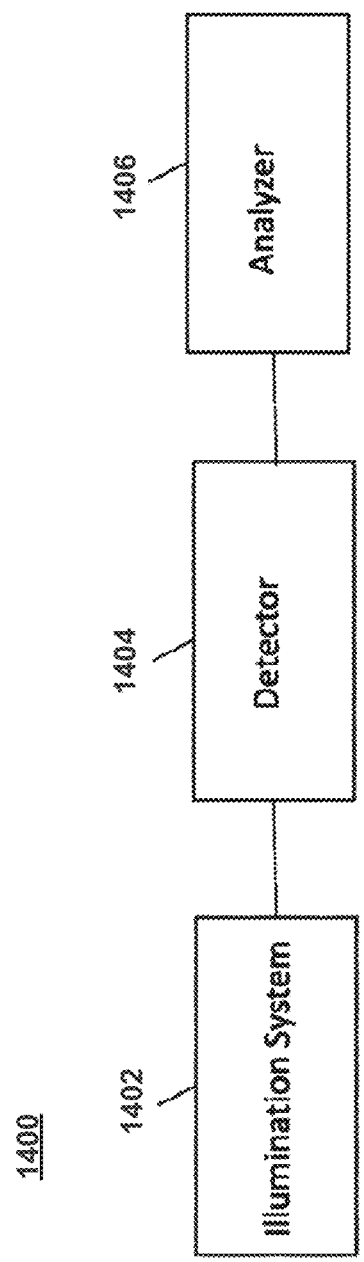
FIG. 14B schematically depicts a system according to an embodiment for determining an estimate of at least one characteristic of a particle flowing through a flow cytometry system.

FIG. 14B schematically depicts a system 1400 according to an embodiment for estimating at least one characteristic of a particle, such as a cell. The exemplary system 1400 includes an illuminating system 1402 for illuminating one or more particles flowing through a cell of a flow cytometry system with a radiofrequency-modulated optical laser beam. A detector 1404 can detect a radiative response of the particle, e.g., fluorescent and/or scattered radiation, in response to its illumination, and generate one or more signals indicative of the radiative response. An analyzer 1406 can receive the signal(s) from the detector and generate temporal waveform data and operate on that waveform data so as to derive an estimate of one or more characteristics of the particle.

The analyzer 1406 can employ a variety of different methods for analyzing the waveform data to obtain an estimate of one or more characteristics of a particle, such as a cell. By way of example, in some embodiments, a particle can be stained with at least two fluorescence markers, where each marker is configured to emit fluorescent radiation in response to illumination by radiofrequency-modulated optical radiation. The fluorescent radiation can be detected and digitized to generate fluorescence waveforms each corresponding to one of the markers. The analyzer can operate on the fluorescence waveforms to obtain a measure of co-localization of the fluorescence radiation emanating from the markers. Specifically, the analyzer can apply a high-pass or a band-pass filter to at least one of the waveforms to generate at least one filtered waveform followed by a point-wise multiplication of the waveforms to generate a resultant multiplicative waveform, integrate the multiplicative waveform to obtain an integrated value, and compare the integrated value with a predefined threshold to obtain a measure of co-localization. By way of another example, in some embodiments, an estimate of the size of a particle along a direction perpendicular or parallel to the direction of the particle flow in a flow cytometry system can be obtained. For example, in some such embodiments, an estimate of a particle size in a direction perpendicular to the direction of particle flow can be obtained by squaring a fluorescence waveform corresponding to fluorescent radiation emitted by the particle in response to illumination by a radiofrequency-modulated optical beam, applying a bandpass filter to the squared waveform, integrating the filtered waveform, and comparing the integrated value with a predefined threshold. Further, in some embodiments, the analyzer can use scattering data to obtain an estimate of the size of a particle in a direction parallel to the direction of particle flow.

As discussed below, one or more estimated characteristics of a particle flowing through a flow cytometry system can be employed to arrive at a sorting decision regarding that particle, i.e., whether or not to sort that particle. Some examples of processing methods that can be used to operate on the waveform data to obtain an estimate of at least one characteristic of a particle are discussed below in the context of using the estimates of characteristics of cells flowing through a flow cytometer to arrive at sorting decisions regarding those cells. It should be understood that such processing methods can be used to obtain estimates of characteristics of particle other than cells, and further the estimated characteristics may not be used for sorting purposes.

Figure 14C:
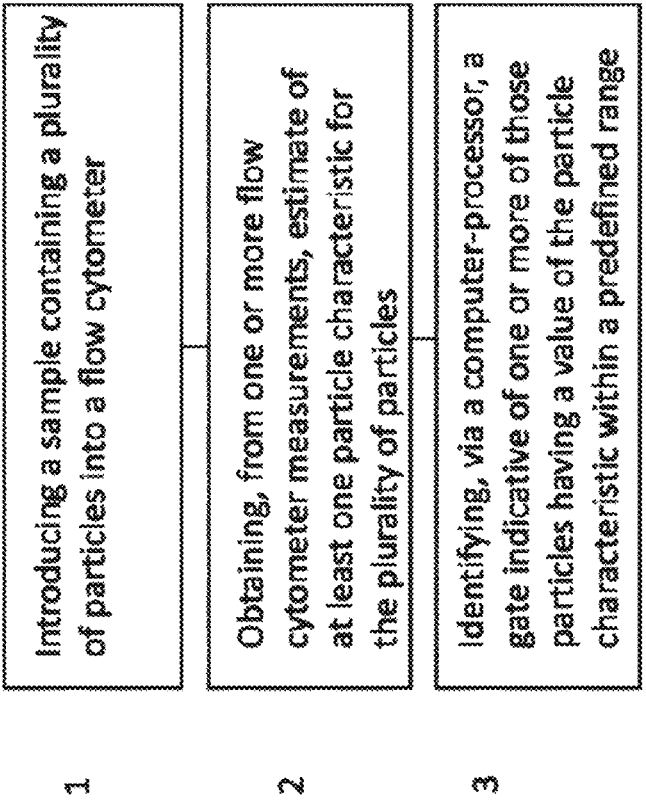
FIG. 14C is a flow chart depicting a method according to an embodiment for gating particles in a flow cytometry system based on values of one or more particle characteristics.

In a related aspect, methods are disclosed for automatic gating (e.g., computer-assisted gating) of a population of particles, e.g., cells, flowing through a flow cytometer based on one or more characteristics of the particles. By way of example, such a method can gate a subset of a plurality of particles flowing through a flow cytometer based on the sizes of the particles being within a predefined range. For example, with reference to the flow chart of FIG. 14C, such a method can include introducing a sample containing a plurality of particles into a flow cytometer (block 1), and obtaining, from one or more flow cytometer measurements, estimates of at least one particle characteristic for the plurality of the particles (block 2). Obtaining at least one particle characteristic can include illuminating a particle as it flows through the flow cytometer with radiation having at least two optical frequencies shifted from one another by a radiofrequency to elicit a radiative response from the particle, detecting the radiative response from the particle to generate temporal waveform data associated with the response, and processing said temporal waveform data to obtain a value of said at least one particle characteristic by analyzing one or more beat frequencies modulating said temporal waveform data. The method can further include identifying, via a computer processor, a gate indicative of one or more particles having a value of the particle characteristic that lies within a predefined range. By way of example, the particles having a dimensional size (e.g., a lateral size) within a predefined range can be gated.

A system such as the system depicted in FIG. 14B can be employed to perform the above gating methods. For example, the analyzer 3006 can be programmed to determine an estimate of at least one characteristic of a plurality of particles, e.g., based on the analysis of one or more beat frequencies in the fluorescent radiation emitted by those particles in response to illumination by a radiofrequency-modulated optical beam, and determine whether the estimate of the characteristic of a particle is within a predefined range in order to arrive at a gating decision with respect to that particle (e.g., if the determined characteristic is within a predefined range, the particle will be gated). In some embodiments, the teachings of U.S. Pat. No. 8,990,047 titled "Neighborhood Thresholding in Mixed Model Density Gating", as modified based on the present teachings can be used to gate particles flowing through a flow cytometer. U.S. Pat. No. 8,990,047 is hereby incorporated by reference in its entirety.

In some aspects, methods and systems are disclosed for sorting cells based on interrogation of those cells via radiofrequency modulated optical radiation, e.g., an optical radiation beam comprising two or more optical frequencies separated from one another by one or more radiofrequencies. In some embodiments, the optical beam can include a plurality of angularly or spatially separated beamlets each of which has a radiofrequency shift relative to another. In some cases, the use of such a beam allows illuminating different locations within a particle (e.g., a cell) at different radiofrequency-shifted optical frequencies. As discussed in more detail below, such methods can provide a sorting decision by employing the time-varying signal generated by the cells in response to illumination by the optical beam without a need to compute a fluorescence image based on the detected signal(s). While various embodiments of the methods according to the present teachings are discussed below in the context of sorting cells (e.g., in a flow cytometry system), the methods described herein can also be employed for sorting other types of particles, such as, small organisms (e.g., the nematode c. elegan), beads, microparticles, nanoparticles, viral particles, bacteria, exosomes, or pharmaceutical products. In some embodiments, the particles that can be sorted using the present teachings can have a size (e.g., a maximum size) in a range of about 50 nanometers to about 1 millimeter, e.g., in a range of about 100 nanometers to about 1 micrometer.

Further, in many embodiments, the sort methods discussed herein can be employed to provide sort decisions with a low latency, e.g., such that a cell or other particle can be sorted using a sorting apparatus operating at a high particle throughput (e.g., more than 1000 sorting operations per second may be performed). By way of example, the methods described herein can be used to make a sort decision with a latency equal to or less than about 100 microseconds, e.g., in a range of about 10 microseconds to about 100 microseconds, or in a range of about 20 microseconds to about 80 microseconds, or in a range of about 30 microseconds to about 70, or 50, microseconds. The term "latency" is used herein to indicate the time lapse between illuminating a particles, e.g., a cell, with interrogating radiation and arriving at a characteristic of the particle and/or a sorting decision regarding that particle.

Figure 14D:
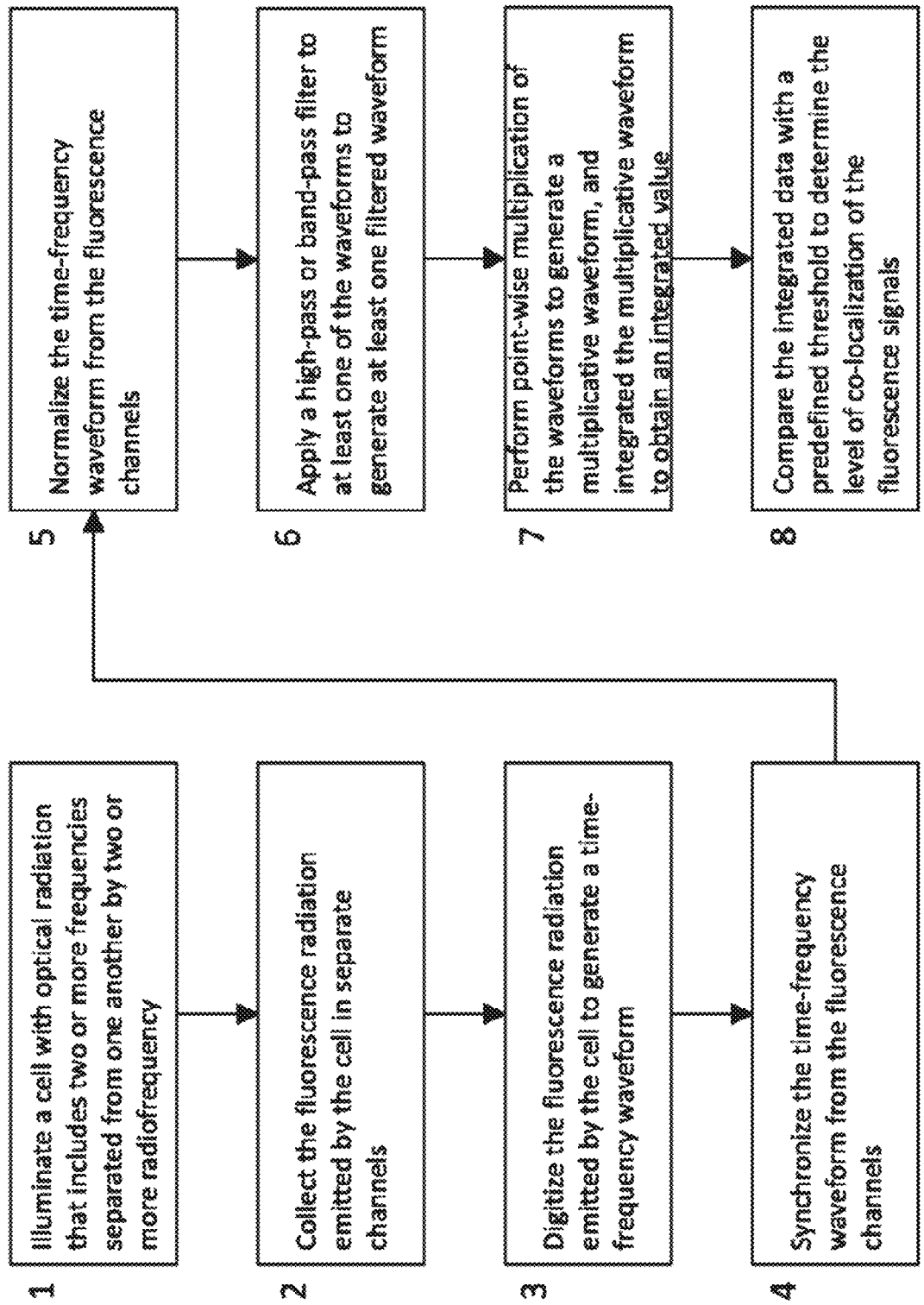
FIG. 14D is a flow chart depicting an embodiment for making a sorting decision based on co-localization of fluorescence radiation emitted from a particle, e.g., a cell, in two or more different frequency channels.

By way of example, the flow chart of FIG. 14D depicts a method according to an embodiment for sorting particles (e.g., cells) based on the degree of co-localization of fluorescence signals corresponding to two or more fluorophores (e.g., exogenous and/or endogenous fluorophores) emanating from the particles. Without any loss of generality, the particle is assumed to be a cell in the following discussion. At block (1), a cell is optically interrogated via illumination with an optical radiation beam that includes two or more optical frequencies that are separated from one another by one or more radiofrequencies. In some cases, the optical beam can include a plurality of angularly or spatially separated beamlets each of which has a radiofrequency shift relative to another. The use of such a beam allows illuminating different locations within the cell at different optical frequencies, which are shifted from one another by one or more radiofrequencies. The optical frequencies can be selected to excite two or more fluorophores that are expected to be associated with the cell. For example, the fluorophores can be fluorescent dye molecules with which the cell are tagged, e.g., via staining. By way of example, in some embodiments, the optical frequencies of the radiation beam can be in a range of about 300 THZ to about 1000 THZ and the radiofrequency separation between the optical frequencies can be, for example, in a range of about 50 MHz to about 250 MHz.

The fluorescent radiation emanating from the excited cell can then be collected in two (or more) separate fluorescence channels, each of which corresponds to fluorescent radiation emitted by one of the fluorophores (block 2). This can be achieved, for example, by employing the detector arrangement discussed above in connection with FIG. 7A. The collected fluorescent radiation in each channel can be digitized (block 3) and represented as a time sequence of signal values (fluorescence intensity). In this and other embodiments, such a time sequence of signal values, which can encode beat frequencies present in the fluorescent radiation is referred to as time-frequency waveform. The digitized time-frequency waveform corresponding to two or more fluorescence channels are temporally synchronized (block 4) and normalized (block 5). The normalization can be achieved, for example, by dividing each waveform by its maximum value and multiplying the waveform by a scaling factor.

A high-pass or a band-pass filter can be applied to at least one of the waveforms to generate at least one filtered waveform (block 6). In some embodiments, a low-pass filter is applied that allows the passage of frequencies less than about 1 MHz, and substantially blocks higher frequencies. Some examples of suitable low-pass filters include, without limitation, time-domain finite impulse response (FIR) filters or Fourier-domain filters.

The waveforms can then be point-wise multiplied to obtain a multiplicative waveform, and the multiplicative waveform can be integrated to obtain an integrated value (block 7). By way of illustration, FIG. 15 shows an array 1500 that represents the filtered normalized time-sequenced digitized fluorescence signal detected in one fluorescence channel and an array 1501 that represents the filtered normalized time-sequenced digitized fluorescence signal detected in another fluorescence channel, which is temporally synchronized with the array 1500 (for simplicity, in this illustrative example, the number of fluorescence channels is chosen to be two and the number of array elements is chosen to be ten, it should be understood that the number of fluorescence channels may be more than 2 and the number of array elements more than 10). This data is herein referred to as a time-frequency waveform. A resultant array 1502 is obtained via point-wise multiplication of the data in the arrays 1500 and 1501.

The temporal fluorescence signal from each channel includes beat frequencies corresponding to the interference of the radiofrequency-separated optical frequencies of the optical radiation beam. As such, the multiplication of their respective digitized data would exhibit the sum and difference of those frequencies. If the signals in the two or more fluorescence channels originate from substantially similar spatial locations within the excited cell, the resultant time-domain data obtained via multiplication of those signals would include frequency components at DC or close to DC based on the degree of co-localization of the signals in different fluorescence channels emanating from the excited cell.

At block (8), the integrated result is compared with a predefined threshold to determine whether the interrogated cell exhibits sufficient co-localization of the fluorescence signals to be qualified as a cell that satisfies the criterion for sorting. For example, if the integrated result equals or exceeds the predefined threshold, the cell would be selected for sorting. Otherwise, the cell would not be selected for sorting.

The above sorting method based on fluorescence co-localization can be used in a variety of applications, for example, for translocation analysis.

In another aspect, a method for sorting cells in a flow cytometry system based on an estimate of the cell size is provided, where an estimate of the cell size is obtained via analysis of fluorescent radiation emitted by the cell. For example, the method utilizes the duration of a fluorescence pulse emanating from a cell to estimate the dimension of the cell along the direction of flow and analyzes the power contained in a low-pass filtered signal obtained by passing the square of the fluorescence signal through a low-pass filter to perform a sorting decision based on an estimate of a lateral dimension of the cell (e.g., a dimension of the cell orthogonal to the direction of cell flow).

Figure 16:
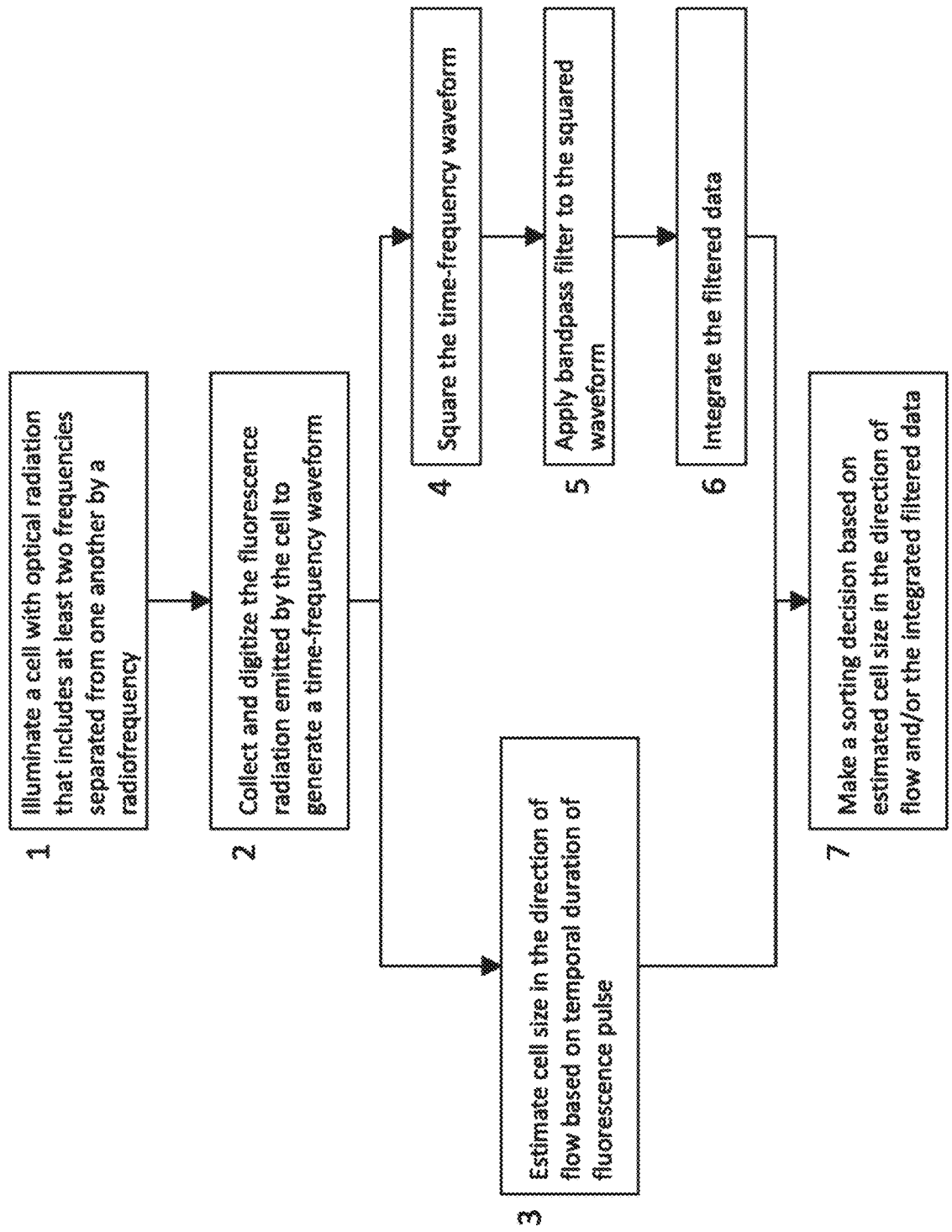
FIG. 16 is a flow chart depicting cell sorting based on a cell size in accordance with an embodiment of the present invention, FIG. 17A schematically depicts a hypothetical cell illuminated by a hypothetical beam comprising a plurality of radiofrequency-modulated beamlets.

More specifically, with reference to FIG. 16, in one embodiment, a cell is optically interrogated via illumination with an optical radiation beam that includes two or more optical frequencies that are separated from one another by one or more radiofrequencies (block 1). Similar to the previous embodiments, the optical beam can include, for example, a plurality of angularly or spatially separated beamlets each of which has a radiofrequency shift relative to another. The optical frequencies can be selected to excite one or more exogenous and/or endogenous fluorophores associated with the cell. The cell passes through the optical radiation beam and emits fluorescence in response to excitation by the beam. Without loss of generality, in this embodiment, the cell is assumed to flow in a vertical direction through the illumination beam and the emitted fluorescence is detected in a lateral (horizontal) direction that is substantially orthogonal to the flow direction of the cell.

A fluorescence signal emanated from the cell is then detected and digitized to generate a time-frequency waveform (block 2). The detected fluorescence radiation can then be analyzed to estimate the cell size, as discussed below. In some embodiments, the duration of a light scatter pulse emanated from the cell can be used to estimate the cell size along the direction of flow.

The duration of a fluorescence pulse emanating from a cell is related to the dwell time of the cell within the interrogating optical radiation beam, which is in turn related to the dimension of the beam in a direction parallel to the flow direction, the cell size in the direction of flow and the flow velocity of the cell. If the beam illuminating the cell has a diameter (H), and the flow velocity of the cell is V, and the cell has a size D (e.g., a diameter) in the direction of flow, then the size D can be approximated by the following relation:

$$D = V*T - 2*H \qquad \text{Eq. (2)}$$

where T is the detected optical pulse width. Hence, at block (3), the cell size in the direction of flow is estimated based on the temporal duration of the fluorescence or light scatter pulse emanated from the cell, e.g., using the above relation.

With continued reference to the flow chart of FIG. 16, in order to estimate the lateral size of the cell, the digitized fluorescence data is squared (block 4) and a bandpass filter is applied to the squared fluorescence data (block 5). The filtered data is then integrated to obtain a measure of integrated pulse power (block 6). The integrated pulse power can provide a measure of the lateral size of the cell. More specifically, based on the power present in the difference frequencies (which result as a consequence of the squaring operation) that fall within the band of the bandpass filter, the integrated pulse power can provide a measure of the lateral size of the cell.

At block (7), the estimate of the cell size in the flow direction and/or the integrated pulse power associated with the filtered data can be employed to make a sorting decision with respect to the cell. For example, in some embodiments, the estimated cell size in the direction of flow can be compared with a first threshold and the integrated pulse power can be compared with a second threshold to make a sorting decision. By way of example, in some cases, if both the estimated cell size in the direction of flow and the integrated pulse power exceed the respective thresholds, a positive sorting decision is made (i.e., the cell is selected). Alternatively, the sorting decision can rely only on the estimate of the cell size in the direction of the flow or the integrated pulse power. As discussed further below, in some cases, the ratio of the estimated vertical and horizontal cell sizes can be employed to make a sorting decision.

Figures 17A, 17B:
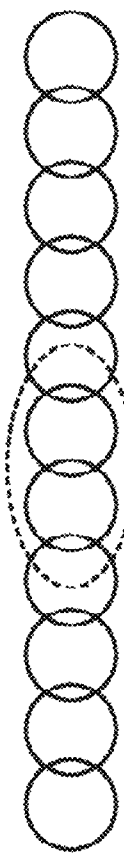
FIG. 17B schematically depicts a hypothetical fluorescence waveform emitted from the illuminated cell shown in FIG. 17A as well as a waveform obtained by squaring the fluorescence waveform.

By way of further illustration of making a sorting decision based on an estimate of the lateral size of a cell, FIG. 17A schematically depicts a hypothetical cell illuminated by a hypothetical beam comprising a plurality of radiofrequency-modulated beamlets with radiofrequency modulations extending from 15 MHz to 25 MHz separated from one another by 1 MHz. The dashed line schematically depicts a cross-sectional view of the illuminated cell in a plane orthogonal to the direction of illumination. The fluorescence radiation collected from the cell and digitized can be in the form of a time-sequenced array 1700 of digitized fluorescence values, as shown schematically in FIG. 17B (the array is shown here only for illustrative purposes and not to limit the number of array elements that may be present in an actual fluorescence waveform). The waveform 1700 is squared to obtain the waveform 1701. A bandpass filter is then applied to the squared fluorescence waveform 1701, where the filter allows the passage of selected modulation frequencies between two frequencies $f_1$ and $f_2$ (where $f_2 > f_1$) while substantially blocking those modulation frequencies that are lower than $f_1$ or greater than $f_2$. By way of example, the bandpass filter can be an FIR bandpass filter, though other suitable filters known in the art may also be employed. The filtered data is indicative of the power present in the detected fluorescence pulse at modulation frequencies between $f_1$ and $f_2$. The filtered data is then integrated to obtain a measure of the total pulse power at frequencies between $f_1$ and $f_2$. This integrated result can then be compared with a threshold value to make a sorting decision. For example, the lateral size of the cell can be estimated to be less than a certain value based on the fact that the integrated result in less than the predefined threshold.

In this example, the cell size results in the illumination of the cell by optical radiation having radiofrequency modulations ranging from about 18 MHz to about 21 MHz. Hence, the difference between the maximum and the minimum modulation frequencies in the square of the fluorescence data would be about 6 MHz. If detection of cells having larger sizes that would result in difference frequencies in the square of their fluorescence data in a range of about 10 MHz to about 15 MHz were desired, a bandpass filter that would discriminate against frequencies below 10 MHz and above 15 MHz could be applied to the square of fluorescence data. In this example, the application of such a bandpass filter to the square of the fluorescence data would not result in a sufficiently large signal to indicate the presence of cells having the desired lateral sizes, as the difference modulations frequencies in the square of the fluorescence data are below 10 MHz.

The above sorting method based on cell size can have a variety of different applications, e.g., isolation by size of circulating tumor cells (CTCs).

Figure 18:
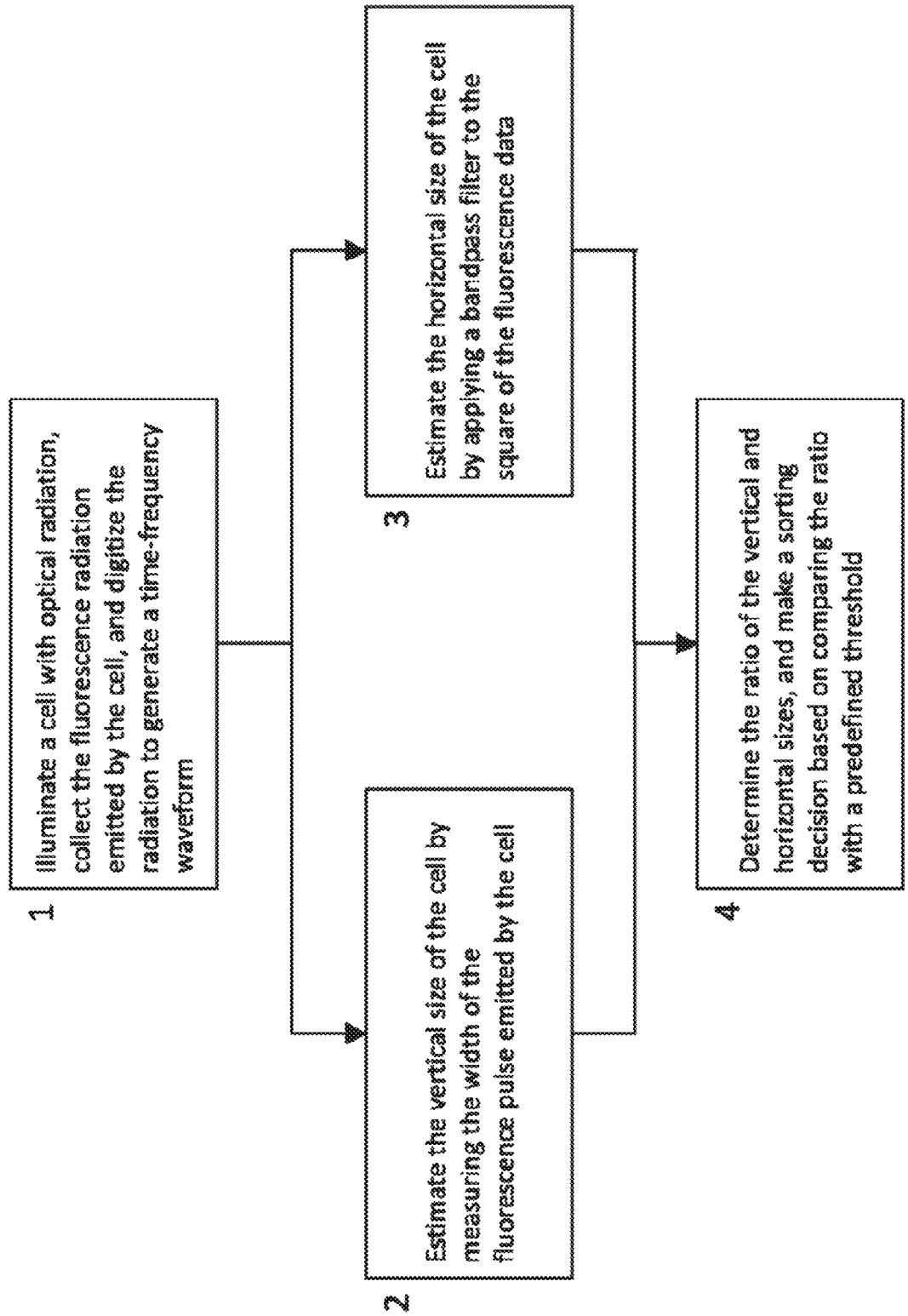
FIG. 18 is a flow chart depicting a method for sorting cells based on the cells' aspect ratio.

In another aspect, a method of sorting cells based on cells' aspect ratios is disclosed. For example, with reference to the flow chart of FIG. 18, a cell passing through an optical interrogation region is excited with radiation and fluorescence radiation emitted by the cell is collected and digitized (block 1) to generate a digitized time-frequency waveform. The digitized fluorescence data is then analyzed in a manner discussed above to estimate the vertical (along the direction of flow) cell size (block 2) and the horizontal (along a direction orthogonal to the direction of flow) cell sizes (block 3). More specifically, the vertical size of the cell can be estimated using the temporal width of a fluorescence or light scatter (or light transmitted) pulse emitted by the cell (block 2), and the horizontal size of the cell can be estimated using, for example, the method discussed above based on applying a bandpass filter to the square of the fluorescence data (block 3). At block (4), a ratio of the estimates of the cell's vertical and horizontal sizes is determined and compared with a predefined threshold to make a sorting decision with regard to that cell. For example, in some cases, if the ratio exceeds the threshold, a positive sorting decision can be made with respect to that cell.

The above sorting method based on a cell's aspect ratio can be used, e.g., in cell cycle analysis, DNA analysis, etc.

Figure 19A:
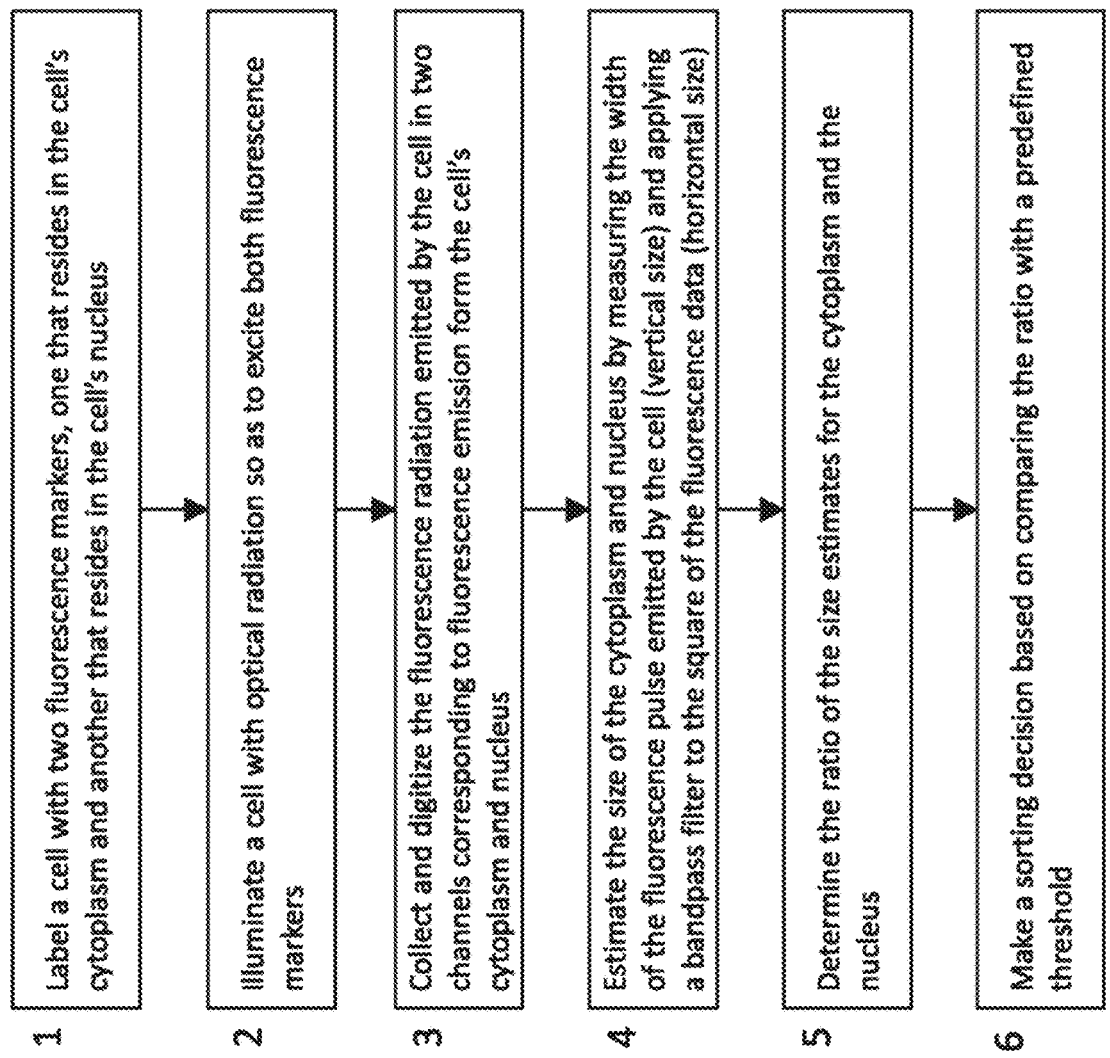
FIG. 19A is a flow chart depicting a method for estimating the ratio of the size of a cell's nucleus and the cell's cytoplasm.

In another aspect, a method of determining the ratio of the size of a cell's nucleus relative to the size of its cytoplasm is disclosed. In some embodiments, such a ratio can be employed to make a sorting decision. With reference to the flow chart of FIG. 19A, in one such embodiment, a cell is labeled (e.g., stained) with two fluorescence markers, one of which would reside on the cell's membrane (boundary of the cytoplasm) and the other can permeate the cell membrane to enter the cytoplasm and stain the cell's nucleus (e.g., via internal machinery of the cell) (block 1). Some examples of fluorescence markers that would bind to the cell membrane include any antibody tagged with a fluorophore that binds to a membrane protein, such as anti-CD45-FITC, or anti-EpCAM-PE. Other common surface proteins that can be employed for binding a fluorescence marker to the cell membrane include, for example, CD3, CD4, CD8, etc. Some examples of suitable nuclear fluorescence stains include, without limitation, Propidium Iodide, SYTO16, 7-AAD, and DAPI.

The cell is then illuminated with radiation so as to excite both types of fluorescence markers (block 2), and the emitted fluorescence is detected and digitized in two channels corresponding to fluorescence emission from the cell membrane and from its nucleus (block 3). The fluorescence data corresponding to the cell membrane is used, for example, in a manner discussed above, to obtain an estimate of the size of the cytoplasm, and the fluorescence data corresponding to the nucleus is used to obtain an estimate of the nucleus size (block 4). For example, the width of the fluorescence or light scatter pulse in each channel can be employed, e.g., in a manner discussed above, to estimate the cell size along one dimension (i.e., along the direction of flow). Further, the lateral size of the cytoplasm or the nucleus can be estimated by applying a bandpass filter to the square of the fluorescence data in the respective channel in a manner discussed above. The result of integrating this bandpass-filtered data provides a value to compare with a predefined threshold in order to sort cells that are larger or smaller than the threshold. Further, the size estimates of the cell in the two dimensions can be combined, e.g., by obtaining the square root of the sum of the squares of the vertical and horizontal size estimates, to arrive at a sort decision based upon an estimate of the total cell size.

Figure 19B:
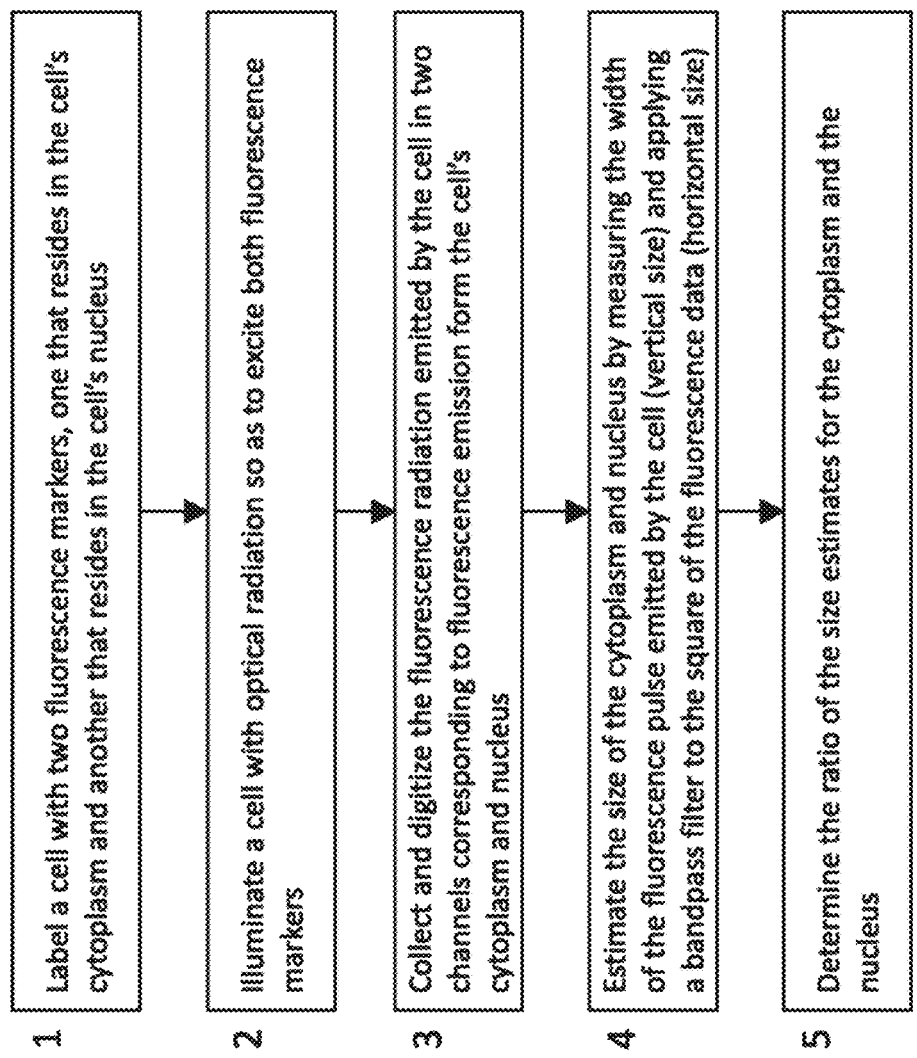
FIG. 19B is a flow chart depicting a method for sorting cells based on the estimated ratio of the size of a cell's nucleus and the cell's cytoplasm.

At block (5), the ratio of the size estimates for the cytoplasm and the nucleus is obtained, e.g., the ratio of the sizes in the vertical or the horizontal direction, or the ratio of the combined sizes. With reference to the flow chart of FIG. 19B, in some embodiments, the ratio of the size of the cell's nucleus relative to the size of its cytoplasm, which can be determined, e.g., in a manner discussed above and represented in blocks (1)-(5) of the flow chart of FIG. 19B, can be used to make a sorting decision. For example, the ratio can be compared with a predefined threshold to make a sorting decision (block 6). By way of example, if the ratio exceeds the threshold, a positive sorting decision is made (i.e., the cell is selected).

By way of example, the above sorting method based on the nuclear-to-cytoplasm size ratio can be used in classification of circulating tumor cells.

In another aspect, a method of estimating cellular granularity of fluorescent radiation emitted from cells (fluorescence punctateness) is disclosed, which in some embodiments can be used for sorting the cells. In other words, a sorting decision can made based on whether the emitted fluorescent radiation from a cell can be characterized as emanating from a diffuse intracellular distribution of emitting centers, or can be characterized as emanating from emitting centers that are not diffusely distributed within the cell.

Figure 20A:
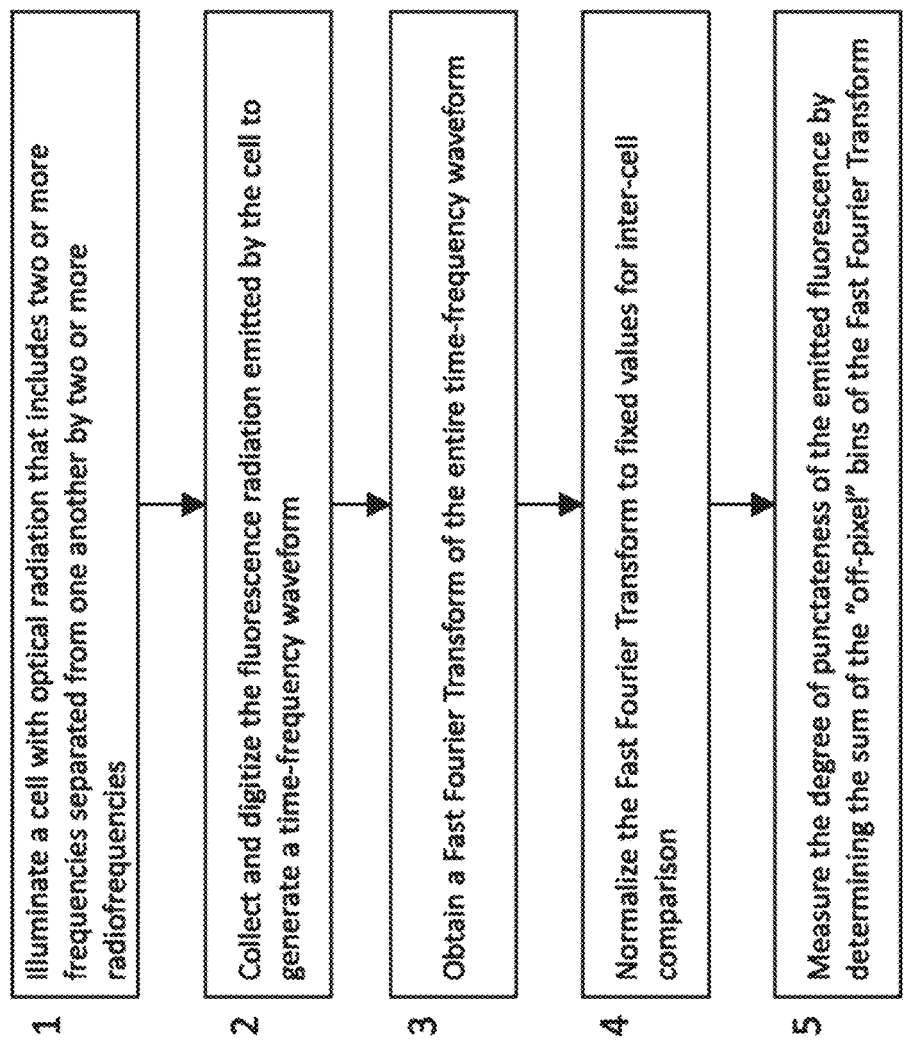
FIG. 20A is a flow chart depicting a method for estimating cellular granularity of fluorescence radiation emitted from cells.
Figure 21:
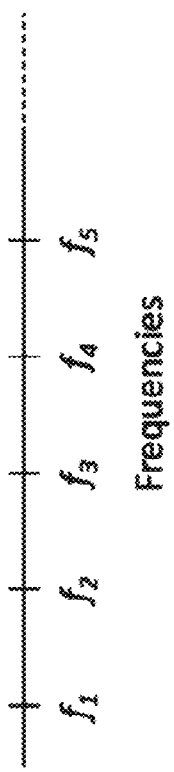
FIG. 21 schematically shows modulation frequencies used to modulate an optical beam employed in the method described in the flow chart of FIG. 24 for eliciting fluorescence radiation from the cells.

More specifically, with reference to the flow chart depicted in FIG. 20A, in one embodiment, a cell having one or more exogenous and/or endogenous fluorescence markers is illuminated with optical radiation having two or more optical frequencies separated from one another by one or more radiofrequencies so as to elicit fluorescence radiation from the marker(s) (block 1). Similar to the previous embodiments, in some cases, the optical beam can include a plurality of angularly or spatially separated beamlets, each of which has a radiofrequency shift relative to another. By way of example, with reference to FIG. 21, in an illustrative, exemplary embodiment the optical radiation beam can include modulation frequencies $f_1$, $f_2$, $f_3$, $f_4$, $f_5$, which can span, e.g., from 10 MHz ($f_1$) to 15 MHz ($f_5$) with a separation of 0.5 MHz. As discussed in more detail below, the punctateness of the emitted fluorescence radiation can be estimated by the extent in which the emitted fluorescence radiation exhibits modulation frequencies other than those employed to modulate the optical beam (e.g., other than $f_1$, $f_2$, $f_3$, $f_4$, $f_5$, in this embodiment). The other frequencies, which can be frequencies between the frequencies used to modulate the optical beam, are herein referred to as "off-pixel frequencies." In other words, the "leakage" of fluorescence power into off-pixel frequencies is indicative of the degree of punctateness of the emitted fluorescence; the more the leakage the more is the punctateness of the emitted fluorescence.

Referring again to the flow chart of FIG. 20A, the fluorescent radiation can be collected and digitized to generate a time-frequency waveform (block 2). At block (3), a Fourier transform, e.g., a Fast Fourier Transform (FFT), of the entire waveform is obtained. Subsequently, the generated FFT is normalized to fixed values for inter-cell comparison (block 4), e.g., by dividing the time-domain waveform by its maximum value and then re-scaling the waveform by a desired constant. The sum of the "off-pixel" bins of the FFT (i.e., the bins corresponding to frequencies between the modulation frequencies present in the illuminating optical radiation) is determined (block 5). The sum is indicative of the degree of "leakage" of fluorescence power to off-pixel frequencies, and hence a measure of the degree of punctateness of the emitted fluorescent radiation.

Figure 20B:
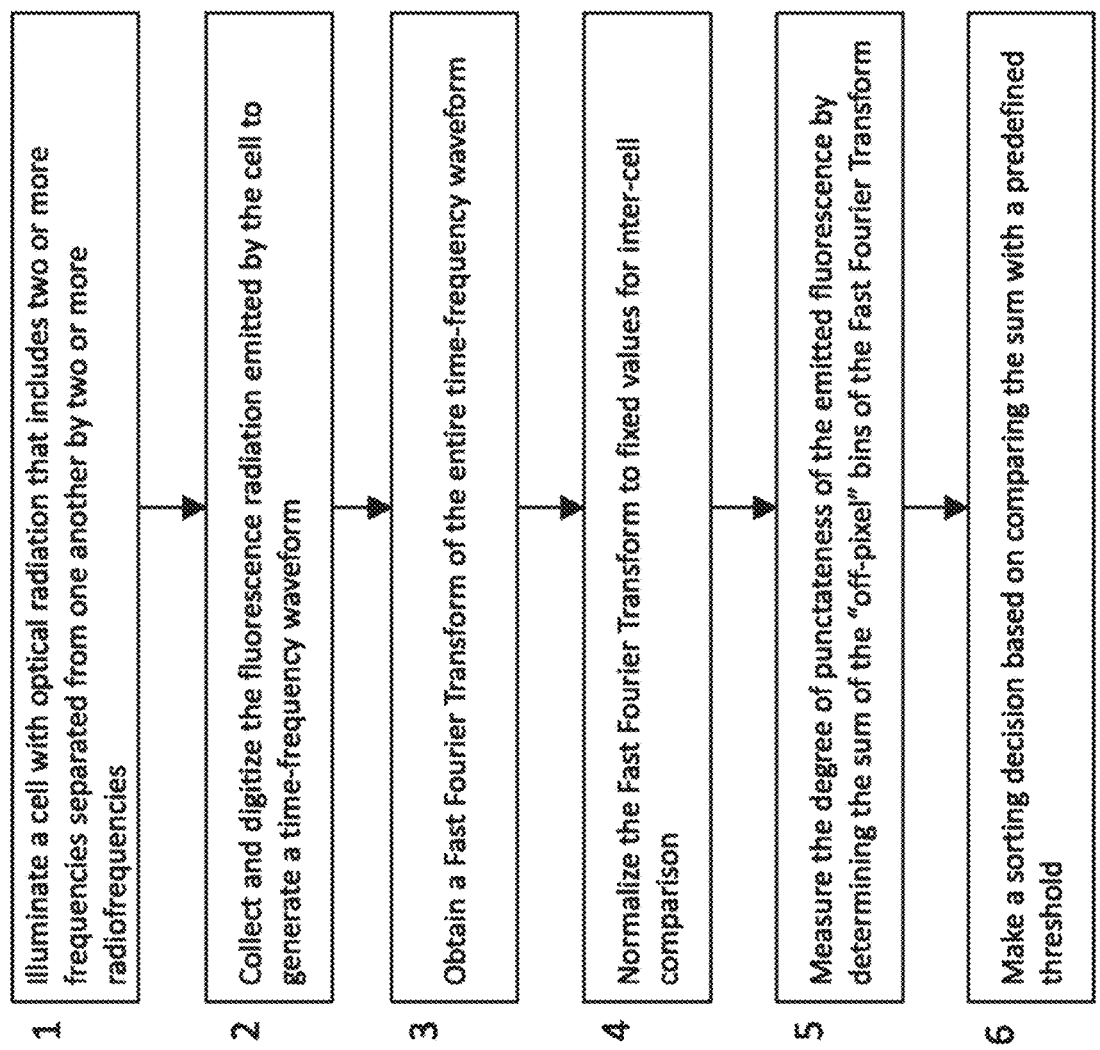
FIG. 20B is a flow chart depicting a method for sorting cells based on estimating cellular granularity of fluorescence radiation emitted from the cells.

With reference to FIG. 20B, in some embodiments, the measure of the degree of punctateness of the emitted fluorescent radiation, which can be determined in a manner discussed above and represented in blocks (1)-(5) of the flow chart of FIG. 20B, can be used for sorting the cells. In particular, at block (6), the sum of the "off-pixel" bins of the FFT, which is indicative of the degree of "leakage" of fluorescence power to off-pixel frequencies, can be compared with a predefined threshold to make a sorting decision. For example, when it is desired to sort cells exhibiting a relatively high degree of fluorescence punctateness, a cell is sorted (selected) if the sum is greater than the threshold. Alternatively, when it is desired to sort cells exhibiting diffuse fluorescence, a cell is sorted if the sum is less than the threshold.

Such sorting of cells based on the analysis of the emitted fluorescent radiation can be employed in a variety of applications, such as spot counting, fluorescence in-situ hybridization (FISH), intracellular transport and localization, and droplet-based single-cell analysis.

Figure 22:
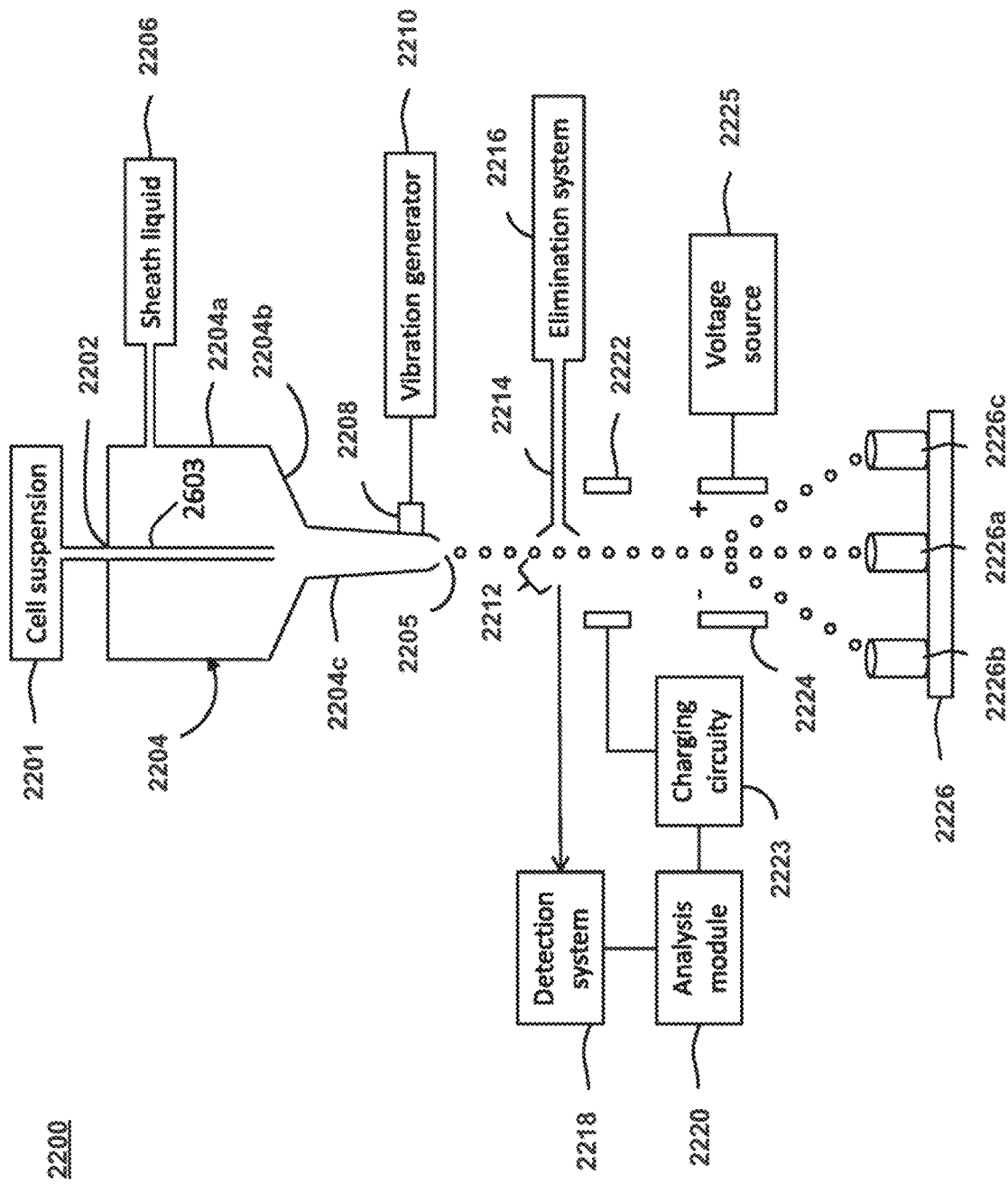
FIG. 22 schematically depicts a sorting system that incorporates the present teachings for sorting cells.

The above methods for making sorting decisions for particles (e.g., cells flowing in a flow cytometry system) can be implemented in a variety of ways. By way of example, FIG. 22 schematically depicts an exemplary system 2200 for sorting cells, which can employ the present teachings for making a sorting decision. The system 2200 can include a container 2201 for storing a suspension fluid in which a plurality of cells is suspended. The cell suspension container 2201 is fluidly coupled via an inlet 2202 to a sample conduit 2203, which can be formed, for example, of a rigid metal such as stainless steel. The sample conduit 2203 is disposed within a vessel 2204 that includes an upper cylindrical portion 2204a that extends, via a tapered portion 2204b, to a lower cylindrical portion 2204c having a smaller diameter, which includes a nozzle 2205 at a distal end thereof. The vessel 2204 is fluidly coupled to a sheath fluid source 2206. An acoustic vibrator 2208 (e.g., a piezoelectric driver) is coupled to the nozzle and is configured to cause vibration of the nozzle when energized by a generator 2210. By way of example, the vibration frequency can be about 60 kHz, though other vibration frequencies can be also used.

In use, the suspension fluid stored in the container 2201 is introduced via the inlet 2202 into the conduit 2203. A thin flow of the fluid containing cells that exits the container 2203 is entrained by the sheath fluid and is carried to the nozzle 2205. The vibratory motion of the nozzle can be configured in a manner known in the art to split the flow through the nozzle into a plurality of droplets D each of which contains a single cell particle. At least some of the cells are associated with one or more endogenous and/or exogenous fluorophores, which can emit fluorescent radiation in response to illumination by an excitation radiation. A wide range of fluorophores can be used. In some cases, a fluorophore can be attached to an antibody that recognizes a target (e.g., a receptor) on a cell. In some cases, a fluorophore can be attached to a chemical entity that has an affinity for the cell membrane or another cellular structure, e.g., the cell's nucleus. Further, in some cases, a cell can be labelled with a combination of different fluorophores.

With continued reference to FIG. 22, as each cell passes through an interrogation region 2212 it is illuminated by a laser beam 2214 generated by an illumination system 2216 to elicit fluorescent radiation from one or more fluorophores associated with the cell. As discussed above, the laser beam can include a plurality of optical frequencies that are shifted relative to one another by one or more radiofrequencies. By way of example, the optical beam can be in the form of a plurality of angularly or spatially separated beamlets having radiofrequency shifts relative to one another. The fluorescent radiation emitted from the cell can be detected by a detection system 2218, which can include one or more photodetectors. The detected fluorescent can be analyzed by an analysis module 2220, in a manner discussed above, to make a sorting decision regarding that cell.

By way of example, the illumination the detection systems can be those discussed above, e.g., in connection with FIGS. 1-9. It should, however, be understood that the practice of the present teachings for sorting particle is not limited to the use of any particular illumination and detection system. Rather, a variety of different systems can be employed so as long as they provide the requisite data (e.g., fluorescence and/or scatter data) for use in the above methods for making sorting decisions.

Referring again to FIG. 22, the system 2200 further includes a charging collar 2222, which is energized by a charging circuitry 2223, which is in turn under the control of the analysis module 2220. The charging collar can impart a positive, or a negative charge to a cell droplet as it passes through the collar. Alternatively, the collar can allow a cell droplet to pass through without imparting a charge thereto.

More specifically, the analysis module 2220 can employ the above teachings to make a sorting decision regarding a cell. Based on that decision, the analysis module can determine whether the cell droplet needs to be charged, and if so, which charge polarity should be imparted to the cell. The analysis module can then control the charging circuitry 2223 to impart, via the collar 2222, the requisite charge to the cell droplet. The cell then passes through a gap between a pair of deflection plates 2224, which are disposed downstream of the collar 2222. A voltage source 2225 applies a voltage to at least one of the plates 2224 to establish an electric field between the plates. The electric field can deflect the path of the negative and positive cell droplets along different directions so that they can be collected, respectively, by tubes 2226b and 2226c of the cell collector 2226. The cells that are not electrically charged by the collar 2222 are not deflected and are captured by the tube 2226a of the cell collector.

Figure 23:
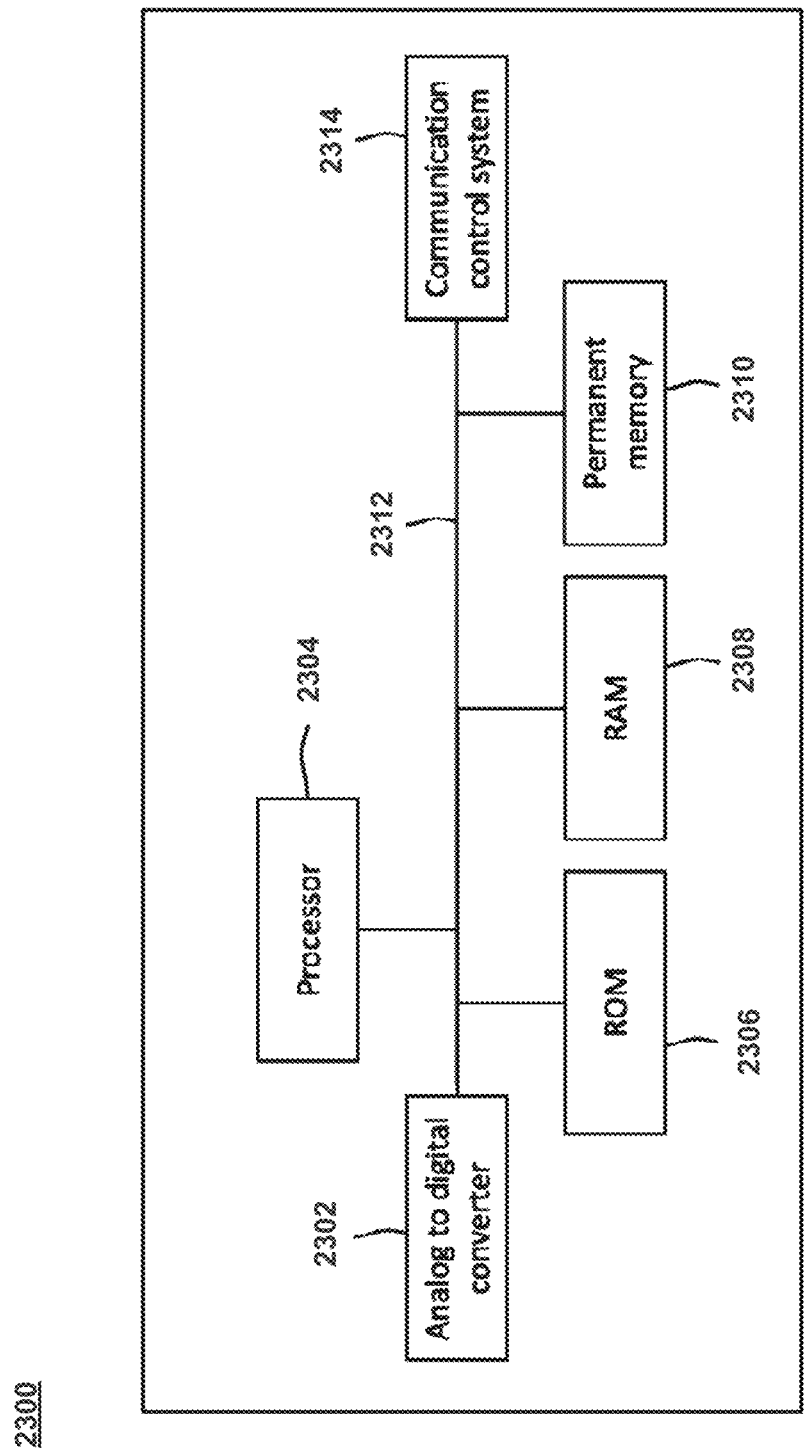
FIG. 23 schematically depicts an exemplary implementation of the analysis/control module employed in the system of FIG. 22.

The analysis/control modules discussed herein, such as the analysis/control module 2220, can be implemented in a variety of different ways in hardware, firmware and/or software using techniques known in the art and in accordance with the present teachings. By way of example, FIG. 23 schematically depicts an exemplary implementation 2300 of the analysis/control module 2220, which includes an analog-to-digital converter 2302 for receiving fluorescence signal(s) from the detection system 2218 and digitizing the signal(s) to generate digitized fluorescence data. The analysis/control module 2300 can further include a processor 2304 for processing the fluorescence data in accordance with the present teachings to arrive at a sorting decision regarding a cell under interrogation. The analysis/control module 2300 can also include ROM (read only memory) 2306, RAM (random access memory) 2308 and permanent memory 2310. A communication bus 2312 facilitates communication among various components of the analysis module. The memory modules can be used to store instructions for analyzing the fluorescence signal(s) and the analysis results. For example, in some embodiments, instructions for analyzing the fluorescence data to arrive at a sorting decision in accordance with the present teachings can be stored in the ROM 2306. The processor 2304 can employ these instructions to operate on the digitized fluorescence data stored in RAM 2308 so as to determine a sorting decision. In some embodiments, the processor can be implemented as an ASIC (application specific integrated circuit) that is configured to perform the instructions according to the present teachings for operating on fluorescence data to arrive at a sorting decision. In this embodiment the analysis/control module 2300 can further include a communication/control module 2314 for sending appropriate signals to the charging circuitry based on the sort decision so as to impart suitable charge to a cell under interrogation.

As discussed above, the methods according to the present teachings operate on temporal fluorescence data to arrive at a sort decision for a particle (e.g., a cell) without the need to form a pixel-by-pixel fluorescence image of the cell. This in turn allows sorting cells with a low latency, e.g., less than about 100 microseconds, which in turn allows sorting cells at a high rate. For example, the sorting methods according to the present teachings can allow sorting cells at a rate of equal to or greater than 1000 cells per second, e.g., in a range of about 1000 to about 100,000 cells per second.

Though not limited to any particular illumination or detection technology, as noted above, in some embodiments the cell sorting methods according to the present teachings can be effectively used in flow cytometry systems that employ frequency domain multiplexing to excite a row of pixels, each "tagged" at a unique radiofrequency generated, for example, by beating of two frequency-offset baser beams. Using frequency-domain multiplexing, fluorescent (or scattered) radiation from hundreds of pixels in a single row of an image can be detected and read out using, for example, a single photomultiplier tube (PMT) for each fluorescent color or scattered direction. Since the excitation of each pixel in a row of the image is modulated at a unique beat frequency, the pixel rate scales with the total RF bandwidth of the system, which can provide shot noise-limited sensitivity at pixel rates of more than 100 MHz. As discussed above, the sorting methods according to the present teachings can employ the image data, which is encoded in a time-frequency format, to perform sorting decisions without actually computing the image.

Further, the above system can be employed to sort particles (e.g., cells) based on the scattered radiation emanating from the particles in response illumination. The scattered radiation can be detected and analyzed, e.g., in a manner discussed above, to arrive at a sort decision.

By way of further examples, the following U.S. patents provide information regarding sorting systems that can be modified in accordance to the present teachings to practice the sorting methods and systems disclosed herein: U.S. Pat. No. 3,380,584 entitled "Particle Separator," U.S. Pat. No. 9,034,259 entitled "Flow Cytometer and Flow Cytometry," and U.S. Pat. No. 7,417,734 entitled "System and Process for Sorting Biological Particles," each of which is herein incorporated by reference in its entirety.

By way of further elucidation, Appendix A of priority application Ser. No. 62/822,789 filed Mar. 22, 2019, the disclosure of which is herein incorporated by reference, provides additional information regarding various aspects of the present teachings.

Those having ordinary skill in the art will appreciate that various changes can be made without departing from the scope of the present teachings. In particular, various features, structures, or characteristics of embodiments discussed above can be combined in a suitable manner. For example, the detection systems discussed in connection with one embodiment may be used in another embodiment.

Particle Characteristics

As discussed above, in some embodiments, two or more beamlets with a radiofrequency amplitude modulation illuminate a sample at spatially-distinct locations. The interaction between the sample and each beamlet can produce optical at least one of scattered, transmission, and fluorescence emission signals, each of which is amplitude-modulated with the beamlet's corresponding radiofrequency. The collected signal can be represented as the sum of the contributions from each modulated beamlet:

$$S(t) = \Sigma_i P_i(t) \cdot (1 + A_m \cos(\omega_i t + \phi_i)) \quad \text{Eq. (3)}$$

where S(t) represents the collected signal, $P_i(t)$ represents the time-dependent scattered, transmission, or fluorescence emission signal associated with the ith beamlet, $A_m$ represents the modulation depth of the beamlet, and $\omega_i$ and $\phi_i$ represent the angular frequency and phase of the radiofrequency modulation of the beamlet, respectively. An image representation of the particle can be derived by assigning each beamlet to a different column of the image, and each moment in time to a different row of the image. This image representation is connected to the collected signal via the Fourier Transform:

$$Im(x,y) = R \cdot W \cdot F \cdot S(t) \quad \text{Eq. (4)}$$

where F is a matrix implementing the short-time Fourier Transform, W is a matrix that maps Fourier components to image pixels, and R is a matrix that performs any desired linear image-domain post-processing such as filtering, background subtraction, and vignette correction. Any linear feature of a particle can be represented by a matrix multiplication on an image. Therefore, for a matrix M that computes any desired linear feature, the feature can be computed directly, i.e., without the need to first compute an image, from collected signals via:

$$M \cdot Im(x,y) = M \cdot R \cdot W \cdot F \cdot S(t) = Q \cdot S(t) \quad \text{Eq. (5)}$$

$$Q = M \cdot R \cdot W \cdot F \quad \text{Eq. (6)}$$

where Q is a matrix representing the transformation from the present particle representation to the desired linear feature. Hence, any linear feature can be computed by initially computing the matrix Q, e.g., offline in a pre-processing step, then performing a dot product as indicated in Eq. (5), e.g., online, to extract the desired feature. In many embodiments, for all features, it is desired to also subtract the contribution of background signal to the feature. This process can be summarized as follows:

---

Compute: $Q = M \cdot R \cdot W \cdot F$
Compute: $Q_{bkg} = M \cdot R \cdot W_{bkg} \cdot F$
While data is being collected:
   If a particle is detected:
     Compute: $D = Q \cdot S(t)$
   Else:
     Compute: $D_{bkg}(i) = Q_{bkg} \cdot S(t)$
Compute: $D_{bkg} = \text{mean}(D_{bkg}(i))$
Yield: $D - D_{bkg}$

---

Figure 24:
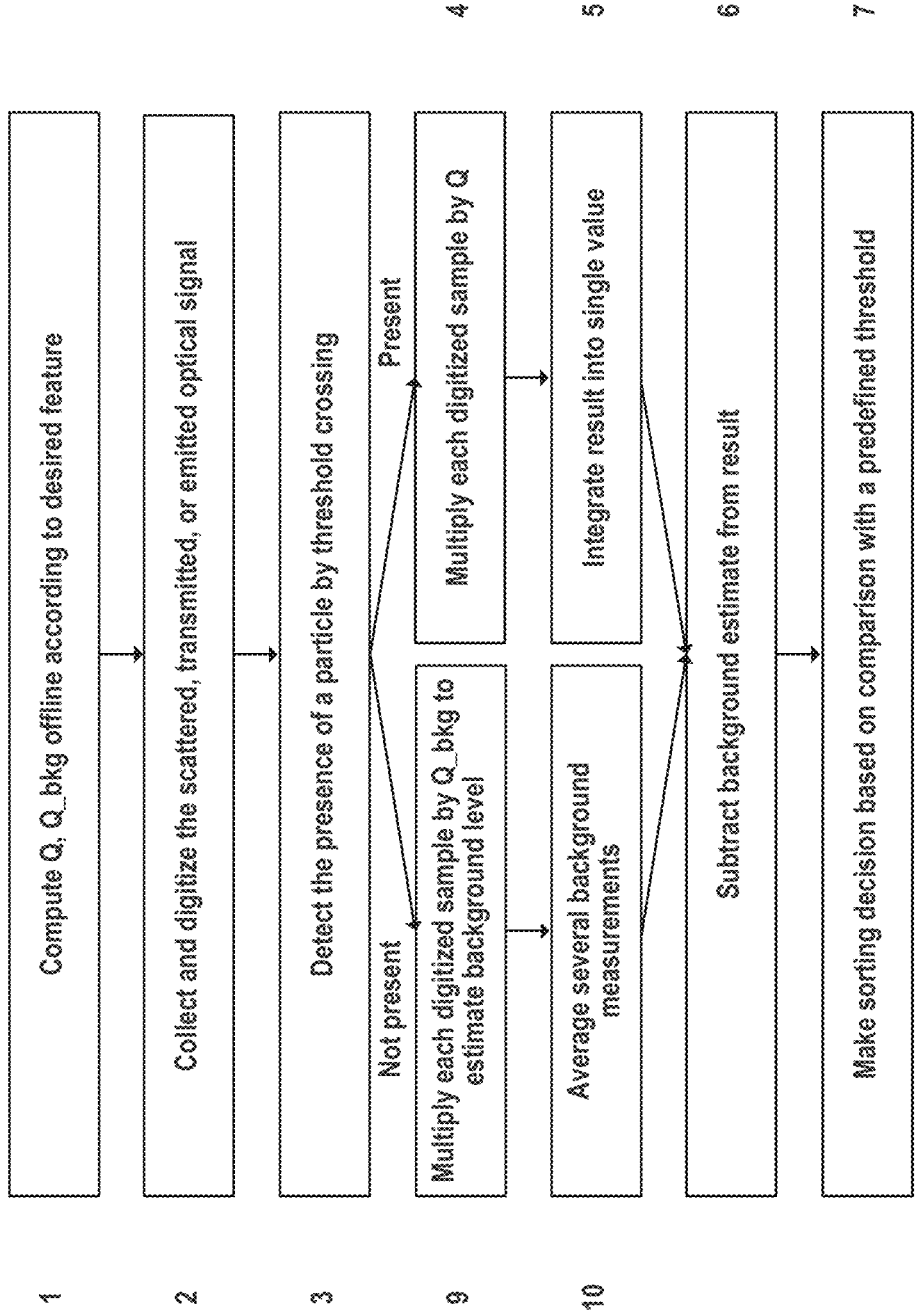
FIG. 24 is a flow depicting an exemplary method for determining a characteristic or a particle and using that characteristic to make a sorting decision in accordance with an embodiment.

As discussed above, in some embodiments, one or more computed features of a particle can be employed for making a sorting decision regarding that particle. By way of a further example, FIG. 24 shows a flow chart depicting a sorting method. At block (1), the above Q, and $Q_{-bkg}$ matrices can be computed based on a desired particle feature (characteristic). Subsequently, scattered, transmitted or emitted optical signal, e.g., from a flow cell of a flow cytometer illuminated with radiofrequency-modulated optical radiation, can be collected and digitized (block 2). The signal can be compared with a threshold crossing to determine whether the signal is from a particle, i.e., whether a particle was present (block 3). If it is determined that a particle was present, each digitized sample signal is multiplied by Q (block 4) followed by integrating the result into a single value (block 5). A background signal is subtracted from the integrated value (block 6) to obtain an estimate of the desired feature (characteristic) of the particle. A sorting decision can be made via comparison of the estimate of the feature with a threshold (block 7). With continued reference to the flow chart of FIG. 24, one or more digitized signals obtained in absence of a particle, can be multiplied by $Q_{-bkg}$ (block 8), and several background measurements can be averaged to obtain the background estimate employed in the block (6).

In some embodiments, various moments of a received signal can be used to obtain information about the spatial distribution of scattered, transmitted, or emitted radiation. Image moments are a class linear image features representing the weighted sum of pixels according to their distance from an arbitrary origin, taken to some arbitrary power:

$$M_{m,n} = \Sigma (x-\bar{x})^m (y-\bar{y})^n Im(x,y) = M \cdot Im(x,y) \quad \text{Eq. (7)}$$

Each image moment encodes different information about the spatial distribution of scattered, transmitted, or emitted light. Higher-order moments weigh pixels more according to their distance from the origin, with each moment providing different information about the distribution of signal. In various embodiments, all of these features can be computed directly from the measured signal S(t) by pre-computing an appropriate Q.

Spatial Fourier components can be computed in the same way, with M defined as follows:

$$M(u,v) = \exp(-j2\pi(ux+vy)) \quad \text{Eq. (8)}$$

The desired components can be selected before an experiment, and a separate Q can be pre-computed for each one. By of example, Fourier components can be used to determine if a particle is in focus of illuminating radiation.

Some image features involve nonlinear transformations on the data prior to feature extraction. For a subset of such features, it is possible to represent them as nonlinear combinations of linear features. Computing such features can involve first computing multiple features as in the previous section in parallel, then combining the results in a nonlinear way. There are many useful image features that can be expressed by nonlinear combinations of image moments. For example, the center of mass of the pixels can be calculated by the ratio of the first- and zero-order moments:

$$\text{Center of Mass} = \frac{M_{1,0}}{M_{0,0}} \qquad \text{Eq. (9)}$$

Several other particle characteristics can be represented this way. A non-exhaustive list is in Table 1 below.

TABLE 1

| Extracted Feature | Nonlinear combination of linear features |
|---|---|
| Center of Mass | $\frac{M_{1,0}}{M_{0,0}}$ |
| Orientation | $\frac{1}{2}\arctan\frac{2\left(M_{1,1} - \frac{M_{1,0}M_{0,1}}{M_{0,0}}\right)}{M_{2,0} - \frac{M_{2,0}^2}{M_{0,0}} - M_{0,2} + \frac{M_{0,2}^2}{M_{0,0}}}$ |
| Eccentricity | $M_{2,0} - \frac{M_{2,0}^2}{M_{0,0}^2} + M_{0,2} - \frac{M_{0,2}^2}{M_{0,0}^2} - \sqrt{4\left(M_{1,1} - \frac{M_1 M_{0,1}}{M_{0,0}^2}\right)^2 + \left(M_{2,0} - \frac{M_{2,0}^2}{M_{0,0}} - M_{0,2} + \frac{M_{0,2}^2}{M_{0,0}}\right)^2}$ $M_{2,0} - \frac{M_{2,0}^2}{M_{0,0}^2} + M_{0,2} - \frac{M_{0,2}^2}{M_{0,0}^2} + \sqrt{4\left(M_{1,1} - \frac{M_{1,0}M_{0,1}}{M_{0,0}^2}\right)^2 + \left(M_{2,0} - \frac{M_{2,0}^2}{M_{0,0}} - M_{0,2} + \frac{M_{0,2}^2}{M_{0,0}}\right)^2}$ |
| Central Moments (Second-order) | $M_{2,0} - \frac{M_{1,0}^2}{M_{0,0}}, M_{0,2} + \frac{M_{0,1}^2}{M_{0,0}}$ |

In some embodiments, central second-order moments can be used to discriminate doublets. Particles with high second-order moments in scattered or transmitted light signals indicate a larger distribution of signal.

Colocalization and Similarity

In some embodiments, similarity between a particle and a reference can be computed the same way as co-localization. In the co-localization case, the two waveforms correspond to different detectors looking at the same particle; in the similarity case, the two waveforms correspond to the same detector looking at two different particles. An exemplary algorithm for detecting similarity between a particle and a reference is summarized below:

Let R represent the waveform corresponding to a reference particle, Filt be a high-pass or band-pass filter that passes only modulated frequencies, and N be the number of pixels in an image representation of the reference particle. The algorithm will then include:

Compute $\bar{R} = \frac{M_{0,0}(R)}{N}$,

Compute $R' = Filt(R)$,

Compute $R_2 = \|R'\|^2$,

For each incoming waveform S corresponding to a particle under study:

Compute $\bar{S} = \frac{M_{0,0}(S)}{N}$

Compute $S' = Filt(S)$

Compute $D = S' \cdot R'$

Compute $S_2 = \|S'\|^2$

Return $$\frac{D - \bar{S}\bar{R}N}{(R_2 - \bar{R}^2 N)(S_2 - \bar{S}^2 N)}$$

as a measure of the similarly of the particle with the reference particle.

Spectral Unmixing

Disclosed herein include systems, devices, and methods for performing compensation or spectral unmixing of images generated from a FIRE-enabled imaging flow cytometer. Detecting the fluorescence radiation emitted by one or more fluorophores after excitation by the combined beam 49 can be referred to as fluorescence imaging using radiofrequency-multiplexed excitation (FIRE). Fluorescence radiation, emission, signal, or waveform detected by a detector configured to (e.g., using band pass filters) detect the fluorescence radiation of one fluorophore or dye can include fluorescence emission of another fluorophore because the spectra of the fluorescence emissions of the two fluorophores may overlap spectrally. Spectral unmixing can include phase-sensitive analysis based on fluorescence lifetime measurement. Spectral unmixing can be implemented on a field programmable gate array (FPGA) for cell sorting applications, for example.

Fluorescence signals of waveforms have different phases when the fluorophores have different lifetimes. Fluorescence signals with different phases do not add together in a straightforward manner in the real space, but rather add in the complex space (with real and imaginer components). In some embodiments, spectral unmixing can include performing analysis of the fluorescence signals in the complex space to, for example, the different phases of the fluorophores. Spectral unmixing can include performing analysis of the fluorescence signals in the complex space to account for various systematic effects in the optics and electronics that are inherent in a FIRE system (e.g., on a per channel basis). The detection system of a flow cytometer can include multiple photodetectors to detect fluorescence signals and generate multiple channels of fluorescence signals as described with reference to FIGS. 7A-7B. If spectral unmixing is applied to a FIRE image generated from the fluorescence signals of each channel (e.g., a FIRE image generated from the fluorescence signals detected by a photodetector) on a per pixel basis, or if no spectral unmixing is performed, then the image can include artifacts stemming from the differences in phase contributions of different fluorophores whenever those fluorophores have different fluorescence lifetimes.

Figure 25:
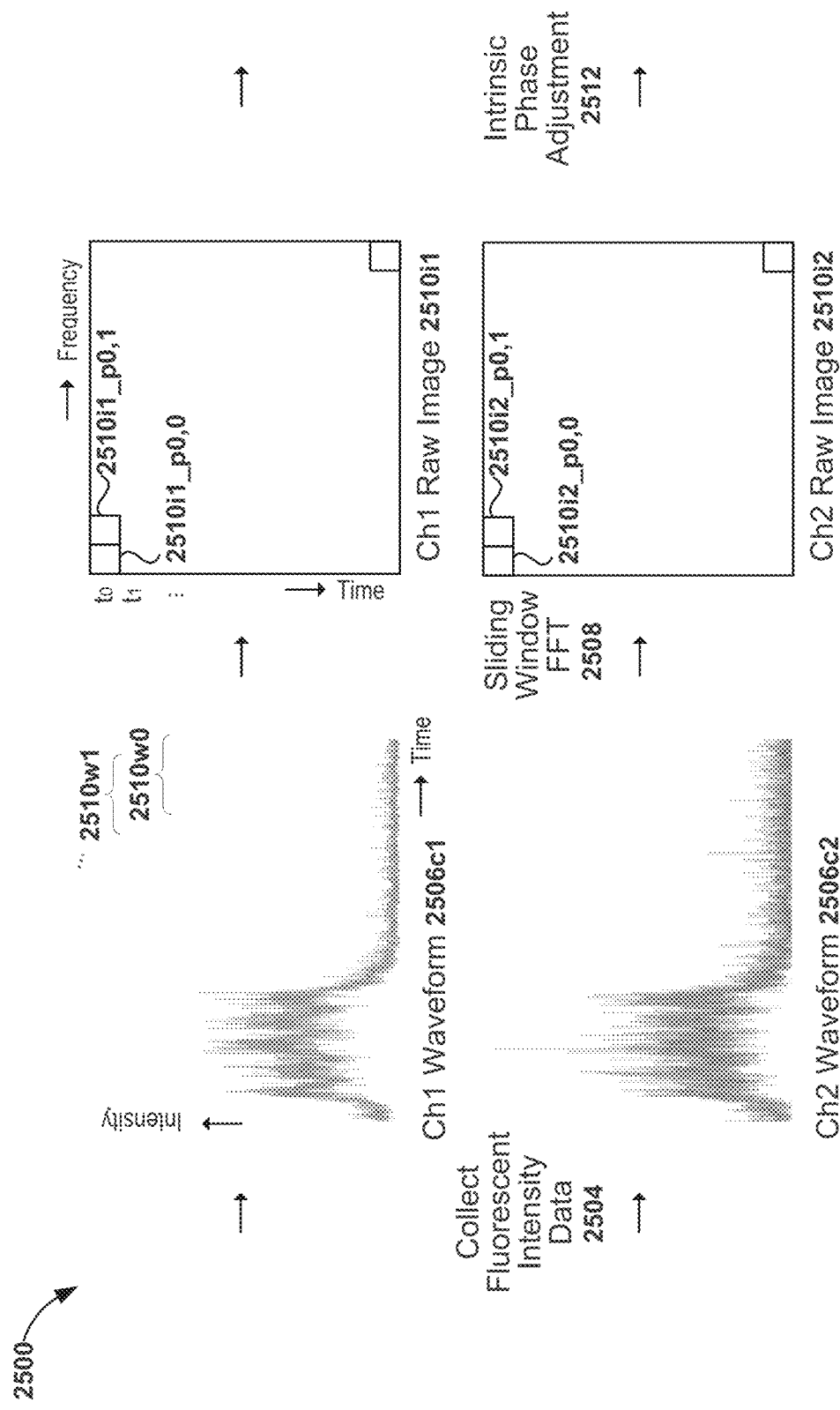
FIG. 25 is a non-limiting exemplary schematic illustration of spectral unmixing.
Figure 25:
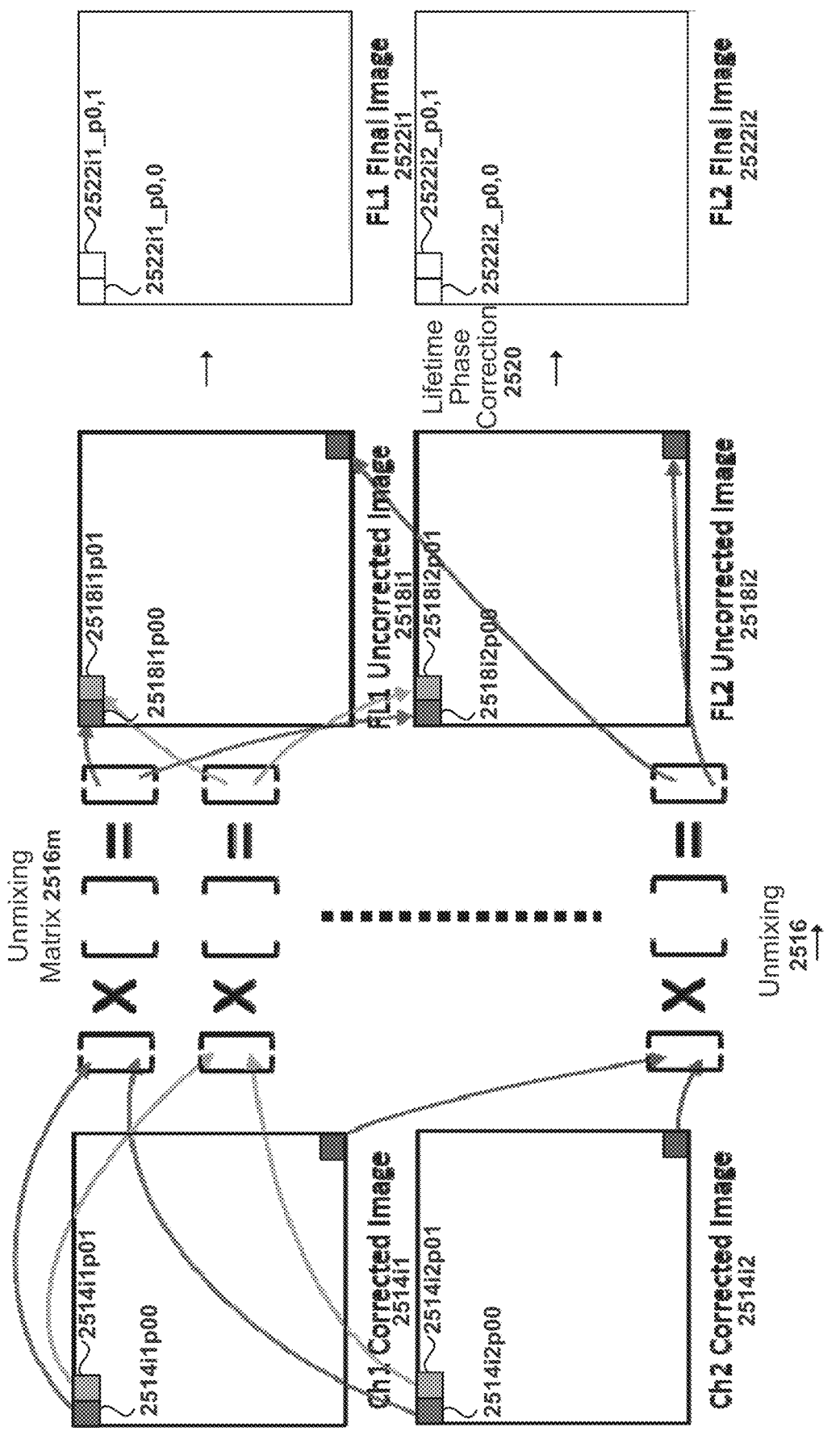

FIG. 25 is a non-limiting exemplary schematic illustration of a spectral unmixing method 2500. At action 2504, fluorescence signals of multiple channels detected by multiple photodetectors can be received. For example, antibodies associated with (e.g., bind to, and conjugated with) different fluorophores can bind to a cell. Fluorescence signals of the fluorophores can be detected by the multiple photodetectors. For example, one photodetector can be configured to detect the fluorescence signals for each fluorophore. FIG. 25 shows two plots $2506p11$, $2506p2$ of FIRE waveforms $2506c1$, $2506c2$ of two channels. The time dimension of the waveforms $2506c1$, $2506c2$ is shown on the x-axis of each plot $2506p11$, $2506p2$. The intensity of the FIRE waveforms $2506c1$, $2506c2$ is shown on the y-axis of each plot $2506p1$, $2506p2$. Each FIRE waveform $2506c1$, $2506c2$ can contain signals from multiple fluorophores in each channel, for example, due to spectral overlap of each fluorophore with multiple channels. The spectral overlap can lead to images (e.g., the images $2510i1$, $2510i2$) with contributions from fluorophore other than the one desired or of interest for the channel. Compensation on the images can be performed in such a way that the resultant images (e.g., the images $2522i1$, $2522i2$) each is (or is mostly) a result of one fluorophore alone. The waveforms $2506c1$, $2506c2$ detected are sensitive to the phases of the fluorophores.

At action 2508, Fourier transform (FT), such as a sliding window fast Fourier transform (FFT) or discrete Fourier transform (DFT), can be used to generate the raw FT image $2510i1$, $2510i2$, for each channel. Each raw image $2510i1$, $2510i2$ can be an array (e.g., a two-dimensional array) of pixels $2510i1p00$, $2510i1p01$, $2510i2p00$, $2510i2p01$ of complex values in the frequency space (e.g., in the Fourier space). The sliding windows $2510w1$, $2510w2$ can be overlapping as illustrated or not. Imaging can be done through complex Fourier analysis of the detected waveforms $2506c1$, $2506c2$. The images generated $2510i1$, $2510i2$ can have complex values and can be phase sensitive (e.g., sensitive to the phases of the fluorophores). One dimension of the images generated $2510i1$, $2510i2$ can correspond to the different frequency bins of FFT or DFT. The other dimension of the images generated $2510i1$, $2510i2$ can correspond to the time dimension of the sliding window FFT or DFT.

At action 2512, intrinsic phase adjustment can be performed. In some embodiments, this phase adjustment can minimize (e.g., eliminate) phase contributions from the optics and electronics that vary from channel to channel. To perform compensation or unmixing in the image space, phase contributions from the optical and electronic differences between channels can first be accounted for by, for example, multiplying the raw FT images by the channel phase adjustments. The resultant set of intrinsic phase corrected images $2514i1$, $2514i2$ can be complex valued. One set of signal phase corrections (for correcting signal phases) specific to each readout channel of the flow cytometer can be used for intrinsic phase adjustment. The channel phases can incorporate, or include, the brightfield phases, calibration phases, and phase offset. The channel phase adjustments can correct, or account for, one or more channel phases.

At action 2516, an unmixing operation can be performed for every pixel $2514i1p00$, $2514i1p01$, $2514i2p00$, $2514i2p01$ of the images $2514i1$, $2514i2$ using an unmixing matrix $2516m$ to generate unmixed images $2518i1$, $2518i2$. Compensation or unmixing can be performed for corresponding pixels (such as pixels $2514i1p00$, $2514i2p00$, and pixels $2514i1p01$, $2514i2p01$) of the intrinsic phase corrected images $2514i1$, $2514i2$. For example, for two channels of images $2514i1$, $2514i2$, an unmixing matrix $2516m$ can have a size of 2×2. The unmixing matrix $2516m$ can be applied to the corresponding pixels (such as the pixels $2514i1p00$, $2514i2p00$ and the pixels $2514i1p01$, $2514i2p01$) of the images $2514i1$, $2514i2$ to generate the values of the corresponding pixels (such as the pixels $2518i1p00$, $2518i2p00$ and the pixels $2518i1p01$, $2518i2p01$) of the unmixed images $2518i1$, $2518i2$. The unmixing operation on the corresponding pixels can be performed sequentially or in parallel. The unmixed images $2518i1$, $2518i2$ can be considered images of the fluorophores (or images generated from fluorescence emissions of the fluorophores) without any spectral mixing (or with minimal or reduced spectral mixing).

The unmixing operation can depend on the type of unmixing performed. For example, the unmixing operation can be based on compensation of area values. The compensation or unmixing can be performed based on area or height data on complex image values. The unmixing matrix $2516m$ can be as derived by hand or using any automatic compensation or unmixing procedure. The unmixing matrix $2516m$ can account for differences in signal intensity, due to different fluorescence lifetimes of fluorophores, for each carrier frequency (e.g., the frequency of the reference laser beam or the local oscillator beam used for eliciting the fluorescent emission of each fluorophore).

At action 2520, lifetime phase correction can be performed. After unmixing is performed on every pixel of the images, lifetime correction can be applied for each fluorophore to generate lifetime corrected images with pixels having complex values. This adjustment can correct for the change in phase that is due to the lifetime of the fluorescence dye. One set of "lifetime corrections" can be used for each fluorophore. These can be derived from the fluorescence lifetime of each fluorophore, for example, using a known value or from computation of collected sample data.

In some embodiments, the real part of the complex number of each pixel can used to generate the value of the pixel $2522i1p00$, $2522i1p01$, $2522i2p00$, $2522i2p01$ of the final image $2522i1$, $2522i2$ for each fluorophore. The real component, or the magnitude, of the complex value of each pixel of the lifetime corrected images can be used to generate the final images $2522i1$, $2522i2$ of the fluorophores in the real space. The imaginary component of the complex value of each pixel of the lifetime corrected images can be discarded, or not calculated. The images of the different fluorophores can be combined to generate an image of a cell by, for example, assigning different colors to the images of the different fluorophores and combining the different images with colors to generate the image of the cell.

In some embodiments, the actions of the method 2500 include entirely of linear operations, so multiple action can be consolidated. The method can be implemented on a FPGA for sort applications. In some embodiments, some actions of the method can include only linear operations which can be consolidated.

In some embodiments, the method 2500 can be implemented in the case of cross-excitation mixing with fluorophores excited from conventional (or non-imaging) lasers. The total amount of mixing in the case of cross-excitation can be measured. Spatial distribution of the cross-excited fluorophores can be determined using the image data from the fluorophores excited from conventional lasers. Additionally or alternatively, with prior knowledge of the relevant cell surface markers, one of the FIRE channels that contains the proper spatial distribution can be used as a substitute of one or more of the cross-excited fluorophores. For example, if a cross-excited fluorophore is attached to a surface marker, the spatial distribution of that fluorophore can be assumed to be the same as that of another surface marker with a fluorophore that is excited from one of the FIRE channels.

FIG. 26A-26B are composite images showing non-limiting exemplary results of spectral unmixing. FIG. 26A is a composite image of FIRE images of CD3+ T cells stained with anti-CD16/CD56 antibody bound with phycoerythrin (PE), anti-CD3 antibody bound with with PE-Texas Red, anti-DRAQ5 antibody bound with PE-Cy5, and anti-CD4 antibody bound with fluorescein isothiocyanate (FITC), without performing spectral unmixing. The cells shown were all CD16/CD56 negative, but the cells appear in FIG. 26A to be positive in the image due to spillover from FITC-tagged anti-CD4 antibody into the PE channel. FIG. 26B is a composite image of FIRE images, after spectral unmixing, of the CD3+ T cells shown in FIG. 26A. FIG. 26B shows that the spectral unmixing method disclosed herein successfully eliminated any trace of this spillover in the final images of the cells.

Spectral Unmixing Method

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells. The cell sorter system can comprise: a plurality of photodetectors configured to detect the fluorescence emissions of the plurality of fluorophores (e.g., each photodetector is configured to detect the fluorescence emission of a fluorophore of the plurality of fluorophores). The cell sorter system can comprise: non-transitory memory configured to store executable instructions; and a processor in communication with the non-transitory memory, the hardware processor programmed by the executable instructions to: cause the laser beam to illuminate the cell to elicit fluorescence emissions of a plurality of fluorophores associated with the cell. The computing system can cause the plurality photodetectors to detect the fluorescence emissions at the different wavelengths to obtain a plurality of channels of fluorescence intensity data corresponding to the plurality of fluorophores in a temporal space. The computing system can generate a plurality of raw images comprising a plurality of pixels of complex values in a frequency space from the plurality of channels of fluorescence intensity data. The computing system can generate a plurality of phase-adjusted images comprising a plurality of pixels of complex values in the frequency space from the plurality of raw images using one or more channel phase adjustments for each of the plurality of channels of the fluorescence intensity data. The computing system can generate a plurality of unmixed images comprising a plurality of pixels of complex values in the frequency space from the plurality of phase-adjusted images using an unmixing matrix on the complex values of corresponding pixels of the plurality of phase-adjusted images. The computing system can generate a plurality of phase-corrected images comprising a plurality of pixels of complex values in the frequency space from the plurality of unmixed images based on a property of each of the plurality of fluorophores. The computing system can determine a sorting decision for the cell based on the plurality of phase-corrected images.

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells; a plurality of photodetectors configured to detect the fluorescence emissions of the plurality of fluorophores (e.g., each photodetector is configured to detect the fluorescence emission of a fluorophore of the plurality of fluorophores); non-transitory memory configured to store executable instructions; and a processor in communication with the non-transitory memory, the hardware processor programmed by the executable instructions to: cause the laser beam to illuminate the cell to elicit fluorescence emissions of a plurality of fluorophores associated with the cell. The computing system can cause the plurality photodetectors to detect the fluorescence emissions at the different wavelengths to obtain a plurality of channels of fluorescence intensity data corresponding to the plurality of fluorophores in a temporal space. The computing system can generate a plurality of raw images comprising complex values in a frequency space from the plurality of channels of fluorescence intensity data. The computing system can generate a plurality of unmixed images comprising complex values in the frequency space from the plurality of raw images using an unmixing matrix on corresponding complex values of the plurality of raw images. The computing system can determine a sorting decision for the cell based on the plurality of unmixed images.

Disclosed herein include embodiments of a cell sorter system. In some embodiments, the cell sorter system comprises: a light source (e.g., a laser light source) configured to generate a light beam (e.g., a laser beam) having a plurality of different optical frequencies for eliciting fluorescence emissions at different wavelengths of a plurality of fluorophores associated with a cell of a sample comprising a plurality of cells; a plurality of photodetectors configured to detect the fluorescence emissions of the plurality of fluorophores (e.g., each photodetector is configured to detect the fluorescence emission of a fluorophore of the plurality of fluorophores); non-transitory memory configured to store executable instructions; and a processor in communication with the non-transitory memory, the hardware processor programmed by the executable instructions to: receive a plurality of channels of fluorescence intensity data, corresponding to the plurality of fluorophores in a temporal space, of the fluorescence emissions at the different wavelengths from the plurality of fluorophores associated with the cell, wherein the fluorescence emissions are detected by the plurality of photodetectors, and wherein the fluorescence emissions are elicited after the cell is illuminated by the laser light source. The computing system can generate a plurality of raw images comprising complex values in a frequency space from the plurality of channels of fluorescence intensity data. The computing system can generate a plurality of unmixed images comprising complex values in the frequency space from the plurality of raw images using an unmixing matrix on corresponding complex values of the plurality of raw images. The computing system can determine a sorting decision for the cell based on the plurality of unmixed images.

Figure 27:
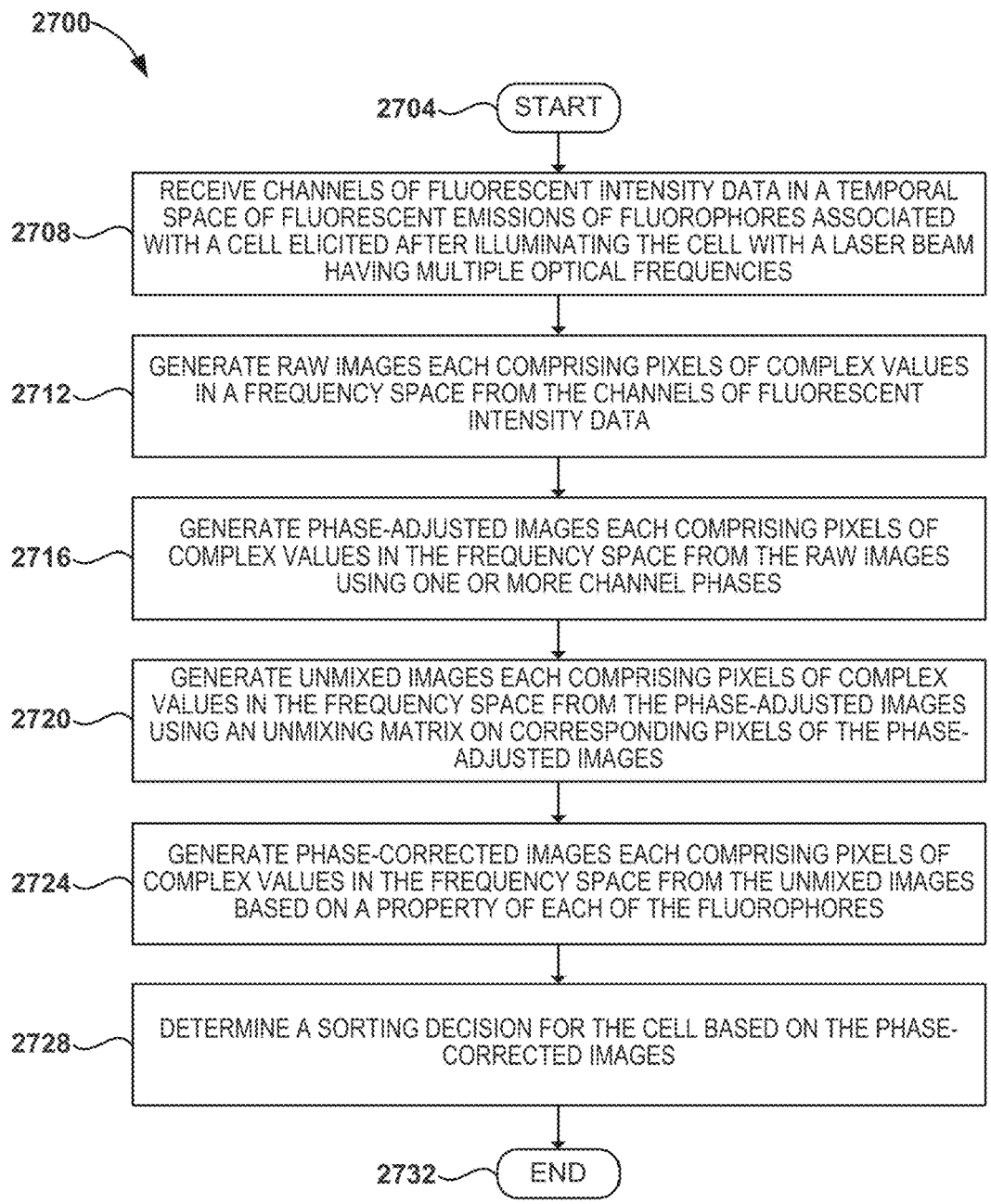
FIG. 27 is a flow diagram showing an exemplary method of spectral unmixing.

FIG. 27 is a flow diagram showing an exemplary method 2700 of spectral unmixing. The method 2700 may be embodied in a set of executable program instructions stored on a computer-readable medium, such as one or more disk drives, of a computing system. For example, the computing system 3000 shown in FIG. 30 and described in greater detail below can execute a set of executable program instructions to implement the method 2700. When the method 2700 is initiated, the executable program instructions can be loaded into memory, such as RAM, and executed by one or more processors (e.g., one or more field-programmable gate arrays (FPGAs)) of the computing system 3000. Although the method 2700 is described with respect to the computing system 3000 shown in FIG. 30, the description is illustrative only and is not intended to be limiting. In some embodiments, the method 2700 or portions thereof may be performed serially or in parallel by multiple computing systems. Some blocks of the method 2700 can be combined and performed in parallel. The method 2700 can be used to determine a sorting decision for a cell of a sample, or sorting decisions of cells of a sample.

The computing system 3000 can be operationally coupled to a flow cytometer (e.g., the flow cytometer 2200 described with reference to FIG. 22). The computing system 3000 can be part of a cell sorter system, such as a flow cytometer. The computing system 3000 can control a light source (e.g., a laser light source). The light source can be configured to generate a light beam (e.g., a laser beam, such as the combined beam 49) having a plurality of different optical frequencies. The different optical frequencies can be used for eliciting fluorescence emissions (e.g., at different wavelengths) of a plurality of fluorophores associated with a cell of a sample. The computing system 3000 can receive fluorescent signals from a plurality of photodetectors (e.g., the photodetectors 106, 108, 110, 112 described with reference to FIGS. 7A-7B). Each photodetector can be configured to detect the fluorescence emission of a fluorophore of the plurality of fluorophores.

After the method 2700 begins at block 2704, the method 2700 proceeds to block 2708, where a computing system can receive a plurality of channels of fluorescence intensity data of fluorescence emissions (e.g., at different wavelengths) from the plurality of fluorophores associated with the cell. For example, each of the plurality of fluorophores can be bound to (e.g., conjugated with) a cellular component binding reagent (e.g., an antibody) that binds to the cell. The plurality of channels of fluorescent intensity data (e.g., the waveforms 2506c1, 2506c2 described with reference to the FIG. 25) can correspond to the plurality of fluorophores in a temporal space. For example, each channel of fluorescent data can include intensity values detected by a photodetector over a time period. The fluorescence emissions can be detected by a plurality of photodetectors. For example, the photodetectors 106, 108, 110, 112 described with reference to FIGS. 7A-7B can detect and generate the channels of the fluorescence intensity data). The fluorescence emissions can be elicited after the cell is illuminated by the laser light source.

In some embodiments, to receive the plurality of channels of fluorescence intensity data, the computing system can cause the laser beam to illuminate the cell to elicit fluorescence emissions of a plurality of fluorophores associated with the cell. The computing system can cause the plurality photodetectors to detect the fluorescence emissions at the different wavelengths to obtain the plurality of channels of fluorescence intensity data corresponding to the plurality of fluorophores in the temporal space.

The method 2700 proceeds from block 2708 to block 2712, where the computing system can generate a plurality of raw images (e.g., the raw images 2510$i$1, 2510$i$2 described with reference to the FIG. 25) comprising a plurality of pixels (e.g., the pixels 2510$i$1$p$00, 2510$i$1$p$01, 2510$i$2$p$00, 2510$i$2$p$01 described with reference to the FIG. 25) of complex values in a frequency space (e.g., the Fourier space) from the plurality of channels of fluorescence intensity data. The computing system can generate the plurality of raw images using a temporal-to-frequency transformation matrix representing the temporal-to-frequency space transformation. The plurality of raw images can comprise a plurality of pixels of complex values of the plurality of raw images.

In some embodiments, the laser beam comprises a reference laser beam (e.g., a LO beam) and a plurality of radiofrequency-shifted laser beams (e.g., the RF comb beams 24). The number of the plurality of radiofrequency-shifted laser beams can be $m_2$. The reference laser beam can spatially overlap the plurality of radiofrequency-shifted laser beams. In some embodiments, none of the plurality of radiofrequency-shifted laser beams spatially overlaps with one another. The reference laser beam and one or more of the plurality of radiofrequency-shifted laser beams can be capable of eliciting the fluorescence emission of a fluorophore of the plurality of fluorophores. Illuminating the cell can comprise illuminating a plurality of spatial locations of the cell (or a plurality of spatial locations 60 of a sample 62 described with reference to FIG. 4) with the plurality of radiofrequency-shifted laser beams concurrently. In some embodiments, none of the plurality of spatial locations of the cell overlaps with one another.

In some embodiments, the fluorescence emissions of two of the plurality of fluorophores overlap spectrally. The fluorescence emissions of three of the plurality of fluorophores overlap spectrally. The fluorescence emissions of five of the plurality of fluorophores overlap spectrally. The fluorescence emissions of a first fluorophore and a second fluorophore of the plurality of fluorophores overlap spectrally, and the fluorescence emissions of the second fluorophore and a third fluorophore of the plurality of fluorophores overlap spectrally. The fluorescence emissions of the first fluorophore and the third fluorophore overlap spectrally.

In some embodiments, to generate the plurality of raw images, the computing system can generate the plurality of raw images in the frequency space from the plurality of channels of fluorescence intensity data using a temporal-to-frequency space transformation. The temporal-to-frequency space transformation can comprise a Fourier transform. The Fourier transform can comprise a discrete Fourier transform.

The discrete Fourier transform can comprise a fast Fourier transform. The Fourier transform can comprise a sliding window Fourier transform. A sliding window of the sliding window Fourier transform can have a size of $m_1$. For example, the sliding window can have a size of, or a size of about, a size of at least, or a size of at most, $m_1$ data points (e.g., $m_1$ data points, such as $m_1$ continuous data points, of the fluorescent intensity data of one channel) such as 5, 10, 20, 50, 100, 200, 500 1000, 2000, 5000, 10000, 2000, 5000, 10000, 20000, 50000, 100000, 200000, 500000, 1000000, 2000000, 5000000, 10000000, or a number or a range between any two of these values, data points. As another example, the sliding window can have a size of, or a size of about, a size of at least, or a size of at most, $m_1$ seconds, such as $1\times10^{-1}$, $2\times10^{-1}$, $5\times10^{-1}$, $1\times10^{-2}$, $2\times10^{-2}$, $5\times10^{-2}$, $1\times10^{-3}$, $2\times10^{-3}$, $5\times10^{-3}$, $1\times10^{-4}$, $2\times10^{-4}$, $5\times10^{-4}$, $1\times10^{-5}$, $2\times10^{-5}$, $5\times10^{-5}$, $1\times10^{-6}$, $2\times10^{-6}$, $5\times10^{-6}$, $1\times10^{-7}$, $2\times10^{-7}$, $5\times10^{-7}$, $1\times10^{-8}$, $2\times10^{-8}$, $5\times10^{-8}$, $1\times10^{-9}$, $2\times10^{-9}$, $5\times10^{-9}$, or a number or a range between any two of these values, second. All sliding windows of the sliding window Fourier transform can have an identical size. The sliding windows of the sliding window Fourier transform can have 2, 5, 10, 20, 50, 100, or more sizes. The number of sliding windows of the sliding window Fourier transform with an identical size can be, 5, 10, 20, 50, 100, 200, 500, 1000, 2000, 5000, 10000, or more. In some embodiments, none of the sliding windows overlap. In some embodiments, two or more of the sliding windows overlap. For example, two sliding windows can overlap by, by about, by at least, or by at most, 5, 10, 20, 50, 100, 200, 500 1000, 2000, 5000, 10000, 2000, 5000, 10000, 20000, 50000, 100000, 200000, 500000, 1000000, 2000000, 5000000, 10000000, or a number or a range between any two of these values, data points. As another example, two sliding windows can overlap by, by about, by at least, or by at most, $1\times10^{-1}$, $2\times10^{-1}$, $5\times10^{-1}$, $1\times10^{-2}$, $2\times10^{-2}$, $5\times10^{-2}$, $1\times10^{-3}$, $2\times10^{-3}$, $5\times10^{-3}$, $1\times10^{4}$, $2\times10^{4}$, $5\times10^{4}$, $1\times10^{-5}$, $2\times10^{-5}$, $5\times10^{-5}$, $1\times10^{-6}$, $2\times10^{-6}$, $5\times10^{-6}$, $1\times10^{-7}$, $2\times10^{-7}$, $5\times10^{-7}$, $1\times10^{-8}$, $2\times10^{-8}$, $5\times10^{-8}$, $1\times10^{-9}$, $2\times10^{-9}$, $5\times10^{-9}$, or a number or a range between any two of these values, second. For example, two sliding windows can overlap by, by about, by at least, or by at most, 1%, 2%, 3%, 4%, 5%, 6%, 7%, 8%, 9%, 10%, 20%, 30%, 40%, 50%, 60%, 70%, 80%, 90%, 95%, 99%, 99.9% of the width of one of the sliding windows.

After generating the plurality of raw images at block 2712, the method 2700 proceeds to block 2716, where the computing system can generate a plurality of phase-adjusted images (e.g., the phase corrected images 2514*i*1, 2514*i*2 described with reference to the FIG. 25) comprising a plurality of pixels (e.g., the pixels 2514*i*1*p*00, 2514*i*1*p*01, 2514*i*2*p*00, 2514*i*2*p*01 described with reference to the FIG. 25) of complex values in the frequency space from the plurality of raw images using one or more channel phase adjustments for each of the plurality of channels of the fluorescence intensity data. The computing system can generate the plurality of phase-adjusted images using one or more channel phase adjustment matrices representing the one or more channel phase adjustments.

In some embodiments, the computing system can generate a plurality of phase-adjusted images comprising complex values in the frequency space from the plurality of raw images using one or more channel phase adjustments for each of the plurality of channels of the fluorescence intensity data. The plurality of phase-adjusted images can comprise a plurality of pixels of the complex values of the plurality of phase-adjusted images.

In some embodiments, the one or more channel phase adjustments correct for channel phases (e.g., channel-specific phases) comprising a brightfield phase, a calibration phase, and a phase offset for each of the plurality of channels. To generate the plurality of phase-adjusted images, the computing system can, for each channel of the plurality of channels: multiply the complex values of a raw image of the plurality of raw images corresponding to the channel with the one or more channel phase adjustments to generate a phase-adjusted image of the plurality of phase-adjusted images corresponding to the channel. To generate the plurality of phase-adjusted images, the computing system can, for each raw image of the plurality of raw images: multiply the complex values of the raw image with the one or more channel phase adjustments for the channel corresponding to the raw image to generate a phase-adjusted image of the plurality of phase-adjusted images.

The one or more channel phase adjustments can comprise, or comprise only, complex values. The one or more channel phase adjustments can comprise one or more real values. A channel phase matrix of a channel can comprise the one or more channel phase adjustments for the channel. The channel phase adjustment matrix can have a size of $n_1 \times n_1$. In some embodiments, the channel phase adjustment matrix can be a diagonal matrix. For example, only the diagonal elements of the channel phase adjustment matrix are non-zero. The diagonal elements of the channel phase adjustment matrix can be, or can be all, complex values. To generate the plurality of phase-adjusted images, the computing system can, for each channel of the plurality of channels: multiply the complex values of each row of the raw image of the plurality of raw images corresponding to the channel with a channel phase adjustment matrix for the channel to generate the corresponding row of the phase-adjusted image of the plurality of phase-adjusted images corresponding to the channel. To generate the plurality of phase-adjusted images, the computing system can, for each raw image of the plurality of raw images: multiply the complex values of each row of the raw image with a channel matrix for the channel to generate the corresponding row of the phase-adjusted image of the plurality of phase-adjusted images. The channel phase adjustment matrix, for correcting the one or more channel phases for each channel, can be unique for the channel. The computing system can determine or receive the one or more channel phase adjustments.

Appendix A of priority application Ser. No. 62/822,789 filed Mar. 22, 2019, the disclosure of which is herein incorporated by reference, shows a non-limiting exemplary method of performing phase calibration (e.g., for generating phase-adjusted images). Appendix B of priority application Ser. No. 62/822,789 filed Mar. 22, 2019, the disclosure of which is herein incorporated by reference, shows a non-limiting exemplary method of measuring phases at many frequencies simultaneously.

The method 2700 proceeds from block 2716 to block 2720, where the computing system can generate a plurality of unmixed images (e.g., the unmixed images 2518*i*1, 2518*i*2 described with reference to the FIG. 25) comprising a plurality of pixels (e.g., the pixels 2518*i*1*p*00, 2518*i*2*p*00 and the pixels 2518*i*1*p*01, 2518*i*2*p*01 described with reference to the FIG. 25) of complex values in the frequency space from the plurality of phase-adjusted images using an unmixing matrix (e.g., the unmixing matrix 2516*m* described with reference to FIG. 25) on the complex values of corresponding pixels (e.g., the pixels 2514*i*1*p*00, 2514*i*2*p*00 and the pixels 2514*i*1*p*01, 2514*i*2*p*01 described with reference to FIG. 25) of the plurality of phase-adjusted images. Each unmixed image can be considered to be an image of a fluorophore (or an image generated from fluorescence emission of a fluorophore) without any spectral mixing (or with minimal or reduced spectral mixing) from the fluorescent emissions of other fluorophores. To generate the plurality of unmixed images, the computing system can generate the plurality of unmixed images from the plurality of phase-adjusted images using the unmixing matrix on the corresponding complex values of the plurality of phase-adjusted images.

In some embodiments, to generate the plurality of unmixed images, the computing system can generate a vector comprising complex values of corresponding pixels (e.g., the pixels 2514*i*1*p*00, 2514*i*2*p*00 and the pixels 2514*i*1*p*01, 2514*i*2*p*01 described with reference to FIG. 25) of the plurality of phase-adjusted images. The computing system can multiply the vector with the unmixing matrix (e.g., the unmixing matrix 2516*m* described with reference to FIG. 25) to generate an unmixed vector comprising unmixed complex values (e.g., the values of the pixels 2518*i*1*p*00, 2518*i*2*p*00 and the pixels 2518*i*1*p*01, 2518*i*2*p*01 described with reference to FIG. 25). The computing system can generate the plurality of unmixed images comprising the corresponding pixels with the unmixed complex values. The vector can have a size of $1 \times n_1$, the unmixing matrix can have a size of $n_1 \times n_2$, and/or the unmixed vector can have a size of $1 \times n_2$. For example, $n_1$ and/or $n_2$ can be 1, 2, 3, 4, 5, 6, 7, 8, 9, 10, 20, 30, 40, 50, 60, 70, 80, 90, 100, 200, 500, 1000, or a number or a range between any two of these values. To generate the plurality of unmixed images, the computing system can generate the plurality of unmixed images from the plurality of phase-adjusted images using an unmixing matrix of a plurality of unmixing matrices, for corresponding pixels of the plurality of phase-adjusted images, on the complex values of the corresponding pixels. The plurality of unmixing matrices can comprise $m_2$ unmixing matrices, such as 1, 2, 3, 4, 5, 6, 7, 8, 9, 10, 20, 30, 40, 50, 60, 70, 80, 90, 100, 200, 500, 1000, or a number or a range between any two of these values unmixing matrices. The unmixing matrix can comprise, or comprise only of, real values and/or complex values.

In some embodiments, (1) the number of the plurality of photodetectors, the number of the plurality of raw images and/or the number of the plurality of phase-adjusted images (e.g., $n_1$) and (2) the number of the plurality of fluorophores, the number of the plurality of unmixed images and/or the number of phase-corrected images (e.g., $n_2$) can be identical. In some embodiments, (1) the number of the plurality of photodetectors, the number of the plurality of raw images and/or the number of the plurality of phase-adjusted images (e.g., $n_1$) and (2) the number of the plurality of fluorophores, the number of the plurality of unmixed images and/or the number of phase-corrected images (e.g., $n_2$) can be different. For example, the number of the plurality of phase-adjusted images (e.g., $n_1$) can be smaller than the number of the plurality of unmixed images (e.g., $n_2$). As another example, the number of the plurality of phase-adjusted images (e.g., $n_1$) can be bigger than the number of the plurality of unmixed images (e.g., $n_2$). For example, each of the plurality of phase-adjusted images can be generated from fluorescence intensity data detected by or received from a different photodetector of the plurality of photodetectors (e.g., after being transformed into the frequency space and/or phase adjusted). The number of the plurality of raw images, the number of the plurality of phase-adjusted images, and the number of the plurality of photodetectors can be identical (e.g., $n_1$). The fluorescence intensity data of the plurality of fluorophores can be detected by or using the plurality of photodetectors. Each of the plurality of phase-corrected images (and/or each of the plurality of unmixed images) can correspond to one of the plurality of fluorophores. The number of the plurality of unmixed images, the number of the plurality of phase-corrected images, and the number of the plurality of fluorophores can be identical (e.g., $n_2$). More photodetectors can be used to detect the fluorescence emissions of fewer fluorophores. For example, 10 photodetectors can be used to generate 10 channels of fluorescence intensity data of fluorescence emissions of eight fluorophores. Each of the plurality of unmixed images can correspond to one fluorophore of the plurality of fluorophores. Each of the plurality of unmixed images can be an image of one fluorophore of the plurality of fluorophores.

Figure 28A:
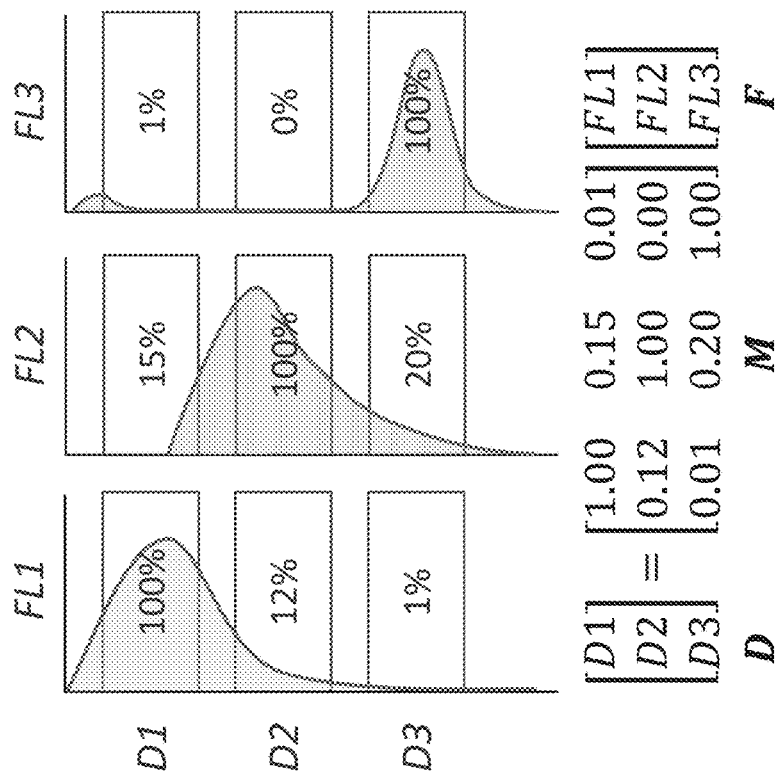
FIG. 28A is a schematic illustration of performing spectral unmixing with a square unmixing matrix.

Square unmixing matrix. Compensation can be performed where the number of channels is equal to the number of fluorophores (e.g., for area data). The unmixing matrix can be calculated once and used for all events and all pixels in each event. FIG. 28A is a schematic illustration of performing spectral unmixing with a square unmixing matrix. An unmixing matrix is also referred to as a spillover matrix. FIG. 28A shows that if the number of channels (three illustrated, collected by detectors D1, D2, and D3) and the number of fluorophores (three illustrated, labeled FL1, FL2, and FL3) are identical, a square unmixing matrix (or an inverse of a square mixing matrix) $M^{-1}$ can be used to determine the unmixed values F from detected values D. In the example illustrated in FIG. 28A, the fluorescence emissions detected by detector D1 includes 100% of the fluorescence emission of flourophore FL1 (e.g., the fluorescence emission of FL1 detected by D1 is normalized to 100%), 15% of the fluorescence emission of flourophore FL2 (e.g., relative to the fluorescence emission of FL1 detected by D1 normalized to 100%), and 1% of the fluorescence emission of flourophore FL3 (e.g., relative to the fluorescence emission of FL1 detected by D1 normalized to 100%). The fluorescence detected by detector D2 includes 100% of the fluorescence emission of flourophore FL2, 12% of the fluorescence emission of flourophore FL1, and 0% of the fluorescence emission of flourophore FL3. The fluorescence detected by detector D3 includes 100% of flourophore FL3, 1% of flourophore FL1, and 20% of flourophore FL2. The relationship between the fluorescence emissions from the three fluorophores and the fluorescence emissions detected by the three detectors can be expressed as D=M*F. Spectral unmixing can be performed using $M^{-1}$. For example, the fluorescence emissions of the three fluorophores F can be determined from the fluorescence emissions D using $M^{-1}$ by, for example, determining $M^{-1}$*D.

Non-square unmixing matrix. Spectral unmixing can be performed when we use more (or fewer) channels than fluorophores. FIGS. 28B1-28B2 is a schematic illustration of performing spectral unmixing with a non-square unmixing matrix and determining a non-square unmixing matrix. The number of photodetectors and the number of fluorophores can be different, and a non-square unmixing matrix can be used for spectral unmixing of fluorescence intensity data detected by the photodetectors. In the example shown in FIG. 28B1, 12 photodetectors detect fluorescence emissions of three fluorophores to generate 12 channels of fluorescence intensity data. Each channel of fluorescence intensity data can comprise a plurality of pixels with values in the frequency space of an image (e.g., a raw image or a phase-adjusted image) after the temporal-to-frequency space transformation at block 2712 and after performing phase adjustment at block 2716 described with reference to FIG.

27. For example, each of D1, . . . , D12 in FIG. 28B can be a corresponding pixel of each of the plurality of raw images or phase-adjusted images described with reference to FIG. 27. For example, D1 and D2 can be pixels $2514i1p00$, $2514i2p00$ of phase-adjusted images of two channels described with reference to FIG. 25. As another example, D1 and D2 can be pixels $2510i1p00$, $2510i2p00$ of raw images of two channels described with reference to FIG. 25. D1, . . . , D12 can correspond to 12 pixels from the 12 channels corresponding to one frequency bin or beat frequency. As another example, D1 in FIG. 28B1 can comprise a plurality of pixels corresponding to different frequency bins (e.g., of beat frequencies). Similarly, each of D2, . . . , D12 can comprise a plurality of pixels corresponding to different frequency bins. Each of D1, . . . , D12 can have a size of $m_2 \times 1$. FIG. 28B2 shows that if the number of channels and the number of fluorophores are different, an unmixing matrix can be determined using ordinary least squares (OLS) and/or weighted least squares (WLS) for spectral unmixing.

The computing system can receive and/or determine an unmixing matrix or a plurality of unmixing matrices (e.g., $m_2$). In some embodiments, an unmixing matrix (or a plurality of unmixing matrices, one for each frequency bin or pixel, or one for two or more frequency bins or pixels) can be determined using ordinary least squares (OLS), weighted least squares (WLS), Poisson regression, or a combination thereof. Other methods can be used to determine an unmixing matrix.

Ordinary least squares. In some embodiments, an unmixing matrix can be determined once with ordinary least squares (e.g., for area data) and used for spectral unmixing (e.g., to determine P as illustrated in FIG. 28B2). The unmixing matrix can be calculated once with the singular result used for all events (and all pixels in each event). Determining an unmixing matrix with ordinary least squares and/or performing spectral unmixing with such an unmixing matrix can be fast computationally (e.g., based on the number of calculations needed).

Weighted least squares. In some embodiments, an unmixing matrix can be determined using weighted least squares. The unmixing matrix determined based on weighted least squares can account for, or correct for, Poisson noise (for example, the variance of the value of a pixel can increase with the value). The unmixing matrix (or a plurality of unmixing matrices for different frequency bins or pixels) may have to be determined via matrix inversion for each plurality of corresponding pixels. An unmixing matrix can be determined via matrix inversion for each event (e.g., values of each plurality of corresponding pixels of different channels, or values of all corresponding pixels of different frequency bins of different channels from corresponding sliding windows in the sliding window Fourier transform). For example, an unmixing matrix (or the matrix W in FIG. 28B2) can be determined via matrix inversion for corresponding pixels $2514i1p00$, $2514i2p00$ of phase-adjusted images of two channels, another unmixing matrix can be determined via matrix inversion of corresponding pixels $2514i1p01$, $2514i2p01$ phase-adjusted images of two channels described with reference to FIG. 25. Determining an unmixing matrix with weighted least squares and/or performing spectral unmixing with such an unmixing matrix can be more computationally intensive than determining an unmixing matrix with ordinary least squares and/or performing spectral unmixing with such an unmixing matrix.

WLS can be more (e.g., much) more computationally expensive than OLS because of the use of the weight matrix, W. The unmixing matrix may need to be recomputed for each event. Computing the mixing matrix require a matrix inversion, which can be computationally expensive. The weights that make their way into the weight matrix can be based on an estimate of the variance of each pixel value (or each measurement). The weight matrix can be different for each pixel (or each plurality of corresponding pixels). The variance calculation can depend on the statistics inherent in the FIRE measurement. WLS can require a different and/or new unmixing matrix calculation for every pixel (or each plurality of corresponding pixels) in every event.

Poisson regression. In some embodiments, an unmixing matrix (or a plurality of unmixing matrices for different frequency bins or pixels) can be determined using Poisson regression and/or a generalized linear model based on Poisson noise model. For example, an unmixing matrix can be determined using maximum likelihood estimation (MLE) using optimization techniques, such as convex optimization techniques. Determining an unmixing matrix using Poisson regression can include per-event convex optimization solving. An unmixing matrix determined using Poisson regression and/or performing spectral unmixing using such an unmixing matrix can correctly accounts for, or corrects for, noise (e.g., per channel noise). In some embodiments, an unmixing matrix determined using Poisson regression can outperform an unmixing matrix determined using ordinary least square or weighted least square. Determining an unmixing matrix with Poisson regression and/or performing spectral unmixing with such an unmixing matrix can be more computationally intensive than determining an unmixing matrix with weighted least squares and/or performing spectral unmixing with such an unmixing matrix.

Referring to FIG. 27, after generating the plurality of unmixed images at block 2720, the method 2700 proceeds to block 2724, where the computing system can generate a plurality of phase-corrected images from the plurality of unmixed images based on a property of each of the plurality of fluorophores. The computing system can generate the plurality of phase-corrected images using a plurality of fluorophore phase correction matrix for the fluorophore representing the plurality of fluorophore phase corrections. Each phase-corrected image can comprise a plurality of pixels of complex values in the frequency space. The plurality of phase-corrected images can comprise a plurality of pixels of the complex values of the plurality of phase-corrected images. The computing system can generate a plurality of phase-corrected images comprising complex values in the frequency space from the plurality of unmixed images based on a property of each of the plurality of fluorophores. The computing system can determine or receive the plurality of fluorophore phase corrections for the fluorophore.

In some embodiments, each phase-corrected image can comprise a plurality of pixels of real values in the frequency space. The plurality of phase-corrected images can comprise a plurality of pixels of the real values of the plurality of phase-corrected images. The computing system can generate a plurality of phase-corrected images comprising real values in the frequency space from the plurality of unmixed images based on a property of each of the plurality of fluorophores.

In some embodiments, to generate the plurality of phase-corrected images, the computing system can generate a phase-corrected image of the plurality of phase-corrected images from a unmixed image of the plurality of unmixed images corresponding to a channel of the plurality of channels using a plurality of fluorophore phase corrections (e.g., lifetime) of a fluorophore of the plurality of fluorophores corresponding to the channel. In some embodiments, to generate the plurality of phase-corrected images, the computing system can generate a phase-corrected image of the plurality of phase-corrected images from a unmixed image of the plurality of unmixed images corresponding to a fluorophore of the plurality of fluorophores using one or more fluorophore phase corrections (e.g., a set of lifetime correction) of the fluorophore of the plurality of fluorophores. The plurality of fluorophore phase corrections for the fluorophore can be related to a property of the fluorophore. The property of the fluorophore can comprise a lifetime of the fluorophore. The plurality of fluorophore phase corrections for the fluorophore can comprise complex values.

To generate the plurality of phase-corrected images, the computing system can, for each unmixed image of the plurality of unmixed images: multiply the complex values of each row of the unmixed image with a fluorophore phase correction matrix for the fluorophore to generate the corresponding row of the phase-corrected image of the plurality of phase-corrected images corresponding to the fluorophore. The fluorophore phase correction matrix for a fluorophore can comprise the one or more fluorophore phase corrections for the fluorophore. The fluorophore phase correction matrix for a fluorophore can be unique for the fluorophore. The fluorophore phase correction matrix can comprise, or comprise only one or more complex values. The fluorophore phase correction matrix can comprise one or more real values. The fluorophore phase correction matrix can have a size of $n_2 \times n_2$. In some embodiments, the fluorophore phase correction matrix can be a diagonal matrix. For example, only the diagonal elements of the fluorophore phase correction matrix are non-zero. The diagonal elements of the fluorophore phase correction matrix can be, or can be all, complex values. The fluorophore phase correction matrix can be unique for each fluorophore.

In some embodiments, each channel phase adjustment matrix (or channel phase adjustment) comprises elements with complex values. Each channel phase adjustment matrix can comprise elements with only complex values. Each channel phase adjustment matrix can comprise one or more elements with real values (e.g., the imaginary component of a complex value is zero). In some embodiments, each unmixing matrix comprise elements with real values. Each unmixing matrix can comprise elements with only real values. In some embodiments, each fluorophore phase correction matrix comprises elements with complex values. Each channel phase adjustment matrix can comprise elements with only complex values. Each channel phase adjustment matrix can comprise one or more elements with real values (e.g., the imaginary component of a complex value is zero).

In some embodiments, each raw image comprise pixels with complex values. Each raw image can comprise pixels with only complex values. Each raw image can comprise one or more pixels with real values. In some embodiments, each phase-adjusted image comprises pixels with complex values. Each phase-adjusted image can comprise pixels with only complex values. Each phase-adjusted image can comprise one or more pixels with real values. In some embodiments, each unmixed image comprises pixels with complex values. Each unmixed image can comprise pixels with only complex values. Each unmixed image can comprise one or more pixels with real values.

In some embodiments, each phase-corrected image comprises pixels with complex values. Each phase-corrected image can comprise pixels with only complex values. Each phase-corrected image can comprise one or more pixels with real values. Each phase-corrected image can comprise pixels only with real values. For example, the fluorophore phase correction matrix for a fluorophore can rotate the complex values of the pixels of the unmixed image of the fluorophore to the axis of the real component such that the imaginary component of each pixel of the fluorophore phase-corrected image is zero. As another example, the fluorophore phase correction matrix for a fluorophore can rotate the complex values of the pixels of the unmixed image of the fluorophore to the axis of the real component such that the imaginary component of each pixel of the fluorophore phase-corrected image is close to zero and is discarded (or not calculated at all).

Figure 29:
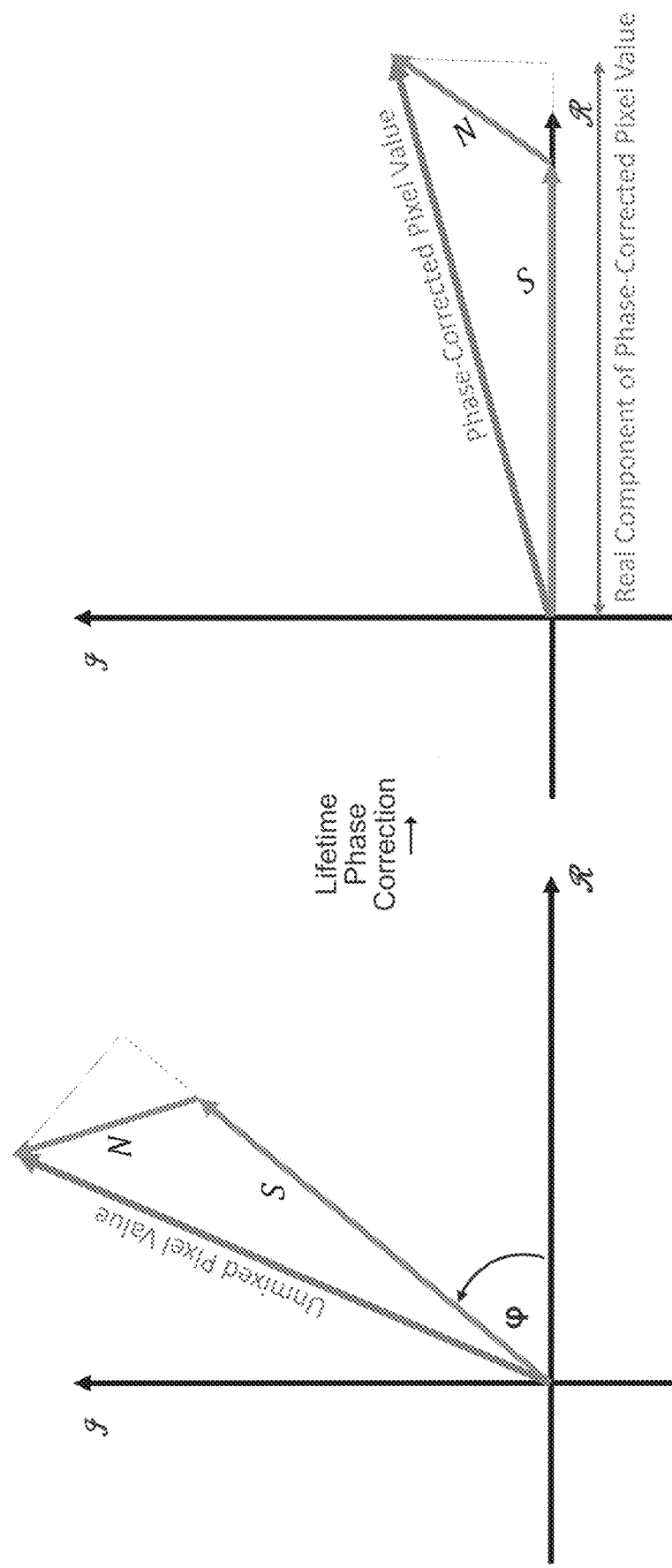
FIG. 29 is a schematic illustration of fluorophore phase correction.

FIG. 29 schematically illustrates fluorophore phase correction. A pixel of an unmixed image of a fluorophore can be a complex value comprising a signal phase S and a noise phase N. The complex value of the pixel can be phase corrected. Based on the lifetime of the fluorophore, the fluorophore phase for the fluorophore (e.g., the fluorophore phase corresponding to the beat frequency of the pixel) can be determined and used for fluorophore phase correction. For example, the fluorophore phase can be (or be based on) φ, which can be used to determine a fluorophore phase correction for the fluorophore. The fluorophore phase correction (e.g., in the form of a fluorophore phase correction matrix) can be used for correcting for the fluorophore phase of the pixel of the unmixed image. FIG. 29 shows that the real component of the complex value of the pixel after phase correction is closer to the signal of the complex value of the pixel in the unmixed image than the magnitude of the complex value of the pixel. In some embodiments, a higher signal to noise ratio can be achieved by shifting (e.g., rotating with fluorophore phase correction) the complex value of each pixel of an unmixed image corresponding to a fluorophore based on the known phase of the fluorophore and taking the real component of the complex value of the pixel after fluorophore phase correction.

Referring to FIG. 27, in some embodiments, the number of the plurality of raw images, the number of the plurality of phase-adjusted images, the number of the plurality of unmixed images, and the number of the plurality of phase-corrected images are identical. The number of the plurality of raw images, the number of the plurality of phase-adjusted images, the number of the plurality of unmixed images, and/or the number of the plurality of phase-corrected images can be $n_1$. The plurality of raw images can be associated with a first temporal dimension and a first frequency dimension. The plurality of phase-adjusted images can be associated with a second temporal dimension and a second frequency dimension. The plurality of unmixed images can be associated with a third temporal dimension and a third frequency dimension. The plurality of phase-corrected images can be associated with a fourth temporal dimension and a fourth frequency dimension.

Two or more of the first temporal dimension, the second temporal dimension, the third temporal dimension, and the fourth temporal dimension can have an identical size and/or an identical number of pixels along the dimension. The first temporal dimension, the second temporal dimension, the third temporal dimension, and the fourth temporal dimension can have the identical size and/or the identical number of pixels. The first frequency dimension, the second frequency dimension, the third frequency dimension, and/or the fourth frequency dimension can have a size of $m_2$ and/or $m_2$ pixels (or Fourier transform bins), such as 5, 10, 20, 50, 100, 200, 500 1000, 2000, 5000, 10000, 2000, 5000, 10000, 20000, 50000, 100000, 200000, 500000, 1000000, 2000000, 5000000, 10000000, or a number or a range between any two of these values, data points. One or more of the first frequency dimension, the second frequency dimension, the third frequency dimension, and the fourth frequency dimension can have an identical size and/or an identical number of pixels. The first frequency dimension, the second frequency dimension, the third frequency dimension, and the fourth frequency dimension can have the identical size and/or the identical number of pixels. $m_2$ and $m_1$ can be different in different implementations. For example, $m_2$ can be equal ½ *$m_1$. As another example, $m_2$ is smaller than ½ *$m_1$. $m_2$ and ½ *$m_1$ can differ by, by about, by at least, or by at most, 1, 2, 3, 4, 5, 6, 7, 8, 9, 10, 20, 30, 40, 50, 60, 70, 80, 90, 100, 200, 500, 1000, 2000, 5000, 10000, 20000, 50000, 100000, 200000, 500000, 1000000, 2000000, 5000000, 10000000, or a number or a range between any two of these values.

The size of and/or the number of pixels along the first frequency dimension, the size of and/or the number of pixels along the second frequency dimension, the size of and/or the number of pixels along the third frequency dimension, and/or the size of and/or the number of pixels of the fourth frequency dimension can be identical to the number of the plurality of radiofrequency-shifted laser beams. The pixels along the first frequency dimension, the pixels along the second frequency dimension, the pixels along the third frequency dimension, and/or the pixels along the fourth frequency dimension can correspond to the plurality of radiofrequency-shifted laser beams. The bins of Fourier transform (e.g., discrete Fourier transform) that do not correspond to the radiofrequency-shifted laser beams or the frequencies of that radiofrequency-shifted laser beams can be discarded (or not computed). The pixels along the first frequency dimension, the pixels along the second frequency dimension, the pixels along the third frequency dimension, and/or the pixels along the fourth frequency dimension can correspond to the plurality of spatial locations of the cell.

In some embodiments, the computing system can generate a plurality of visual representations of the plurality of phase-corrected images based on the real components of the complex values of the plurality of phase-corrected images. The computing system can generate a plurality of visual representations of the plurality of phase-corrected images based on the amplitudes of the complex values of the plurality of phase-corrected images. The computing system can generate a combined visual representation (e.g., an image of a cell shown in FIG. 26B) from the plurality of visual representations of the plurality of phase-corrected images. To generate the combined visual representation, the computing system can assign a color to each of the plurality of visual representations (or the corresponding fluorophores); generate a plurality of colored visual representations of the plurality of visual representations based on the color assigned to the visual representation, and combining the plurality of colored visual representation to generate the combined visual representation.

The method 2700 proceeds from block 2724 to block 2728, where the computing system determine a sorting decision for the cell based on the plurality of phase-corrected images. To determine the sorting decision, the computing system can determine the sorting decision for the cell based on the plurality of phase-corrected images. To determine the sorting decision, the computing system can determine the sorting decision for the cell based on the plurality of visual representations of the plurality of phase-corrected images. To determine the sorting decision, the hardware processor is programmed by the executable instructions to: determine the sorting decision for the cell based on the number of pixels of one or more of the plurality of phase-corrected images above a sorting decision threshold. The sorting decision threshold can be, be about, be more than, or be less than, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. To determine the sorting decision, the hardware processor is programmed by the executable instructions to: determine the sorting decision for the cell based on the percentage of pixels of one or more of the plurality of phase-corrected images above a sorting decision threshold. The sorting decision threshold can be, be about, be more than, or be less than, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values. The method 2700 ends at block 2732.

Two or more of blocks 2712, 2716, 2720, 2724, and 2728 can be performed together. In some embodiments, the computing system can perform two or more of generating the plurality of raw images, generating the plurality of phase-adjusted images, generating the plurality of unmixed images, and generating the plurality of phase-corrected images is performed using a combined matrix comprising, or representing two or more of a temporal-to-frequency transformation matrix, a channel phase adjustment matrix, an unmixing matrix, and a fluorophore phase correction matrix. To generate the plurality of raw images and generate the plurality of phase-adjusted images, the computing system can generate the plurality of phase-adjusted images from the plurality of channels of fluorescence intensity data using a combined matrix comprising, or representing, a temporal-to-frequency transformation matrix and a channel phase adjustment matrix. To generating the plurality of unmixed images and generate the plurality of phase-corrected images, the computing system can generate the plurality of phase-corrected images from the plurality of phase-adjusted images using a combined matrix comprising, or representing, an unmixing matrix and a fluorophore phase correction matrix. For example, corresponding rows of pixels of the plurality of phase-adjusted images (e.g., pixels 2514$i$1$p$00, 2514$i$1$p$01, . . . of the phase-adjusted image 2514$i$1 and pixels 2514$i$2$p$00, 2514$i$2$p$01, . . . of the phase-adjusted image 2514$i$2) can be combined into a row vector. The row vector can be multiplied by a combined matrix comprising, or representing, an unmixing matrix and a fluorophore phase correction matrix to generate a row vector comprising corresponding rows of pixels of the plurality of phase-corrected images (e.g., pixels 2522$i$1$p$00, 2522$i$1$p$01, . . . of the phase-corrected image 2522$i$1 and pixels 2522$i$2$p$00, 2522$i$2$p$01, . . . of the phase-corrected image 2522$i$2). To generate the plurality of raw images, generate the plurality of phase-adjusted images, generate the plurality of unmixed images, and generate the plurality of phase-corrected images, the computing system can generate the plurality of phase-corrected images from the plurality of channels of fluorescence intensity using a combined matrix comprising, or representing, a temporal-to-frequency transformation matrix, a channel phase adjustment matrix, an unmixing matrix, and a fluorophore phase correction matrix.

In some embodiments, the computing system can generate a plurality of channels of corrected fluorescence intensity data from the plurality of phase-corrected images. To generate the plurality of channels of corrected fluorescence intensity data, the computing system can generate the plurality of channels of corrected fluorescence intensity data form the plurality of phase-corrected images using a frequency- to temporal-space transformation. The computing system can determine an estimate of a characteristic of the cell based on the plurality of channels of corrected fluorescence intensity data. Determining the sorting decision can comprise determining the sorting decision of the cell based on the estimate of the characteristic of the cell as described herein (such as the methods described with reference to FIGS. 14A, 14C, 14D, 16, 18, 19A, 19B, 20A, 20B, and 28, or portions thereof). The characteristic of the cell can comprise a size of the cell, a ratio of sizes of the cell in two different dimensions, co-localization of fluorescence emissions by two or more of the plurality of fluorophores associated with the cell, a ratio of sizes of the cytoplasm and the nucleus of the cell, a degree of punctateness of fluorescence emission of the cell, a measure of the spatial distribution of the fluorescence emission, a measure of location or orientation of the cell, a measure of the eccentricity of the cell, a measure of the similarity of the cell to a reference cell, a measure of the degree to which the cell lies in a focal point of the laser beam, or a combination thereof.

Execution Environment

Figure 30:
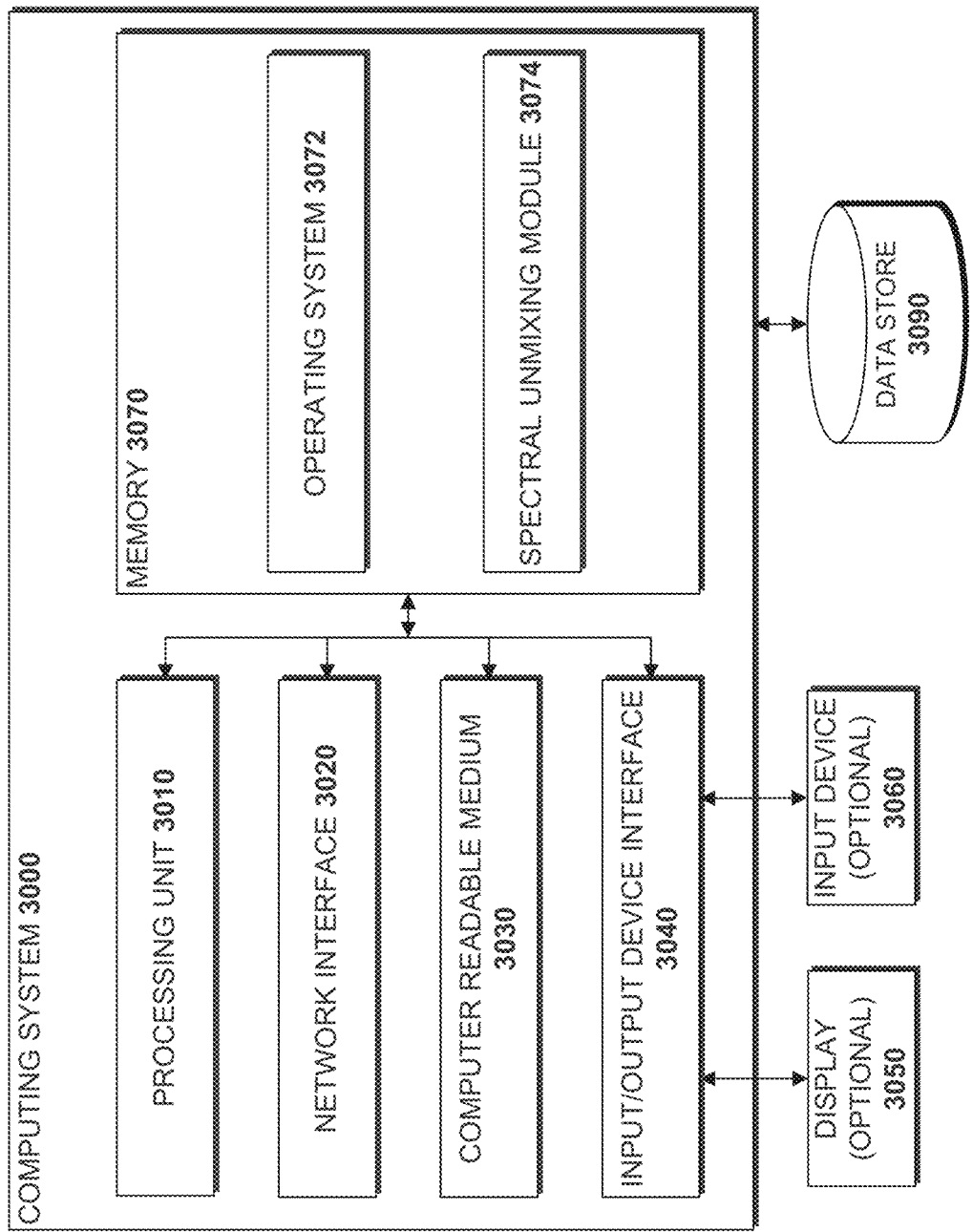
FIG. 30 is a block diagram of an illustrative computing system configured to implement embodiments of a method of spectral unmixing.

In FIG. 30 depicts a general architecture of an example computing device 3000 configured to implement the metabolite, annotation and gene integration system disclosed herein. The general architecture of the computing device 3000 depicted in FIG. 30 includes an arrangement of computer hardware and software components. The computing device 3000 may include many more (or fewer) elements than those shown in FIG. 30. It is not necessary, however, that all of these generally conventional elements be shown in order to provide an enabling disclosure. As illustrated, the computing device 3000 includes a processing unit 3010, a network interface 3020, a computer readable medium drive 3030, an input/output device interface 3040, a display 3050, and an input device 3060, all of which may communicate with one another by way of a communication bus. The network interface 3020 may provide connectivity to one or more networks or computing systems. The processing unit 3010 may thus receive information and instructions from other computing systems or services via a network. The processing unit 3010 may also communicate to and from memory 3070 and further provide output information for an optional display 3050 via the input/output device interface 3040. The input/output device interface 3040 may also accept input from the optional input device 3060, such as a keyboard, mouse, digital pen, microphone, touch screen, gesture recognition system, voice recognition system, gamepad, accelerometer, gyroscope, or other input device.

The memory 3070 may contain computer program instructions (grouped as modules or components in some embodiments) that the processing unit 3010 executes in order to implement one or more embodiments. The memory 3070 generally includes RAM, ROM and/or other persistent, auxiliary or non-transitory computer-readable media. The memory 3070 may store an operating system 3072 that provides computer program instructions for use by the processing unit 3010 in the general administration and operation of the computing device 3000. The memory 3070 may further include computer program instructions and other information for implementing aspects of the present disclosure.

For example, in one embodiment, the memory 3070 includes a spectral unmixing module 3074 for performing spectral unmixing, such as the spectral unmixing method 2500 described with reference to FIG. 25 and the spectral unmixing method 2700 described with reference to FIG. 27. In addition, memory 3070 may include or communicate with the data store 3090 and/or one or more other data stores that store fluorescence emissions or signals, raw images, phase-adjusted images, unmixed images, phase-corrected images, and/or sorting decisions.

Terminology

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields, buttons, or other interactive controls for receiving input signals or providing electronic information or for providing information to the user in response to any received input signals. A UI may be implemented in whole or in part using technologies such as hyper-text mark-up language (HTML), JAVASCRIPT™, FLASH™, JAVA™, .NET™, WINDOWS OS™, macOS™, web services, or rich site summary (RSS). In some implementations, a UI may be included in a stand-alone client (for example, thick client, fat client) configured to communicate (e.g., send or receive data) in accordance with one or more of the aspects described.

As used herein a "data store" may be embodied in hard disk drives, solid state memories and/or any other type of non-transitory computer-readable storage medium accessible to or by a device such as an access device, server, or other computing device described. A data store may also or alternatively be distributed or partitioned across multiple local and/or remote storage devices as is known in the art without departing from the scope of the present disclosure. In yet other embodiments, a data store may include or be embodied in a data storage web service.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed sort strategy processor, which may include one or more processors, such as one or more digital signal processors (DSPs), configurable microprocessors, an application specific integrated circuits (ASICs), field programmable gate arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. In some aspects, the functionality described herein may be provided within dedicated software modules or hardware modules configured for encoding and decoding, or incorporated in a specialized sorting control card.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A cell sorter system comprising:
a laser light source configured to generate a laser beam having a plurality of different optical frequencies for eliciting fluorescence emissions at different wavelengths of a plurality of fluorophores associated with a cell of a sample comprising a plurality of cells;
a plurality of photodetectors configured to detect the fluorescence emissions of the plurality of fluorophores;
non-transitory memory configured to store executable instructions; and
a processor in communication with the non-transitory memory, the hardware processor programmed by the executable instructions to:
cause the laser beam to illuminate the cell to elicit fluorescence emissions of a plurality of fluorophores associated with the cell;
cause the plurality photodetectors to detect the fluorescence emissions at the different wavelengths to obtain a plurality of channels of fluorescence intensity data corresponding to the plurality of fluorophores in a temporal space;
generate a plurality of raw images comprising complex values in a frequency space from the plurality of channels of fluorescence intensity data;
generate a plurality of unmixed images comprising complex values, or real values, in the frequency space from the plurality of raw images using an unmixing matrix on corresponding complex values of the plurality of raw images; and
determine a sorting decision for the cell based on the plurality of unmixed images.

2. The cell sorter system of claim 1, wherein the hardware processor comprises a field-programmable gate array (FPGA).

3. The cell sorter system of claim 1, wherein to generate the plurality of raw images, the processor is programmed by the executable instructions to: generate the plurality of raw images in the frequency space from the plurality of channels of fluorescence intensity data using a temporal-to-frequency space transformation.

4. The cell sorter system of claim 3, wherein the temporal-to-frequency space transformation comprises a Fourier transform.

5. The cell sorter system of claim 1, wherein the processor is programmed by the executable instructions to: receive the one or more channel phase adjustments.

6. The cell sorter system of claim 1, wherein to generate the plurality of unmixed images, the processor is programmed by the executable instructions to:
generate a vector comprising complex values of corresponding pixels of the plurality of phase-adjusted images;
multiply the vector with the unmixing matrix to generate an unmixed vector comprising unmixed complex values; and
generate the plurality of unmixed images comprising the corresponding pixels with the unmixed complex values.

7. The cell sorter system of claim 6, wherein the vector has a size of 1×1, wherein the unmixing matrix has a size of n1×n2, and/or the unmixed vector has a size of 1×n2.

8. The cell sorter system of claim 1, wherein to generate the plurality of unmixed images, the processor is programmed by the executable instructions to: generate the plurality of unmixed images from the plurality of phase-adjusted images using an unmixing matrix of a plurality of unmixing matrices, for corresponding pixels of the plurality of phase-adjusted images, on the complex values of the corresponding pixels.

9. The cell sorter system of claim 8, wherein the plurality of unmixing matrices comprises m2 unmixing matrices.

10. The cell sorter system of claim 1, wherein the unmixing matrix comprises real values.

11. The cell sorter system of claim 1, wherein the processor is programmed by the executable instructions to: generate a phase-corrected image of the plurality of phase-corrected images from a unmixed image of the plurality of unmixed images corresponding to a fluorophore of the plurality of fluorophores using a plurality of fluorophore phase corrections for the fluorophore of the plurality of fluorophores.

12. The cell sorter system of claim 1, wherein the processor is programmed by the executable instructions to: receive the plurality of fluorophore phase corrections for the fluorophore.

13. The cell sorter system of claim 1, wherein to determine the sorting decision, the hardware processor is programmed by the executable instructions to: determine the sorting decision for the cell based on the number of pixels of one or more of the plurality of phase-corrected images above a sorting decision threshold.

14. The cell sorter system of claim 1, wherein to determine the sorting decision, the hardware processor is programmed by the executable instructions to: determine the sorting decision for the cell based on the percentage of pixels of one or more of the plurality of phase-corrected images above a sorting decision threshold.

15. The cell sorter system of claim 1, wherein the processor is programmed by the executable instructions to: generate a plurality of visual representations of the plurality of phase-corrected images based on the real components of the complex values of the plurality of phase-corrected images.

16. The cell sorter system of claim 1, wherein the processor is programmed by the executable instructions to: generate a plurality of visual representations of the plurality of phase-corrected images based on the amplitudes of the complex values of the plurality of phase-corrected images.

17. The cell sorter system of claim 1, wherein to determine the sorting decision, the processor is programmed by the executable instructions to: determine the sorting decision for the cell based on the plurality of visual representations of the plurality of phase-corrected images.

18. The cell sorter system of claim 1, wherein the laser beam comprises a reference laser beam and a plurality of radiofrequency-shifted laser beams.

19. The cell sorter system of claim 1,
wherein the plurality of raw images is associated with a first temporal dimension and a first frequency dimension,
wherein the plurality of phase-adjusted images is associated with a second temporal dimension and a second frequency dimension,
wherein the plurality of unmixed images is associated with a third temporal dimension and a third frequency dimension, and/or
wherein the plurality of phase-corrected images is associated with a fourth temporal dimension and a fourth frequency dimension.

20. The cell sorter system of claim 1, wherein the fluorescence emissions of two of the plurality of fluorophores overlap spectrally.

* * * * *